(12) United States Patent
Yi

(10) Patent No.: US 7,993,639 B2
(45) Date of Patent: *Aug. 9, 2011

(54) THERAPEUTIC COMPOSITIONS AND METHODS USEFUL IN MODULATING PROTEIN TYROSINE PHOSPHATASES

(75) Inventor: Taolin Yi, Solon, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 635 days.

This patent is subject to a terminal disclaimer.

(21) Appl. No.: 12/071,647

(22) Filed: Feb. 25, 2008

(65) Prior Publication Data

US 2009/0028823 A1    Jan. 29, 2009

Related U.S. Application Data

(63) Continuation of application No. 10/238,007, filed on Sep. 9, 2002, now Pat. No. 7,416,723.

(60) Provisional application No. 60/317,993, filed on Sep. 7, 2001.

(51) Int. Cl.
  *A61K 45/00* (2006.01)
  *A61K 38/21* (2006.01)
  *A01N 59/16* (2006.01)
  *A01N 55/02* (2006.01)

(52) U.S. Cl. ............... 424/85.7; 424/85.4; 424/85.1; 424/65.1; 514/503

(58) Field of Classification Search ............ None
See application file for complete search history.

(56) References Cited

U.S. PATENT DOCUMENTS

| | | |
|---|---|---|
| 5,334,374 A | 8/1994 | Hartley et al. |
| 5,759,837 A | 6/1998 | Kuhajda et al. |
| 5,859,065 A | 1/1999 | Brandes |
| 6,020,179 A | 2/2000 | Goli |
| 6,143,765 A | 11/2000 | Tang et al. |
| 6,177,460 B1 | 1/2001 | Camden |
| 6,197,306 B1 | 3/2001 | Murali |
| 6,207,145 B1 | 3/2001 | Tovey |
| 6,258,582 B1 | 7/2001 | Acton |
| 6,388,076 B1 | 5/2002 | Mjalli et al. |
| 6,410,586 B1 | 6/2002 | Moller et al. |
| 6,569,853 B1 | 5/2003 | Borisy et al. |
| 6,693,125 B2 | 2/2004 | Borisy et al. |

FOREIGN PATENT DOCUMENTS

WO    WO 00/21506 A3    4/2000

OTHER PUBLICATIONS

Adachi, M., E.H. Fishcher, J. Ihle, K. Imai, F. Jirik, B. Neel, T. Pawson, S. Shen, M. Thomas, A. Ullrich, and Z. Zhao, Mammaliam SH2-containing protein tyrosin phosphatases. Cell 85:15, 1996.

Alexander, J., K.C. Carter, N. Al-Fasi, A. Satoskar and F. Brombacher, Endogenous IL-4 is necessary for effective drug therapy against visceral leishmaniasis. Eur J Immunol, 2000, 30: 2935-43.

Aoki, N. and T. Matsuda. A cytosolic protein-tyrosine phosphatase PTP1B specifically dephosphorylates and deactivates prolactin-activated STAT5a and STAT5b. J Biol Chem, 2000, 275: 39718-26.

Ayub, M. and M.J. Levell. Inhibition of testicular 17 alpha-hydrosylase and 17,20-lyase but not 3 beta-hydroxysteroid dehydrogenase-isomerase or 17 beta-hydroxysteroid oxidoreductase by ketocanazole and other imidazole drugs. J Steroid Biochem, 1987, 28: 521-3.

Bennett, J. M., Catovsky, D., Daniel, M.T., Flandrin, G., Galton, D.A. Gralnick, H.R. and Sultan, C. Criteria for the diagnosis of acute leukemia of megakaryocyte lineage (M7). A report of the French-American-British Cooperative Group. Ann Intern Med., 103: 460-2, 1985.

Bennett, J.M., Catovsky, D., Daniel, M.T., Flandrin, G., Galton, D.A. Gralnick, H.R. and Sultan, C. Proposal for the recognition of minimally differentiated acute myeloid leukaemia (AML-MO) Br J Haematol, 78: 325-9, 1991.

Bergamaschi, G., Carlo-Stella, C., Cazzola, M., De Fazio, P., Pedrazzoli, P., Peverali, F.A. and Della Valle, G. Tumor necrosis factor alpha down-regulates c-myc mRNA expression and induces in vitro monocytic differentiation in fresh blast cells from patients with acute myeloblastic leukemia. Leukemia, 4: 426-30, 1990.

Buchdunger, E., et al., Inhibition of the Abl Protein-Tyrosine Kinase in Vitro an in Vivo by a 2-phenyiaminopyrimidine derivative, Cancer Res, 1996, 56: 100-04.

Berman, J. and T.J. O'Leary. Gastrointestinal stromal tumor workshop. Hum Pathol, 2001, 32: 578-82.

(Continued)

*Primary Examiner* — Anand Desai
*Assistant Examiner* — Iqbal H Chowdhury
(74) *Attorney, Agent, or Firm* — Tarolli, Sundheim, Covell & Tummino LLP

(57) ABSTRACT

In one embodiment, a therapeutic composition containing a pentavalent antimonial is provided. The pentavalent antimonial can be sodium stibogluconate, levamisole, ketoconazole, and pentamidine and biological equivalents of said compounds. Additionally, pentavalent antimonials that can be used in accordance with the present invention may be any such compounds which are anti-leishmaniasis agents. The therapeutic composition of this embodiment contains an effective amount of pentavalent antimonial that can be used in treating infectious diseases. The types of diseases that can be treated with the present invention include, but are not limited to, the following: diseases associated with PTPase activity, immune deficiency, cancer, infections (such as viral infections), hepatitis B, and hepatitis C. The types of cancers that the present embodiment can be used to treat include those such as lymphoma, multiple myeloma, leukemia, melanoma, prostate cancer, breast cancer, renal cancer, bladder cancer. The therapeutic composition enhances cytokine activity. The therapeutic composition may include a cytokine, such as interferon α, interferon β, interferon γ, or granulocyte/macrophage colony stimulating factor.

18 Claims, 22 Drawing Sheets

OTHER PUBLICATIONS

Berman, J.D. and M. Grogl. Leishmania mexicana: chemistry and biochemistry of sodium stibogluconate (Pentostam). Exp Parasitol, 1988, 67: 96-103.

Berman, J.D., G. Holz Jr. and D.H. Beach. Effects of ketoconazole on growth and sterol biosynthesis of Leishmania mexicana promastigotes in culture. Mol Biochem Parasitol, 1984, 12: 1-13.

Berman J.D. and Wyler, D.J. An in vitro model for investigation of chemotherapeutic agents in leishmaniasis. J. Infect. Dis., 142: 83-86, 1988.

Berman, J.D. Chemotherapy for leishmaniasis: biochemical mechanisms, clinical efficacy, and future strategies. Rev Infect Dis, 10: 560-86, 1988.

Bittorf, T., Seiler, J., Zhang, Z., Jaster, R. and Brock, J. SHP1protein tyrosine phosphatase negatively modulates erythroid differentiation and suppression of apoptosis in J2E erythroleukemic cells. Biol Chem, 380: 1201-9, 1999.

Blanchette, J., Racette, N., Faure, R., Siminovitch, K.A. and Olivier, M. Leishmania-induced increases in activation of macrophage SHP-1 tyrosine phosphatase are associated with impaired IFN-gamma-triggered JAK2 activation. EUR J Immunol, 29: 3747-44, 1999.

Bloomfield, C.D. and Brunning, R.D. The revised French-American-British classificatio of acute myeloid leukemia: is new better? Ann Intern Med, 103: 614-6, 1985.

Bleumer et al. "Immunotherapy for renal cell carcinoma", Eur. Urol. 44(1): 65-75 (2003).

Blume-Jensen, P. and Hunter, T. Oncogenic kinase signaling. Nature, 411: 355-365, 2001.

Bok, R.A. and E.J. Small. The treatment of advanced prostate cancer with ketoconazole: safety issues. Drug Saf, 1999, 20: 451-8.

Borden E.C. Reducing primary melanoma mortality. Curr Oncol Rep, 2000, 2: 289-91.

Borden, E.C., Lindner, D., Dreicer, R., Hussein, M. and Peereboom, D. Second-generation interferons for cancer: clinical targets. Semin Cancer Biol, 10: 125-44, 2000.

Bradbury, J. Metastasis in colorectal cancer associated with phosphatase expression. Lancet, 358: 1245, 2001.

Breitman, T.R., Selonick, S.E. and Collins, S.J. Induction of differentiation of the human promyelocytic leukemia cell line (HL-60) by retinoic acid. Proc Nati Acad Sci USA, 77: 2936-40, 1980.

Buick, R.N., R. Pullano, and J.M. Trent, Comparative properties of five human ovarian adenocarcinoma cell lines. Cancer Res., 45: 3668-76, 1985.

Burke, T., Jr., and Z.Y. Zhang, Protein-tyrosine phosphatases: structure, mechanism, and inhibitor discovery. Biopolymers 47: 225, 1998.

Burshtyn D.N., Scharenberg, A.M., Wagtmann, N., Rajagopalan, S., Berrada, K., Yi, T., Kinet, J.P. and Long, E. O. Recruitment of tyrosine phosphatase HCP by the killer cell inhibitor receptor. Immunity, 4: 77-85, 1996.

Burshtyn, D.N., Yang, W., Yi, T. and Long, E.O. A novel phosphotyrosine motif with a critical amino acid at position -2 for the SH2 domain-mediated activation of the tyrosine phosphatase SHP-1. J Biol Chem, 272: 13066-72, 1997.

Cailleau, R., Young, R., Olive, M. and Reeves, W., Jr. Breast tumor cell lines from pleural effusions. J Natl Cancer Inst, 53: 661-74, 1974.

Castrucci, M.R., P. Bilsel, and Y. Kawaoka, Attenuation of influenza A virus by insertion of a foreign epitope into the neuraminidase. J. Virol, 66: 4647-53, 1992.

Carini, C., Hudspith, B.N. and Brostoff, J. Effect of prostaglandins and cyclic nucleotides on growth and immunoglobulin secretion of two IgE myeloma cell lines. Br J Cancer, 43: 257-60, 1981.

Carter, J.D., B.G. Neel and U. Lorenz. The tyrosine phosphatase SHP-1 influences thymocyte selection by setting TCR signaling thresholds. Int Immunol 11: 1999-2013.

Cates, C.A. et al., Cancer Lett, 110: 49-55, 1992.

Chakravortty, D., Kato, Y., Sugiyama, T., Koide, N., Mu, M. M., Yoshida, T. and Yokochi, T. The inhibitory action of sodium arsenite on lipopolysaccharide-induced nitric oxide production in RAW 267.4 macrophage cells: a role of Raf-1 in lipopolysaccharide signaling. .1 munol, 166: 2011-7, 2001.

Chawla-Sarkar, M., Leaman, D.W., Jacobs, B.S., Tuthill, R.J., Charrerjee-Kishore, M., Stark, G.R., Borden, E.C., Resistance to interferons in melanoma cells does not correlate with the expression or activation of signal transducer activator of transcription 1 (stat 1). J. Interferon Cytokine Res. 22: 603-13, 2002.

Chen, H., Chang, S., Trub, T. and Neel, B.G. Regulation of colony-stimulating factor 1 receptor signaling by the SH2 domain-containing tyrosine phosphatase SHPTP1. Mol. Cell. Biol., 16: 3685-3697, 1996.

Chen, Y-T., Holcomb, C., Moore, H-P. H. Expression and localization of two low molecular weight GTP-binding proteins, Rab8 and Rab10, by epitope tag. Proc. Nat. Acad. Sci USA 90: 6508-6512, 1993.

Chen, G.Q. et al., In Vitro Studies on Cellular and Molecular Mechanisms of Arsenic Trioxide (As2O3) in the Treatment of Acute Promyelocytic Leukemia: As2O3 induces NB4 Cell Apoptosis with Downregulation of BCl-2 Expression and Modulation of PML-RAR alpha/PML proteins; Blood 1996, 88: 1052-1061.

Chou, T.C. and Talalay, P. Quantitative analysis of dose-effect relationships: the combined effects of multiple drugs or enzyme inhibitors. Adv Enzyme Regul, 22: 27-55, 1984.

Church, D., Zhang, Y., Rago, R. and Wilding, G. Efficacy of suramin against human prostate carcinoma DU145 xenografts in nude mice. Cancer Chemother Pharmacol, 43: 198-204, 1999.

Collins, S.J., Ruscetti, F.W., Gallagher, R.E. and Gallo, R.C. Normal functional characteristics of cultured human promyelocytic leukemia cells (HL-60) after induction of differentiation by dimethylsulfoxide. J. Exp Med, 149: 969-74, 1979.

Cyster, J.G. and Goodnow, C.C. Protein tyrosine phosphatase 1C negatively regulates antigen receptor signaling in B lymphocytes and determines thresholds for negative selection. Immunity, 2: 13-24, 1995.

Damen, J.E. Cutler, R.L., Jiao, H., Yi, T. and Krystal, G. Phosphorylation of tyrosine 503 in the erythropoietin receptor (EpR) is essential for binding the P85 subunit of phosphatidylinositol (PI) 3-kinase and for EpR-associated PI 3-kinase activity. J Biol Chem, 270: 23402-23408, 1995.

Darnell, J., Jr., Studies of IFN-induced transcriptional activation uncover the Jak-Stat pathway. J. Interferon Cytokine Res., 18: 549-54, 1998.

David, M., Chen, H.E., Goetz, S., Larner, A.C. and Neel, B.G. Differential regulation of the alpha/beta interferon-stimulated Jak/Stat pathway by the SH2 domain-containing tyrosine phosphatase SHPTP1. Mol Cell Biol, 15: 7050-7058, 1995.

Diamond, R.H. et al., Mol Cell Biol, 14: 3752-62, 1994.

De, B.P. et al., Specific Interaction in Vitro and in Vivo of glyceraldehyde-e-phosphate Dehydrogenase and LA Protein with Cis-acting RNAs of Human Parainfluenze Virus Type 3, J Biol Chem, 271: 24738-35, 1996.

de Bruijn P. Kehrer Df, Verweij J. Sparreboom A. Liquid chromatographic determination of ketoconazole, a potent inhibitor of CYP3A4-mediated metabolism. J Chromatogr B biomed Sci Appl. Apr. 5. 2001; 753(2):395-400.

de Veer, M.J., M. Holko, M. Frevel, E. Walker, S. Der, J.m. Paranjape, R.H. silverman and B.R. Williams Functional classification of interferon-stimulated genes identified using microarrays. J Leukoc Biol, 2001, 69: 912-20.

Denu, J.M. and dixon, J.E. Protein tyrosine phosphatases: mechanisms of catalysis and regulation. Curr Opin Chem Biol, 2: 633-41, 1998.

Drewinko, B., M.M. Romsdahl, L.Y. Yang, M.J. Ahearn, and J.M. Trujillo, Establishment of a human carcinoembryonic antigen-producing colon adenocarcinoma cell line. Cancer Res. 36: 467-75, 1976.

Druker, B.J., Sawyers, C.L., Kantarjian, H., Resta, D. J., Reese, S.f., Ford, J.M., Capdeville, R. and Talpaz, M. Activity of a specific inhibitor of the BCR-ABL tyrosine kinase in the blast crisis of chronic myeloid leukemia and acute lymphoblastic leukemia with the Philadelphia chromosome. N Engl J Med, 344: 1038-42, 2001.

Druker, B.J., Talpaz, M., Resta, D.J., Peng, B., Buchdunger, E., Ford, J.M., Lydon, N. B., Kantarjian, H., Capdeville, R., Ohno-Jones, S.

and Sawyers, C.L. Efficacy and safety of a specific inhibitor of the BCR-ABL tyrosine kinase in chronic myeloid leukemia. N Engl J Med, 344: 1032-7, 2001.

Ellery, J.M., S.J. Kempshall, and P.J. Nicholls. 2000. Activation of the interleukin 2 receptor: a possible role for tyrosine phosphatases. Cell Signal 12:367.

Elson, A., Leder, P. Identification of a cytoplasmic, phorbol ester-inducible isoform of protein tyrosine phosphatase epsilon. Proc. Natl. Acad. Sci. USA 92: 12235-39, 1995.

Espinoza-Delgado, I., M.C. Bosco, T. Musso, G.L. Gusella, D.L. Longo, and L. Varesio. 1995. Interleukin-2 and human monocyte activation. J Leukoc Biol 57:13.

Fauman, E.B. And M.A. Saper, Structure and function of the protein tyrosine phosphatases. Trends Biochem Sci, 1996, 21: 413-7.

Fenaux, P., Chastang, C., Chevret, S., Sanz, M., Dombret, H., Archimbaud, E., Fey, M., Rayon, C., Huguet, F., Sotto, J.J., Gardin, C., Makhoul, P.C., Travade, P., Solary, E., Fegueux, N., Bordessoule, D., Miguel, J.S., Link, H., Desablens, B., Stamatoullas, A., Deconinck, E., Maloisel, F., Castaigne, S., Preudhomme, C. and Degos, L. A randomized comparison of all transretinoic acid (ATRA) followed by chemotherapy and ATRA plus chemotherapy and the role of maintenance therapy in newly diagnosed acute promyelocytic leukemia. The European APL Group. Blood, 94: 1192-200, 1999.

Forget, G., K.A. Siminovitch, S. Brochu, S. Rivest, D. Radzioch, and M. Olivier. 2001. Role of host pholtyrosine phosphatase SHP-1 in the development of murine leishmaniasis. Eur J. Immunol 31:3185.

Forsberg, K., Valyi-Nagy, I., Heldin, C.H., Herlyn, M. and Westermark, B, Platelet-derived growth factor (PDGF) in oncogenesis: development of a vascular connective tissue stroma in xenotransplanted human melanoma producing PDGF-BB. Proc Natl Acad Sci USA, 90: 393-7, 1993.

Frank, D.A. and Sartorelli, A.c. Alterations in tyrosine phosphorylation during the granulocytic maturation of HL-60 leukemia cells. Cancer Res, 48: 52-8, 1988.

Frearson, J.A., Yi, T. and Alexander, D.R. A tyrosine-phosphorylated 110-120-kDa protein associates with the C-terminal SH2 domain of phosphotyrosine phosphatase-1D in T cell receptor-stimulated T cells. Eur. J. Immunol., 26: 1539-1543, 1996.

Gallagher, R., collins, S., Trujillo, J., Ruscetti, F. Gallo, R., Characterization of the continuous, differentiating myeloid cell line (HL-60) from a patient with acute promyelocytic leukemia. Blood, 54: 713-33, 1979.

Gianni', M., Kalac, Y., Ponzanelli, I., Rambaldi, A., Terao, M. and Garattini, E. Tyrosine kinase inhibitor ST1571 potentiates the pharmacologic activity of retinoic acid in acute promyelocytic leukemia cells: effects on the degradation of RARalpha and PML-RARalpha. Blood, 97: 3234-43, 2001.

Gianni, M., Terao, M., Zanotta, S., Barbui, T., Rambaldi, A. and Garattini, E. Retinoic acid and granulocyte colony-stimulating factor synergistically induce leukocyte alkaline phosphatase in acute promyelocytic leukemia cells. Blood, 83: 1909-21, 1994.

Gianni, M., Zanotta, S., Terao, M., Rambaldi, A. and Garattini, E. Interferons induce normal and aberrant retinoic-acid receptors type alpha in acute promyelocytic leukemia cells: potentiation of the induction of retinoid-dependent differentiation markers. Int J Cancer, 68: 75-83, 1996.

Giard, D.J., S.a. Aaronson, g.J. Todaro, P. Arnstein, J.H. Kersey, H. dosik, and W.P. Parks, In vitro cultivation of human tumors establishment of cell lines derived from a series of solid tumors. J. Natl. Cancer Inst., 51: 1417-23, 1973.

Gillis, S., and J. Watson, 1980, Biochemical and biological characterization of lymphocyte regulatory molecules. V. Identification of an interleukin 2-producing human leukemia T cell line. J Exp Med 152: 1709.

Goldman, J.M. and Melo, J.V. Targeting the BCR-ABL tyrosine kinase in chronic myeloid leukemia. N Engl J Med, 344: 1084-6, 2001.

Goodwin, J.G. and Page, J.E. A study of the excretion of organic antibonials using a polarographic procedure. Biochem. J., 37: 198-209, 1943.

Goodwin, L.G. Pentostam (sodium stibgluconate); a 50-year personal reminiscence. Trans R Soc Trop Med Hyg. 89: 339-41, 1995.

Gore, S.D., Weng, L.J., Jones, R.J., cowan, K., Zilcha, M., Piantadosi, S. and Burke, P.J. Impact of in vivo administration of interleukin 3 on proliferation, differentiation, and chemosensitivity of acute myeloid leukemia. Clin Cancer Res, 1: 295-303, 1995.

Gorre, M.E., M. Mohammed, K. Ellwood, N. Hsu, R. Paquette, P.N. Rao and C.L. Sawyers. Clinical Resistance to STI-571 Cancer Therapy Caused by BCR-ABL Gene Mutation or Amplification. Science, 2001, 293: 876-80.

Green, M.C., and L.D. Schultz. 1975. Motheaten, an immunodeficient mutant of the mouse. I. Genetics and pathology. J. Hered 66: 250.

Greenlee, R.T., M.B. Hill-Harmon, T. Murray, and M. Thun. 2001, Cancer statistics, 2001. Ca Cancer J. Clin 51:15.

Guan, K-L, Dixon, J.E. Evidence for Protein-tyrosine-phosphatase Catalysis Proceeding via a Cystein-Phosphate Intermediate. J. Biol. Chem. 266: 17026-30, 1991.

Haque, S.J., V. Flati, A. Deb and B.R. Williams. Protein-tyrosine phosphatases in Stat 1 alpha-mediated cell signaling. J Biol Chem, 1995, 270: 25709-14.

Hague, S.J., P. Harbor, M. Tabrizi, T. Yi and B.R. Williams. Protein-tyrosine phosphatase Shp-1 is a negative regulator of IL-4- and IL-13-dependent signal transduction. J Biol Chem, 1998, 273: 3893-6.

He, L.Z,, Merghoub, T. and Pandolfi, P.O. In vivo analysis of the molecular pathogenesis of acute promyelocytic leukemia in the mouse and its therapeutic implications. Oncogene, 18: 5278-92. 1999.

Heffetz, D., Bushkin, I., Dror, R. and Zick, Y. The insulinornimetic agents H2O2 and vanadate stimulate protein tyrosine phosphorylation in intact cells. J Biol Chem. 265: 2896-902, 1990.

Helson, L., S.K. Das, and S.I. Hajdu. Human neuroblastoma in nude mice. Cancer Res., 35: 2594-9, 1975.

Herwaldt, B.L. and Berman, J.D. Recommendations for treating leishmaniasis with sodium stibogluconate (Pentostam) and review of pertinent clinical studies. Am J Trop Med Hyg, 46: 296-306, 1992.

Herwaidt, B.L., Kaye, E. T., Lepore, T.J., Berman, J.D. and Baden, H.P. Sodium stibogluconate (Pentostam) overdose during treatment of American cutaneous leishmaniasis. J Infect dis, 165: 968-71, 1992.

Hirai, H., Shimazaki, C., Yamagata, N., Goto, H., Inaba, T., Kikuta, T., Sumikuma, T., Sudo, Y., Ashihara, E., Fujita, N., Hibi, S., Imashuku, S., Ito, E. and Nakagawa, M. Effects of thrombopoietin (c-mpl ligand) on growth of blast cells from patients with transient abnormal myelopoiesis and acute myeloblastic leukemia. Eur J Haematol, 59: 38-46, 1997.

Hooft van Huijsduijnen, R. Protein tyrosine phosphatases: counting the trees in the forest. Gene, 225: 1-8, 1998.

Hsu, H.C., Tsai, W.H., Hsu, M.L., Ho, C.H, and Wang, S.Y. Effects of colony-stimulating factors on the all-trans retinoic acid-induced differentiation of acute promyelocytic leukemic cells. Chung Hua I Hsueh Tsa Chih, 57: 93-9, 1996.

Hunter, T. The role of tyrosine phosphorylation in cell growth and disease. Harvey Lect. 94: 81-119, 1998.

Huyer, G., S. Liu, J. Kelly, J. Moffat, P. Payette, B. Kennedy, G. Tsaprailis, M.J. Gresser and C. Ramachandran. Mechanism of inhibition of protein-tyrosine phosphatases by vanadate and pervanadate. J Biol Chem, 1997, 272: 843-51.

Idres, N., Benoit, G., Flexor, M.A., Lanotee, M. and Chabot, G.G. Granulocytic differentiation of human NB4 promyelocytic leukemia cells induced by all-trans retinoic acid metabolites. Cancer Res, 61: 700-5, 2001.

Ihle, J.N., Thierfelder, W., Teglund, S., Stravapodis, D., Wang, D., Feng, J. and Parganas, E. Signaling by the cytokine receptor superfamily. ann NY Acad Sci, 865: 1-9, 1998.

Irie-Sasaki, J., Sasaki, T., Matsumoto, W., Opaysky, A., Cheng, M., Welstead, G., Griffiths, E., Krawczyk, C., Richardson, C.D., Aitken, K., Iscove, N., Koretzky, g., Johnson, P., Liu, P., Rothstein, D.M. and Penninger, J. CD45 is a JAK phosphatase and negatively regulates cytokine receptor signaling. Nature, 409: 349-54, 2001.

James, S.Y., Williams, M.A., Kelsey, S.M., Newland, A.C. and Colston, K.W. Interaction of vitamin D derivatives and granulocyte-macrophage colony-stimulating factor in leukaemic cell differentiation. Lukernia, 11: 1017-25, 1997.

Jennings, C.D., Foon, K.A. Recent Advances in Flow Cytometry: Application to the Diagnosis of Hematologic Malignancy. Blood 90: 2863-2892, 1997.

Jiao, H., Berrada, K., Yang, W., Tabrizi, M., Platanias, L.C. and Yi, T. Direct association and dephosphorylation of Jak2 kinase by SH2 domain-containing protein tyrosine phosphatase SHP-1, Mol. Cell. Biol., 16: 6985-6992, 1996.

Jiao, H., Yang, W., Berrada, K., Tibrizi, M., Shultz, L. and Yi, T. Macrophages from motheaten viable motheaten mutant mice show increased proliferative response to GM-CSF: detection of potential HCP substrates in GM-CSF signal transduction. Exp. Hematol., 25: 592-600, 1997.

Johnson, K.G., LeRoy, F.G., Borysiewicz, L.K. and Matthews, R.J. TCR signaling thresholds regulating T cell development and activation are dependent upon SHP-1. J. Immunol. 162: 3802-13, 1999.

Joliat, M.J., P.A. Lang, B.L. Lyons, L. Burenski, M.A. Lynes, T. Yi, J.P. Sundberg, and L.D. Shultz 2002. Absence of CD5 dramatically reduces progression of pulmonary inflammatory lesions in SHP-1 protein-tyrosine phosphatase-deficient viable motheaten mice. J Autoimmun 18:105.

Kemp, M., Kurtzhals, J.A., Kharazmi, A. and Theander, T.G. Interferon-gamma and interleukin 4 in human Leislimania donovani infections. Immunol Cell Biol, 71: 583-7, 1993.

Klimp, A.H., E.G. de Vries, G.L. Scherphof, and T. Daemen. 2002. A potential role of macrophage activation in the treatment of cancer. Crit Rev Oncol Hematol 44: 143.

Klingmuller, U., Lorenz, U., Cantley, L.C., Neel, B.G. and Lodish, H.F. Specific recruitment of SH-PTP1 to the erythropoietin receptor causes inactivation of JAK2 and termination of proliferative signals. Cell, 80: 729-738,1995.

Kogan, S.C. and Bishop, J.M. Acut promyelocytic leukemia: from treatment to genetics and back. Oncogene, 18: 5261-7, 1999.

Kong, W., G.P. Swain, S. Li, and R.H. Diamond (2001) PRL-1 PTPase Expression is Developmentally Regulated With Tissue-Specific Patterns in Epithelial Tissues *Am J Physiol Gastrointest Liver Physiol*, 279, G613-21.

Lanotte, M., Martin-Thouvenin, V., Najman, S., Balerini, P., Valensi, F. and Berger, R. NB4, A maturation inducible cell line with t(15;17) marker isolated from a human acute promyelocytic leukemia (M3). Blood, 77: 1080-6, 1991.

Leibovitz, A., Stinson, J.C., McCombs, W.R., McCoy, C.E., Mazur, K.C., mabry, N. D., Classification of human colorectal adenocarcinoma cell lines. Cancer Res. 36: 4562, 1976.

Linder, D.J., Borden, E.C. and Kalvakolanu, D.V. Synergistic antitumor effects of a combination of interferons and retinoic acid on human tumor cells in vitro and in vivo. Clin Cancer Res, 3: 931-7, 1997.

Lorenz, U., K.S. Ravichandran, D. Pei, C.T. Walsh, S.J. Burakoff and B.G. Neel. Lck-dependent tyrosyl phosphorylation of the phosphotyrosine phosphatase SH-PTP1 in murine T cells. Mol Cell Biol, 1994, 14: 1824-34.

Lowenberg, B., Downing, J.R. and Burnett, A. Acute myeloid leukemia. N Engl J Med, 341: 1051-62, 1999.

Lu, C., Rak, J.,W., Kobayashi, H. and Kerbel, R.S. Increased resistance to oncostatin M-induced growth inhibition of human melanoma cell lines derived from advanced-stage lesions. Cancer Res, 53: 2708-11, 1993.

Mahmoud, A.A. and Warren, K.S. Algorithms in the diagnosis and management of exotic disease. XXIV. Leishmaniases. J Infect Dis, 136: 160-3, 1977.

Margolin, K.A. 2000. Interleukin-2 in the treatment of renal cancer. Semin Oncol 27:194.

Martiny, A., Vannier-Santos, M.A., Borges, V.M., Meyer-Fernandes, J.R., Assreuy, J., Cunha e Silva, N.L. and de Souza, W. Leishmania-induced tyrosine phosphorylation in the host macrophage and its implication to infection. Eur J Cell Biol, 71:206-15, 1996.

Masztalerz, A., N. Van Rooijen, W. Den Otter, and L.A. Everse. 2003. Mechanisms of macrophage cytotoxicity in IL-2 and IL-12 mediated tumor regression. Cancer Immunol Immunother 52: 235.

Matin, S.F., Rackley, R.R., Sadhukhan, P.C., Kim, M.S., Novick, A.C., Bandyopadhyay, S.K. Impaired alph-Interferon Signaling in Transitional Cell Carcinoma: Lack of p48 Expression in 5637 Cells. Cancer Res. 61: 2261-66, 2001.

Matte, C., Marquis, J.F., Blanchette, J., Gros, P., Faure, R., Posner, B.I. and Olivier, M. Peroxovanadium-mediated protection against murine leishmaniasis: role of the modulation of nitric oxide. Eur J Immunol, 30:2555-64, 2000.

Matter, W.F., et al., Biochem Biophys Res Cummun, 283: 1062-8, 2001.

Mattison, C.P., S.S. Spencer, K.A. Kresge, J. Lee and I.M, Ota. Differential regulation of the cell wall integrity mitogen-activated protein kinase pathway in budding yeast by the protein tyrosine phosphatases Ptp2 and Ptp3 Mol Cell Biol, 1999, 19: 7651-60.

Mauro, M.J. and Druker, B.J. Chronic myelogenous leukemia. Curr Opin Oncol, 13: 3-7, 2001.

Melnick, A. and Licht, J.D. Deconstructing a disease: RARalpha, its fusion partners, and their roles in the pathogenesis of acute promyelocytic leukemia. Blood, 93: 3167-215, 1999.

Metcalf, D. Cellular hernatopoiesis in the twentieth century. Semin Hematol, 36: 5-12, 1999.

Meurs, E. and Hovanessian, A.G. Alpha-interferon inhibits the expression of heavy chain mu messenger RNA in Daudi cells. Embo J, 7: 1689-96, 1988.

Mickey, D.D., Stone, K.R., Wunderli, H., Mickey, G,H,, Vollmer, R.T. and Paulson, D.F. heterotransplantation of a human prostatic adenocarcinoma cell line in nude mice. Cancer Res. 37: 4049-58, 1977.

Miletti, K.E. and M.J. Leibowitz, Pentamidine inhibition of group I intron splicing in *Candida albicans* correlates with growth inhibition. Antimicrob Agents Chemother, 2000, 44: 958-66.

Miyagishi, M., Taira, K. U6 promoter-driven siRNAs with four uriding 3' overhangs efficiently suppress targeted gene expression in mammalian cells. Nature Biotech. 19: 497-500, 2002.

Montagna, M., O. Serova, B.S. Sylla, J. Feuteun, and G.M. Lenoir, A 100-kb physical and transcriptional map around the EDH17B2 gene: identification of three novel genes and a pseudogene of a human homologue of the rate PRL-1 tyrosine phosphatase. Hum. Genet., 96, 532-8, 1995.

Mossmann, T., Rapid colorimetric assay for cellular growth and survival: application to proliferation and cytoxicity assays. J. Immunol. Methods, 65: 55-63, 1983.

Motzer, R.J., and P. Russo, 2000. Systemic Therapy for renal cell carcinoma. J Urol 163:408.

Mulders, P., R. Figlin, J.B. deKernion, R. Wiltrout, M. Linehan, D. Parkinson, W. deWolf, and A. Belldegrun. 1997 Renal cell carcinoma: recent progress and future directions. Cancer Res 57: 5189.

Murphy, G.P., and W.J. Hrushesky. 1973. A murine renal cell carcinoma. J Natl Cancer Inst 50: 1013.

Murray, H.W., et al., Immunochemotherapy for Intracellular *Leishmania donovani* infection: Gamma interferon Plus Pentavalent Antimony. J. Infect. Dis., 157: 973-8, 1988.

Murray, H.W., M.J. Oca, A.M. Granger, and R.D. Schreiber, 1989. Requirement for T cells and effect of lymphokines in successful chemotherapy for an intracellular infection. Experimental visceral leishmaniasis. J. Clin Invest 83: 1253.

Murray, H.W. et al., 2000. Interleukin-12 Regulates the Response to Chemotherapy in Experimental Visceral Leishmaniasis; J. Infect Dis. 182: 1497.

Murray, H.W. and S. Delph-Etienne. Roles of endogenous gamma interferon and macrophage microbicidal mechanisms in host response to chemotherapy in experimental visceral leishmaniasis. Infect Immun, 2000, 68: 288-93.

Naftalovich, S., E. Yefenof and Y. Eilam, Antitumor effects of ketoconazole and trifluoperazine in murine T-cell lymphomas. Cancer Chemother Pharmacol, 1991, 28: 384-90.

Nandan, D. and Reiner, N. E. Attenuation of gamma interferon-induced tyrosine phosphorylation in mononuclear phagocytes infected with *Leishmania donovani*: selective inhibition of signaling through Janus kinases and Stat1. Infect Immun, 63: 4495-500, 1995.

Nandan, D., Knutson, K.L., Lo, R. and Reiner, N. E. Exploitation of hose cell signaling machiner: activation of macrophage phosphotyrosine phosphates as a novel mechanism of molecular microbial pathogenesis. J Leukoc Biol, 67: 464-70, 2000.

Nandan, D., Lo, R. and Reiner, N.E. Activation of phosphotyrosine phosphatase activity attenuates mitogen-activated protein kinase signlaing and inhibits c-FOS and nitric oxide synthase expression in macrophages infected with *Leishmania donovani*. Infect Immun, 67: 4055-63, 1999.

Nanden, D., T. Yi, M. Lopez, C. Lai, and N. E. Reiner, 2002. *Leishmania* EF-lalpha activates the Src homology 2 domain containing tyrosine phosphatase SHP-1 leading to macrophage deactivation. J. Biol Chem 277: 50190.

O'Dwyer, M.E. and Druker, B.J. Status of bcr-abl tyrosine kinase inhibitors in chronic myelogcnous leukemia. Curr Opin Oncol, 12: 594-7,2000.

Olivier, M., Romero-Gallo, B. J., Matte, C., Blanchette, J., Posner, B.I., Tremblay, M.J. and Faure, R. Modulation of Interferon-gamma-induced macrophage activation by phosphotyrosine phosphatases inhibition. Effect on murine Leishmaniasis progression. J biol Chem, 273, 13944-9, 1998.

Pallen, C.J., The receptor-like protein tyrosine phosphatase alpha: a role in cell proliferation and oncogenesis. Semin. Cell Biol., 4: 403-8, 1993.

Parmiani, G., Rivoltini, L., Andreola, G. and Carrabba, M. Cytokines in cancer therapy. Immunol Lett, 74: 41-4, 2000.

Pathak, M.P. and T. Yi, Sodium Stibogluconate is a Potent Inhibitor of Protein Tyrosine Phosphatases and Augments Cytokine Response in Hemopoietic Cell Lines; The Journal of Immunology, 2001, 167: 3391-3397.

Pathak, Mk, X. Hu and T.Yi, Effects of Sodium Stibogluconate on Differentiation and Proliferation of Human Myeloid Leukemia Cell Lines in Vitro, Leukemia (2002) 16, 2285-2291.

Perez, J.M., M.C. Navarro-Ranninger, J.M. Requena, A. Jimenez-Ruiz, E. Parrondo, D. Craciunescu, M.C. Lopez and C. Alonso. DNA binding properties and antileukemic (L1210) activity of a Pt-pentamidine complex. Chem Biol Interact, 1991, 77: 341-55.

Perez, J.M., J.M. Requena, d. Craciunescu, J.C. Doadrio and c. Alonso. Binding of Pt-pentamidine to nucleosomal DNA. Studies of the antiproliferative activity of the drug against human cancer cells. Chem Biol Interact, 1993, 89: 61-72.

Peters, C.S., Liang, X., Li, S., Kannan, SI, Peng, Y., Taub, R., Diamond, R.H. ATF-7, a Novel bZIP Protein, Interacts with the PRL-1 Protein-tyrosine Phoshatase, J. Biol. chem. 275: 13718-26, 2001.

Platanias, L.C., P. Domanski, O.W. Nadeau, T. Yi, S. Uddin, E. Fish, B.G. Neel and O.R. Colamonici. Identification of a domain in the beta subunit of the type I interferon (IFN) receptor that exhibits a negative regulatory effect in the growth inhibitory action of typel IFNs. J Biol Chem, 1993, 273: 5577-81.

Platanias, L.C., Fish, E.N., Signaling pathways activated by interferons. Exp. Hematol., 27: 1583, 1999.

Puri, R.K. and Seigel, J.P. Interleukin-4 and cancer therapy. Cancer Invest. 11: 473-479, 1993.

Qin, Z., J. Schwartzkopff, F. Pradera, T. Kammertoens, b. Seliger, H. Pircher, and T. Blakenstein. 2003 A critical requirement of interferon gamma-medicated angiostasis for tumor rejection by CD8+T cells. Cancer Res. 63: 4095.

Raelson, J.V., Nervi, C., Rosenauer, A., Benedetti, L., Monczak, Y., Pearson, M., Pelicci, P.G. and Miller, W., Jr. The PML/RAR alpha oncoprotein is a direct molecular target of retinoic acid in acute promyelocytic leukemia cells. Blood, 88: 2826-32, 1996.

Rees, P.H., M.I. Keating P. A. Kager and W.T. Hockmeyer, Renal clearance of peritavalent antimony (sodium stibogluconate). Lancet. 1980, 2: 226-9.

Rice, G.P., Oger, J., Duquette, P., Fransic, G.S., Belanger, M., Laplante, S., Grertier, J.F., Treament with interferon beta-1b improves quality of life in multiple sclerosis. Can. J. Neurol. Sci., 26: 276, 1999.

Roberts, W.L., J. Hariprashad, P.M. Rainey and H.W. Murray. Pentavalent antimony-mannan conjugate therapy of experimental visceral leishmaniasis. Am. J. Trop. Med. Hyg., 55: 444-6, 1996.

Roberts, W.L. and P.M. Rainey. Antileishmanial activity of sodium stibogluconate fractions. Antimicrob Agents Chemother, 1993, 37: 1842-6.

Rochiltz D.F., L.E. Damon, M.B. Russi, A. Geddes and E.C. Cadman. Cytotoxieity of ketoconazole in malignant cell lines. Cancer Chemother Pharmacol, 1988, 21: 319-22.

Rosenberg, S.A. 2000. Interleukin-2 and the development of immunotherapy for the treatment of patients with cancer. Cancer J Sci Am 2000:S2.

Rosenberg, S.A. Progress in human tumor immunology and immunotherapy. Nature, 411: 380-384, 2001.

Safai, B., Samgadharan, M.G., Groopman, J.E., Arnett, K., Popovic, M., Sliski, A., Schupbach. J. and Gallo, R.C. Seroepidemiological studies of human T-lymphotropic retrovirus type III in acquired immunodeficiency syndrome. Lancet, 1:1438-40, 1984.

Saha., S., Bardelli, A., Buckhaults, P., Velculescu, V.E., Rago, C., St. Croix, B., Romans, K.E., Choti, M.A., Lengauer, C., Kinzler, K,W,, Vogelstein, B. Science, 294: 1343-6, 2001.

Salem, M., Delwel, R., Mahmoud, L.A., Clark, S., Elbasousy, E.M. and Lowenberg, B. Maturation of human acute myeloid leukaemia in vitro: the response to five recombinant haematopoietic factors in a serum-free system. Br J Haematol, 71: 363-70, 1989.

Samlowski, W.E., R. Petersen, S. Cuzzocrea, H. Macarthur, D. Burton, J.R. McGregor, and D. Salvermini, 2003. A nonpeptidyl mimic of superoxide dismutase, M40403, inhibits dose-limiting hypotension associated with interleukin-2 and increases its antitumor effects. Nat Med 9:750.

Schlesinger, M., Rabinowitz, R., Kertes, T., Ravid, Z. and Goldblum, N. Antibodies to human T lymphocytes in xenoantisera elicited with a new immature T-cell line (Peer). Thymus, 2: 235-43, 1981.

Schultz, L.D., D.R. Coman, C.L. Bailey, W.G. Beamer, and C.L. Sidman. 1984. "Viable motheaten," a new allele at the motheaten locust. I. Pathology. Am J Pathol, 116:179.

Schultz, L.D., P.A. Schweitzer, T.V. Rajan, T.Yi, J.N. Ihle, R.J. Matthews, M.L. Thomas, and D.R. Beier, 1993. Mutations at the murine motheaten locust are within the hematopoietic cell protein-tyrosine phosphatase (Hcph) gene. Cell 73: 1445.

Sonouchi, K., T.A. Hamilton, C.S. Tannenbaum, R.r, Tubbs, R. Bukowski, and J.H. Finke. 1994. Chemokine gene expression in the murine renal cell carcinoma, RENCA, following treatment in vivo with interferon-alpha and interleukin-2. Am J Pathol 144:747.

Squires, K.E., Schreiber, R.D., McElrath, M.J., Rubin, B.Y., Anderson, S,L., Murray, H.W., Experimental visceral leishmaniasis: role of endogenous IFN-gamma in hose defense and tissue granulomatous response. J. mmunol., 143: 4244, 1989.

Stanhope-Baker, P. and Williams, B.R. Identification of connective tissue growth factor as a large of WT1 transcriptional regulation. J Biol Chem, 275: 38139-50, 2000.

Stark, G.R. Genetic analysis of interfereon and other mammalian signaling pathways. Harvey Lect. 93: 1-16, 1997.

Steck, E.A. The leishmaniases. Prog Drug Res, 1974, 18: 289-351.

Sundar, S., P.R. Sinha, N.K. Agrawal, R. Srivastava, P.N. Rainey, J.D. Berman, H.W. Murray and V.P. Singh. A cluster of cases of sever cardiotoxicity among kala-azar patients treated with a high-osmolarity lot of sodium antimony gluconate. Am J Trop Med Hyg, 1998, 59: 139-43.

Sundstrom, C. and Nilsson, K. Establishment and characterization of a human histiocytic lymphoma cell line (U-937). Int J Cancer, 17: 565-77, 1976.

Tabiti, K., D.R. Smith, H.S. Goh and C.J. Pallen. Increased mRNA expression of the receptor-like protein tyrosine phosphatase alpha in late stage colon carcinomas. Cancer Lett, 1995, 93: 239-48.

Tallman, M.S., Anderson, J.W. Schiffer, C.A., Applebaum, F.R, Feusner, J.H., Ogden, A., Shepherd, L., Rowe, J.M., Francois, C., Larson, R.S. and Wiemik, P.H. Clinical description of 44 patients with acute promyelocytic leukemia who developed the retinoic acid syndrome. Blood, 95: 90-5, 2000.

Tanuma, N., K. Nakamura, H. Shima and K. Kikuchi. Protein-tyrosine phosphatase PTPepsilon C inhibits Jak-STAT signaling and differentiation induced by interleukin-6 and leukemia inhibitory factor in M1 leukemia cells. J Biol Chem, 2000.275: 28216-21.

Taolin, Yi, M.K. Pathak, D.J. Lindner, M.E. Ketterer, C. Farver and E.C. Borden. Anticancer Activity of Sodium Stibogluconate in Synergy with IFNs; The Journal of immunology, 2002, 169: 5978-5985.

Thornassen, M.J., Yi, T., Raychaudhun, B., Malur, A. and Kavuru, M.S. Pulmonary alveolar proteinosis is a disease of decreased availability of GM-CSF rather than an intrinsic cellular defect. Clin Immunol, 95: 85-92, 2000.

Tohda, S., Yang, G.s., Ashman, L.K., McCulloch, E.A. and Minden, M.D. Relationship between c-Kit expression and proliferation in acute myeloblastic leukemia cell lines. J Cell Physiol, 154: 410-8, 1993.

Tonks, N.K. and B.G. Neel. Combinatorial control of the specificity of protein tyrosine phosphatases. Curr Opin Cell Biol, 2001, 13: 182-95.

Trowbridge, I.S. and M.L. Thomas, CD45: an emerging role as a protein tyrosine phosphatase required for lymphocyte activation and development. Ann. Rev. Immunol., 12:85-116, 1994.

Tsui, H.W., Siminovitch, K. A., de Souze, L. and Tsui, F.W. Motheaten and viable motheaten mice have mutations in the haematopoietic cell phosphatase gene. Nature Genetics, 4: 124-9, 1993.

Uddin, S., Grumbach, I.M., Yi, T., Colamnoici, O.R. and Plantanias, L.C. Interferon alpha activates the tyrosine kinase Lyn in haemopoietic cells. Br J Haematol, 101: 446-9, 1998.

van Haelst-Pisani, et al., Cancer, 70:2310-2, 1992.

van Moorselaar, R.J., P. van Stratum, G. Borm, F.M. Debruyne and J.A. Schalken. Differential antiproiiferative activities of alpha- and gamma-interferon and tumor necrosis factor alone or in combinations against two prostate cancer xenografts transplanted in nude mice. Prostate, 1991, 18:331-44.

Wang, C., Cunis, J.E., Minden, M.D. and McCulloch, E.A. Expression of a retinoic acid receptor gene in myeloid leukemia cells. Leukemia, 3: 264-9, 1989.

Wickrema, A., F. chen, F. Namin, T. Yi, S. Ahmad, s. Uddin, Y.H. Chen, L. Feldman, W. Stock, R. Hoffman and L. C. Platanias, Defective expression of the SHP-1 phosphatase in polycythemia vera. Exp Hematol, 1999, 27: 1124-32.

Wu, D.W., Stark, K.C., Dunnington, D., Dillon, S.B., Yi, T., Jones, C. and Pelus, L.M. SH2-Containing protein tyrosine phosphatase-1 (SHP-1) association with Jak2 in UT-7/Epo cells. Blood Cells Mol Dis, 26: 15-24, 2000.

Yang, W., Tabrizi, M., Berrada, K. and Yi, T. SHP-1 C-terminus interacts with novel substrates p32/p30 during Epo and IL-3 mitogenic response. Blood, 91: 3746-3755, 1998.

Yetter, A., Uddin, S., Krolewski, J.J., Jiao, H., Yi, T. And Platanias, L.C. Association of the interferon-dependent tyrosine kinase Tyk-2 with the hematopoietic cell phosphatase. J Biol Chem, 270: 18179-18182, 1995.

Yi, T. and Ihle, J.N. Association of hematopoietic cell phosphatase with c-Kit after stimulation with c-Kit ligand. Molecular & Cellular Biology, 13: 3350-8, 1993.

Yi, T., Cleveland, J.L., Ihle, J.N., Identification of novel protein tyrosine phosphatases of hematopoietic cells by polymerase chain reaction amplification. Blood, 78: 2222-28, 1991.

Yi, T.L., Cleveland, J.L. and Ihle, J.N. Protein tyrosine phosphatase containing SH2 domains: characterization, preferential expression in hematopoietic cells and localization to human chromosome 12p12-p13. Molecular & Cellular Biology, 12: 836-46, 1992.

Yi, T., Gilbert, D.J., Jenkins, N.A., Copeland. N.G. and Ihle, J.N. Assignment of a novel protein tyrosine phosphatase gene (Hcph) to mouse chromosome 6. Genomics, 14: 793-5, 1992.

Yi, T., Mui, A.L., Krystal, G. and Ihle, J.N. Hematopoietic cell phosphatase associates with the interleukin-3 (IL-3) receptor beta chain and down-regulates IL-3-induced tyrosine phosphorylation and mitogenesis. Molecular & Cellular Biology, 13: 7577-86, 1993.

Yi, T., Zhang, J., Miura, O. and Ihle, J.N. Hematopoietic cell phosphatase associates with crythropoietin (Epo) receptor after Epo-induced receptor tyrosine phosphorylation: identification of potential binding sites. Blood, 85: 87-95, 1995.

Yi, T., M.K. Pathak, d.J. Lindner, and E.C. Borden. 200. PtPase Inhibitor Sodium Stibogluconate Inhibits the Growth of Human cancer Cell Lines in Vitro and in Vivo and Synergizes with IFNa/b. Blood, 98(11) 301a, 2001.

Yi, T., M.K. Pathak, d.J. Lindner, M.E. Ketterer, C. Farver, and E.C. Borden. 2002. Anticancer activity of sodium stibogluconate in synergy with IFNs. J Immunol 169: 5978.

Yi, T., M. Pathak, D. Lindner, M. Zhou, K. fan. SHP-1 Protein tyrosine phosphatase as a target molecule in anti-tumor immune therapies: SHP-1 Inhibitor SSG interacts with IL-2 to increase anti-murine renal tumor immunity.

Yoshida, J., N. Shibuya, T. Kobayashi, and N. Kageyama. Sensitivity to 1-(4-amino-2-methyl-5-pyrimidinyl)methyl-3-(2-chloroelhyl)-3-nitrosourea hydrochloride (ACNU) of glioma cells in vivo and in vitro. Cancer, 50: 410-418, 1982.

You, M., D.H. Yu and g.s. Geng. Shp-2 tyrosine phosphatase functions as a negative regulator of the interferon-stimulated Jak/STAT pathway. Mol Cell Biol, 1999, 19: 2416-24.

Zanke, B., Squire, J., Griesser, H., Henry, M., Suzuki, H., Patterson, B., Minden, M. and Mak, T.W. A hematopoietic protein tyrosine phosphatase (HePTP) gene that is amplified and overexpressed in myeloid malignancies maps to chromosome Iq32.1. Leukemia, 8: 236-44, 1994.

Zeng, Q., W. Hong, and Y.H. Tan. Mouse PRL-2 and PRL-3, two potentially prenylated protein tyrosine phosphatases homologous to PRL-1. Biochem. Biophys. Res. Commun., 244: 421-7, 1998.

Zeng, Q., Si, X., Horstmann, H., Xu, Y., Hong, W., Pallen, C.J. Prenylation-dependent Association of Protein-tyrosine Phosphatases PRL-1, -2, and -3 with the Plasma Membrane and the Early Endosome. J. Biol. Chem. 275: 21444-52, 2000.

Zhang, J., Somani, A.K. an dSiminovitch, K.A. Roles of the SHP-1 tyrosine phosphatase in the negative regulation of cell signaling. Semin Immunol, 12: 361-78, 1999.

Zhang, Q., P.N. Raghunath, E. Vonderheid, N. Odum and M.A. Wasik. Lack of phosphotyrosine phosphatase SHP-1 expression in malignant T-cell lymphoma cells results from methylation of the SHP-1 promoter. Am J Pathol., 2000, 157: 1137-46.

Zhang, Y.L., Keng, Y.F., Zhao, Y., Wu, L. and Zhang, Z.Y. Suramin is an active site-directed, reversible, and tight-binding inhibitor of protein-tyrosine phosphatases. J Biol Chem, 273: 12281-7, 1998.

Zhao, Z., Shen, S.H. and Fischer, E.H. Phorbol ester-induced expression, phosphorylation, and translocation of protein-tyrosine-phosphatase in IC in HL-60 cells. Proc Natl Acad Sci USA, 91: 5007-11, 1994.

Baer, H. P. et al. Pentamidine does not interfere with nitrite formation in activated raw 264.7 macrophages but inhibits constitutive brain nitric oxide synthase. Life Sciences, 1995, 57: 1973-1980.

Bailly, C. et al. Sequence-selective binding to DNA of bis(amidinophenoxy)alkanes related to propamidine and pentamidine. Biochem. J., 1997, 323: 23-31.

Berndt, A. et al. Expression of the transmembrane protein tyrosine phosphatase RPTPalpha in human oral squamous cell carcinoma. Histochem. Cell. Biol., 1999, 111:399-403.

Bronner, U. et al. Pentamidine concentrations in plasma, whole blood and cerebrospinal fluid during treatment of *Trypanosoma gambiense* infection in Cote d'Ivoire. Transactions of the Royal Society of Tropical Medicine and Hygiene, 1991, 85: 608-611.

Brown-Shimer, S. et al. Effect of protein tyrosine phosphatase 1B expression on transformation by the human *reu*oncogene. Cancer Research, 1992, 52:478-482.

Carter, David A. Expression of a novel rat protein tyrosine phosphatase gene. Biochimica et Biophysica Acta, 1998, 1442:405-408.

Chiarigi, P. et al. Insight into the role of low molecular weight phosphotyrosine phosphatase (LMW-PTP) on platelet-derived growth factor receptor (PDGF-r) signaling. J. Biol. Chem. 2002, 277 (40):37331-37338.

Clore, C. M. and A. M. Gronenborn. Structures of larger proteins, protein-ligand and protein-DNA complexes by multidimensional heteronuclear NMR. Protein Science, 1994, 3:374-390.

Donkor, I. A. and A. M. Clark. In vitro antimicrobial activity of aromatic diamidines and diitnidazolines related to pentamidine. Eur. J. Med. Chem, 1999, 34:639-643.

Eckstein, Jens W. Cdc25 as a potential target of anticancer agents. Investigational New Drugs, 2000, 18:149-156.

Farinotti, R. et al. Comparison of tissular disposition of pentamidine mesylate in the rat after aerosol or parenteral administration. J. Infect. Dis., 1989, 160:507-512.

Fiaschi, T. et al. Low molecular weight protein-tyrosine phosphatase is involved in growth inhibition during cell differentiation. J. Biol. Chem., 2001, 276:49156-49163.

Holloway, A. F. et al. Regulation of cytokine gene transcription in the immune system. Mol. Iminunol., 2001, 38:567-580.

Jiang, Y et al. Inhibition of anchorage-independent growth and lung metastasis of A549 lung carcinoma cells by I kappa B beta. Oncogene, 2001, 20:2254-2263.

Kikawa, K. D. et al. Regulation of the EphA2 kinase by the low molecular weight tyrosine phosphatase induces transformation. J. Biol. Chem., 2002, 277, 39274-39279.

Kitamura, Y et al. Inhibition of constitutive nitric oxide synthase in the brain by pentamidine, a calmodulin antagonist. Fur. J. Phann., 1995, 289:299-304.

Lakka, S. S. et al. Adenovirus-mediated antisense urokinase-type plasminogen activator receptor gene transfer reduces tumor cell invasion and metastasis in no-small cell lung cancer cell lines. Clinical Cancer Research, 2001, 78:1087-1093.

LaMontagne, Jr., K. R. et al. Protein tyrosine phosphatase 1B antagonizes signalling by oncoprotein tyrosine kinase p210 ber-abl in vitro. Mol. & Cell. Biol., 1998, 18:2965-2975.

Liu, Y. et al. Inhibition of in vitro splicing of a group I intron of *Pneuocystis carinii*. J. Euk. Microbial., 1994, 41:31-38.

Liu, J. et al. Mediation of the DCC apoptotic signal by DIP13 alpha. J. Bio. Chem., 2002, 277:26281.

Murray, H. W. et al. Treatment of experimental visceral Leishmaniasis in a T-cell-deficient host: response to Amphotericin B and pentamidine. Antimicrobial Agents and Chemotherapy, 1993, 37: 1504.

Myers, M. P. et al. TYK2 and JAK2 are substrates of protein-tyrosine phosphatase 1B. J. Biol. Chem, 2001, 276:47771-47774.

Nagatsuka, I, et al. Inhibitory effect of a selective cyclooxygenase-2 inhibitor on liver metastasis of colon cancer. Int. J. Cancer, 2002, 100:515-519.

Nilsson, I and I. Hoffmann. Cell cycle regulation by the Cdc25 phophatase family. Progress in Cell Cycle Research, 200, 4:107-114.

Pallen, C. J. The receptor-like protein tyrosine phosphatase alpha: a role in cell proliferation and oncogenesis. Cell Biology, 1998:4:403-408.

Parsons, R. Phosphatases and tumorigenesis. Current Opinion in Oncology 1998, 10:88-91.

Pathak, M. K. et al. Pentamidine is an in hibitor of PRL phophatases with anticancer activity. Molecular Cancer Therapeutics, 2002, 1:1255.

Pathak, M. K. Sodium stibogluconate anti-cancer activity: targeting PRL family PTPase. (submitted for publication).

Patrick, D. A. Synthesis and anti-*Pneumocystis carinii* pneumonia activity of novel dicationic and dibenzothiophenes and orally active prodrugs. cur. J. Med. Chem., 1999, 34, 575.

Ramesh, R. et al. Successful treatment of primary and disseminated human lung cancers by systemic delivery of tumor suppressor genes using an improved liposome vector. Molecular Therapy, 2001, 3:337-350.

Sands, M. et al. Pentamidine: a Review. Reviews of Infectious Diseases, 1985, 7:625-634.

Shen, K. et al. Acquisition of a specific and potent PTP1B inhibitor from a novel combinatorial library and screening procedure. J. Biol. Chem. 2011, 276:47311-47319.

Si, X. et al. Interaction of Famesylated PRL-2, a protein-tyrosine phosphatase, with the beta-subunit of geranylgeranyltransferase II. J. Biol. Chem. 2001, 276:32875-32882.

Sun, H. et al. Inhibition of Ras induced DNA synthesis by expression of the phosphatase MKP-1. Science, New Series, 1994, 266:285-288.

Tabrizi, M. et at. reduced Tyk2/SHP-1 interaction and lack of SHP-1 mutation in a hundred of familial hemophagocytic lymphohistiocytosis. Leukemia, 1998, 12:200-206.

Tbakhi, A. et al. Fixation conditions for DNA and RNA in situ hybridization: a reassessment of molecular morphology dogma. Am. J. Pathol., 1998, 152:35-41.

Tidwell, R. R. et al. Development of pentamidine analogues as new agents for the treatment of *Pneumocystis carinii* pneumonia. Annals NY Acad. Sci., 1990, 616:421-441.

Wang, Q. et al. Analysis of stromal-epithelial interactions in prostate cancer identifies PTPCAAX2 as a potential oncogene. Cancer Letters, 2002, 175:63-69.

Wolf, N. G. et al. Analysis of ovarian borderline tumors using comparative genomic hybridization and fluorescence in situ hybridization. Genes, Chromosomes & Cancer, 1999, 25:307-315.

Wu, H-C. et al. Derivation of androgen-independent human LNCaP prostatic cancer cell subtitles: role of bone stromal cells. Int. J. Cancer, 1994, 57, 406-412.

Yamazaki, T. et al. Secondary structure and signal assignments of human-immunodeficiency-virus-1 protease complexed to a novel, structure-based inhibitor. Eur. J. Biochem., 1994, 219:707-712.

Yang, W. et al. SHP-1 deficiency in B-lineage cells is associated with heightened lyn protein expression and increased lyn kinase activity. Experimental Hematology, 1998, 26:1126-1132.

Yi, Taolin et al. Anti-cancer activity of sodium stibogluconate in synergy with IFNs: inhibition of PRL phosphatases. (submitted for publication).

Zhang, Zhong-Yin. Protein tyrosine phosphatases: prospects for therapeutics. Current Opinion in Chemical Biology 2001. 5:416-423.

Zhang, Zhong-Yin. Protein tyrosine phosphases: structure and function, substrate specificity, and inhibitor development. Ann. Rev. Pharmacol. Tex. Col., 2002, 42:209-235.

A.

B.

THERAPEUTIC COMPOSITIONS AND METHODS USEFUL IN MODULATING PROTEIN TYROSINE PHOSPHATASES

CROSS-REFERENCE TO RELATED APPLICATIONS

This application claims the benefit of U.S. Provisional Application No. 60/317,993 filed Sep. 7, 2001.

BACKGROUND OF THE INVENTION

Intercellular protein tyrosine phosphorylation is regulated by extracellular stimuli, such as cytokines, to control cell growth, differentiation and functional activities. This signaling mechanism depends on the interplay of protein tyrosine kinases, which initiate signaling cascades through phosphorylating tyrosine residues in protein substrates, and by protein tyrosine phosphatases that terminate signaling via substrate dephosphorylation. Chemical compounds that modulate the activity of protein tyrosine kinases or phosphatases can induce cellular changes through affecting the balance of intracellular protein tyrosine phosphorylation and redirecting signaling. Such compounds can be of value as experimental tools and, importantly, as potent therapeutic reagents.

So far, few specific inhibitors of protein tyrosine phosphatases have been reported despite extensive efforts in the last decade to identify them. Although a number of chemicals that broadly inhibit protein tyrosine phosphatases are known, including sodium orthovanadate and iodoacetic acid, their usefulness as therapeutic agents is severely limited due to their general toxicity in vivo. Recently, it has been reported that Suramin, a polysulfonated naphthylurea compound, can act in vitro as a competitive and reversible inhibitor of several protein tyrosine phosphatases. Such an inhibitory activity of Suramin against protein tyrosine phosphatases is consistent with its activity in augmenting tyrosine phosphorylation of cellular proteins and may explain its antitumor activity and its therapeutic effect in treating trypanosomiasis and onchocerciasis.

SUMMARY OF THE INVENTION

As used herein, the following abbreviations have the following meanings:

"AML" is used herein to mean acute myeloid leukemia;
"ATRA" is used herein to mean All-trans-retinoic acid;
"GM-CSF" is used herein to mean granulocyte/macrophage colony stimulating factor;
"IFNα" is used herein to mean interferon α;
"IFNβ" is used herein to mean interferon β;
"IL-3" is used herein to mean interleukine-3;
"Jak2" is used herein to mean janus family kinase 2;
"NBT" is used herein to mean, nitroblue tetrazolium;
"PTPase" is used herein to mean protein tyrosine phosphatase;
"PTK" is used herein to mean protein tyrosine kinase
"SH2 is used herein to mean Src-homology 2 domain;
"SHP-1" is used herein to mean Src-homology protein tyrosine phosphatase;
"Stat5" is used herein to mean signal transducer and activator of transcription 5;
"SS" is used herein to mean, Sodium stibogluconate One embodiment of the present invention provides for a therapeutic composition containing a pentavalent antimonial. The pentavalent antimonial can be sodium stibogluconate, levamisole, ketoconazole, and pentamidine and biological equivalents of said compounds. Additionally, pentavalent antimonials that can be used in accordance with the present invention may be any such compounds which are anti-leishmaniasis agents. The therapeutic composition of this embodiment contains an effective amount of pentavalent antimonial that can be used in treating infectious diseases. The types of diseases that can be treated with the present invention include, but are not limited to, the following: diseases associated with PTPase activity, immune deficiency, cancer, infections (such as viral infections), hepatitis B, and hepatitis C. The types of cancers that the present embodiment can be used to treat include those such as lymphoma, multiple myeloma, leukemia, melanoma, prostate cancer, breast cancer, renal cancer, bladder cancer. The therapeutic composition enhances cytokine activity. The therapeutic composition may include a cytokine, such as interferon α, interferon β, interferon γ, or granulocyte/macrophage colony stimulating factor.

Another embodiment of the present invention provides for a therapeutic composition composed of an anti-leishmaniasis agent. The potential anti-leishmaniasis agents that may be used in accordance with the present embodiment include sodium stibogluconate, levamisole, ketoconazole, pentamidine and biological equivalents of such compounds. The therapeutic composition of this embodiment contains an effective amount of the anti-leishmaniasis agent that can be used in treating infectious diseases. The types of diseases that can be treated with the present invention include, but are not limited to, the following: diseases associated with PTPase activity, immune deficiency, cancer, infections (such as viral infections), hepatitis B, and hepatitis C. The types of cancers that the present embodiment can be used to treat include those such as lymphoma, multiple myeloma, leukemia, melanoma, prostate cancer, breast cancer, renal cancer, bladder cancer. The therapeutic composition enhances cytokine activity. The therapeutic composition may include a cytokine, such as interferon α, interferon β, interferon γ, or granulocyte/macrophage colony stimulating factor.

Another embodiment of the present invention provides for a composition including a pentavalent antimonial and a cytokine. The pentavalent antimonial can be sodium stibogluconate, levamisole, ketoconazole, and pentamidine and biological equivalents of said compounds. Additionally, pentavalent antimonials that can be used in accordance with the present invention may be any such compounds which are anti-leishmaniasis agents. The composition of this embodiment contains an effective amount of pentavalent antimonial that can be used in treating infectious diseases. The types of diseases that can be treated with the present invention include, but are not limited to, the following: diseases associated with PTPase activity, immune deficiency, cancer, infections (such as viral infections), hepatitis B, and hepatitis C. The types of cancers that the present embodiment can be used to treat include those such as lymphoma, multiple myeloma, leukemia, melanoma, prostate cancer, breast cancer, renal cancer, bladder cancer. The composition enhances cytokine activity, and may include a cytokine, such as interferon α, interferon β, interferon γ, or granulocyte/macrophage colony stimulating factor.

Another embodiment of the present invention provides for a therapeutic mixture including a pentavalent antimonial and a cytokine. The pentavalent antimonial can be sodium stibogluconate, levamisole, ketoconazole, and pentamidine and biological equivalents of said compounds. Additionally, pentavalent antimonials that can be used in accordance with the present invention may be any such compounds which are anti-leishmaniasis agents. The therapeutic mixture of this embodiment contains an effective amount of pentavalent antimonial that can be used in treating infectious diseases. The types of diseases that can be treated with the present invention include, but are not limited to, the following: diseases associated with PTPase activity, immune deficiency, cancer, infections (such as viral infections), hepatitis B, and hepatitis C. The types of cancers that the present embodiment can be used to treat include those such as lymphoma, multiple myeloma, leukemia, melanoma, prostate cancer, breast cancer, renal cancer, bladder cancer. The therapeutic mixture enhances cytokine activity. The therapeutic mixture may include a cytokine, such as interferon α, interferon β, interferon γ, or granulocyte/macrophage colony stimulating factor.

Another embodiment of the present invention provides for a therapeutic mixture composed of an anti-leishmaniasis agent and a cytokine. The potential anti-leishmaniasis agents that may be used in accordance with the present embodiment include sodium stibogluconate, levamisole, ketoconazole, pentamidine and biological equivalents of such compounds. The therapeutic mixture of this embodiment contains an effective amount of the anti-leishmaniasis agent that can be used in treating infectious diseases. The types of diseases that can be treated with the present invention include, but are not limited to, the following: diseases associated with PTPase activity, immune deficiency, cancer, infections (such as viral infections), hepatitis B, and hepatitis C. The types of cancers that the present embodiment can be used to treat include those such as lymphoma, multiple myeloma, leukemia, melanoma, prostate cancer, breast cancer, renal cancer, bladder cancer. The therapeutic mixture enhances cytokine activity. The therapeutic mixture may include a cytokine, such as interferon α, interferon β, interferon γ, or granulocyte/macrophage colony stimulating factor.

Another embodiment of the present invention provides for a method of treating a patient by administering a pentavalent antimonial. The pentavalent antimonial that may be used in accordance with the present embodiment include sodium stibogluconate, levamisole, ketoconazole, pentamidine and biological equivalents of such compounds. This embodiment of the present invention can be used to treat a patient who suffers from a disease state, such as cancer, infection (such as a viral infection), immune deficiency, hepatitis B, hepatitis C, a disease associated with PTPase activity. This embodiment provides for the administering of a cytokine in connection with the pentavalent antimonial, such as the cytokines such as interferon α, interferon β, interferon γ, or granulocyte/macrophage colony stimulating factor.

Another embodiment of the present invention provides for a method of treating a patient by administering an anti-leishmaniasis agent. The anti-leishmaniasis agent may be a pentavalent antimonial, such as sodium stibogluconate, levamisole, ketoconazole, pentamidine and biological equivalents of such compounds. This embodiment of the present invention can be used to treat a patient who suffers from a disease state, such as cancer, infection (such as a viral infection), immune deficiency, hepatitis B, hepatitis C, a disease associated with PTPase activity. This embodiment provides for the administering of a cytokine in connection with anti-leishmaniasis agent, such as interferon α, interferon β, interferon γ, or granulocyte/macrophage colony stimulating factor.

Another embodiment of the present invention provides for a method of increasing cytokine activity administering an anti-leishmaniasis agent. The anti-leishmaniasis agent may be a pentavalent antimonial, such as sodium stibogluconate, levamisole, ketoconazole, pentamidine and biological equivalents of such compounds. This embodiment of the present invention can be used to treat a patient who suffers from a disease state, such as cancer, infection (such as a viral infection), immune deficiency, hepatitis B, hepatitis C, a disease associated with PTPase activity. This embodiment provides for the administering of a cytokine in connection with anti-leishmaniasis agent, such as interferon α, interferon β, interferon γ, or granulocyte/macrophage colony stimulating factor.

BRIEF DESCRIPTION OF THE DRAWINGS

FIG. 20A-C illustrates chemical structure for three pentavalent antimony agents.

FIG. 21A-C illustrate the inhibition of PTPase activity with regard to Levamisole, Ketoconazole, and Pentamidine with Sodium Stibogluconate serving as a model agent. Levamisole, Pentamidine and Ketoconazole inhibits the activity of PTP1B in vitro.

FIG. 22 illustrates the effect of SS, IFNα both on the growth of xenografts of human melanoma cell line WM9 and human prostata carcinoma cell line DU-145 in athymic nude mice. Nude mice of 4 weeks old were inoculated subcutaneously (s.c.) with WM9 human melanoma cell (3×106 cells/site) (A) or DU-145 human prostate cancer cells (2×106 cells/site) (B) on day 0, Starting on day 2, the mice were subjected to no treatment (control) or treatment with IFNα (500,000 U, s.c., daily), SS (12 mg, s.c., daily) or both (combo). Tumor volume in the nude mice (4 mice/group, 2 tumors/mouse) was measured on the days as indicated. Tumor volume was calculated by the equation (length× width$^2$)/2 to compare tumor growth rates. All mice survived by the end of the experiment. The data present mean±SEM of 8 tumors (2 tumors/mouse).

FIG. 23. Illustrates body weights of nude mice bearing WM9 xenografts and subjected to no treatment (Control) or treated with the combination of SS (12 mg Sb, s.c., daily) and IFNα (500,000 U, s.c., daily) for 23 days were measured once weekly. Data represent the mean±SEM of four mice.

DETAILED DESCRIPTION

Figure 1:
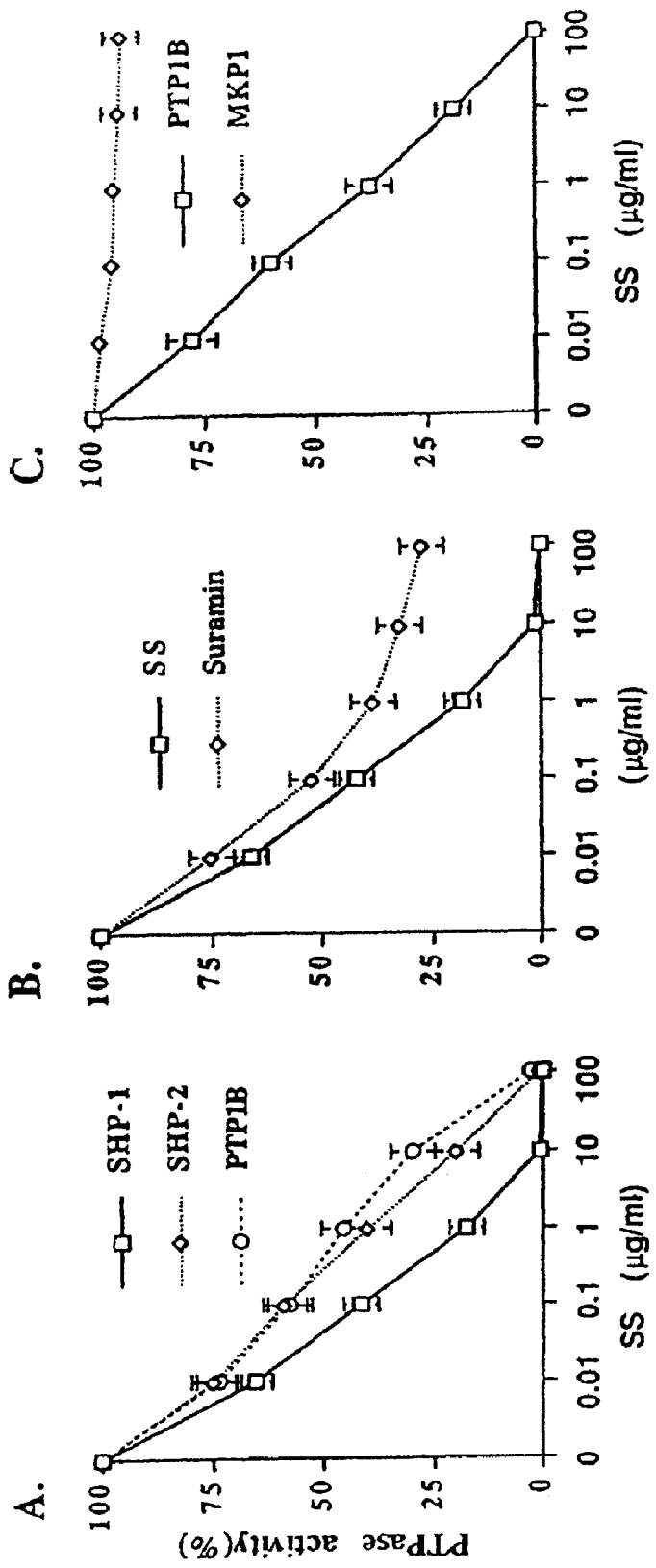
FIG. 1. Sodium stibogluconate inhibits PTPases in vitro. A. Relative PTPase activities of GST fusion proteins of SHP-1, SHP-2 and PTP1B in the presence of various amounts of sodium stibogluconate (SS). B. Relative PTPase activities of GST/SHP-1 fusion protein in the presence of various amounts of SS or Suramin. C. Relative PTPase activities of GST fusion proteins of PTP1B and MKP1 in the presence of various amounts of SS. The data represent the mean±SD values of triplicate samples measured by in vitro PTPase assays.

Disclosed herein are compositions and methods useful in modulating the activity of protein tyrosine phosphorylation. Protein tyrosine kinases initiate signaling cascades through phosphorylating tyrosine residues in protein substrates, and by protein tyrosine phosphatases that terminate signaling via substrate dephosphorylation. Chemical compounds that modulate the activity of protein tyrosine kinases or phosphatases can induce cellular changes through affecting the balance of intracellular protein tyrosine phosphorylation and redirecting signaling.

Sodium stibogluconate (also known as sodium antimony gluconate, Stibanate, Dibanate, Stihek, Solustibostam, Solyusurmin, Pentostam or Glucantime), a pentavalent antimonial used for the treatment of leishmaniasis, is disclosed herein as a potent inhibitor of protein tyrosine phosphatases. SHP-1 phosphatase activity was substantially inhibited by the drug at a concentration less than or equal to the peak serum level obtained in human beings treated for leishmaniasis. Based on this observation, a number of other agents were analyzed for their inhibition on phospatases. These agents generally are either pentavalent antimonial or agents effective in treating leishmaniasis. Thus, the present invention is predicated on the discovery that sodium stibogluconate is an inhibitor of protein tyrosine phosphatase(s), however, it is not to be so limited.

Accordingly, an embodiment of the present invention provides for a method for the prophylactic and therapeutic treatment of diseases associated with protein tyrosine activity or abnormal activity thereof. By "prophylactic", it is meant the protection, in whole or in part, against a particular disease or a plurality of diseases. By "therapeutic", it is meant the amelioration of the disease itself, and the protection, in whole or in part, against further disease. The method comprises the administration of an inhibitor of protein tyrosine phosphatase in an amount sufficient to treat a subject either prophylactically or therapeutically. Sodium stibogluconate as used herein includes all biochemical equivalents (i.e. salts, precursors, and its basic form). "To mix", "mixing", or "mixture(s)" as used herein means mixing a substrate and an agonist: 1) prior to administration ("in vitro mixing"); 2) mixing by simultaneous and/or consecutive, but separate (i.e. separate intravenous lines) administration of substrate and agonist (angiogenic growth factor) to cause "in vivo mixing".

Preferably, the agent is a pharmaceutically acceptable analogue or prodrug thereof or a pharmaceutically acceptable salt of the agents or drugs disclosed herein which are effective in inhibiting protein tyrosine phosphotases. One of ordinary skill in the art will appreciate that the prodrug used must be one that can be converted to an active agent in or around the site to be treated.

The active agents described herein, as well as their biological equivalents or pharmaceutically acceptable salt of the foregoing can be administered in accordance with the present inventive method by any suitable route. Suitable routes of administration include systemic, such as orally or by injection, topical, intraocular, periocular, subconjunctival, subretinal, suprachoroidal and retrobulbar. The manner in which the agent is administered is dependent, in part, upon whether the treatment is prophylactic or therapeutic.

The composition(s) of the present invention is preferably administered as soon as possible after it has been determined that an animal, such as a mammal, specifically a human, is at risk for a disease associated with protein tyrosine phosphatase activity. Treatment will depend, in part, upon the particular therapeutic composition used, the amount of the therapeutic composition administered, the route of administration, and the cause and extent, if any, of the disease One skilled in the art will appreciate that suitable methods of administering the therapeutic composition useful in the present inventive method, are available. Although more than one route can be used to administer a particular therapeutic composition, a particular route can provide a more immediate and more effective reaction than another route. Accordingly, the described routes of administration are merely exemplary and are in no way limiting.

The dose administered to an animal, particularly a human, in accordance with the present invention should be sufficient to effect the desired response in the animal over a reasonable time frame. One skilled in the art will recognize that dosage will depend upon a variety of factors, including the strength of the particular therapeutic composition employed, the age, species, condition or disease state, and body weight of the animal. The size of the dose also will be determined by the route, timing and frequency of administration as well as the existence, nature, and extent of any adverse side effects that might accompany the administration of a particular therapeutic composition and the desired physiological effect. It will be appreciated by one of ordinary skill in the art that various conditions or disease states, in particular, chronic conditions or disease states, may require prolonged treatment involving multiple administrations.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached.

The administration(s) may take place by any suitable technique, including oral, subcutaneous and parenteral administration, preferably parenteral or oral. Examples of parenteral administration include intravenous, intra-arterial, intramuscular, and intraperitoneal. The dose and dosage regimen will depend mainly on whether the inhibitors are being administered for therapeutic or prophylactic purposes, separately or as a mixture, the type of biological damage and host, the history of the host, and the type of inhibitors or biologically active agent. The amount must be effective to achieve an enhanced therapeutic index. It is noted that humans are generally treated longer than the mice and rats with a length proportional to the length of the disease process and drug effectiveness. The doses may be single doses or multiple doses over a period of several days. Therapeutic purposes is achieved as defined herein is when the treated hosts exhibit improvement against disease or infection, including but not limited to improved survival rate, more rapid recovery, or improvement or elimination of symptoms. If multiple doses are employed, as preferred, the frequency of administration will depend, for example, on the type of host and type of cancer, dosage amounts, etc. The practitioner may need to ascertain upon routine experimentation which route of administration and frequency of administration are most effective in any particular case.

Compositions for use in the present inventive method preferably comprise a pharmaceutically acceptable carrier and an amount of the therapeutic composition sufficient to treat the particular disease prophylactically or therapeutically. The carrier can be any of those conventionally used and is limited only by chemico-physical considerations, such as solubility and lack of reactivity with the compound, and by the route of administration. It will be appreciated by one of ordinary skill in the art that, in addition to the following described pharmaceutical compositions, the therapeutic composition can be formulated as polymeric compositions, inclusion complexes, such as cyclodextrin inclusion complexes, liposomes, microspheres, microcapsules and the like (see, e.g., U.S. Pat. Nos. 4,997,652, 5,185,152 and 5,718,922).

The therapeutic composition can be formulated as a pharmaceutically acceptable acid addition salt. Examples of pharmaceutically acceptable acid addition salts for use in the pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, and arylsulphonic, for example p-toluenesulphonic, acids.

The pharmaceutically acceptable excipients described herein, for example, vehicles, adjuvants, carriers or diluents, are well-known to those who are skilled in the art and are readily available to the public. It is preferred that the pharmaceutically acceptable carrier be one which is chemically inert to the therapeutic composition and one which has no detrimental side effects or toxicity under the conditions of use.

The choice of excipient will be determined in part by the particular therapeutic composition, as well as by the particular method used to administer the composition. Accordingly, there is a wide variety of suitable formulations of the pharmaceutical composition of the present invention. The following formulations are merely exemplary and are in no way limiting.

Injectable formulations are among those that are preferred in accordance with the present inventive method. The requirements for effective pharmaceutically carriers for injectable compositions are well-known to those of ordinary skill in the art (see Pharmaceutics and Pharmacy Practice, J. B. Lippincott Co., Philadelphia, Pa., Banker and Chalmers, eds., pages 238-250 (1982), and ASHP Handbook on Injectable Drugs, Toissel, 4th ed., pages 622-630 (1986)). It is preferred that such injectable compositions be administered intramuscularly, intravenously, or intraperitoneally.

Topical formulations are well-known to those of skill in the art. Such formulations are suitable in the context of the present invention for application to the skin. The use of patches, corneal shields (see, e.g., U.S. Pat. No. 5,185,152), and ophthalmic solutions (see, e.g., U.S. Pat. No. 5,710,182) and ointments, e.g., eye drops, is also within the skill in the art.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inhibitor can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride, with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants. Oils, which can be used in parenteral formulations include petroleum, animal, vegetable, or synthetic oils. Specific examples of oils include peanut, soybean, sesame, cottonseed, corn, olive, petrolatum, and mineral.

Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metals, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-p-aminopropionates, and 2-alkyl-imidazoline quaternary ammonium salts, and (e) mixtures thereof. The parenteral formulations will typically contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The present inventive method also can involve the co-administration of other pharmaceutically active compounds. By "co-administration" is meant administration before, concurrently with, e.g., in combination with the therapeutic composition in the same formulation or in separate formulations, or after administration of a therapeutic composition as described above. For example, corticosteroids, e.g., prednisone, methylprednisolone, dexamethasone, or triamcinalone acetinide, or noncorticosteroid anti-inflammatory compounds, such as ibuprofen or flubiproben, can be co-administered. Similarly, vitamins and minerals, e.g., zinc, anti-oxidants, e.g., carotenoids (such as a xanthophyll carotenoid like zeaxanthin or lutein), and micronutrients can be co-administered. In addition, other types of inhibitors of the protein tyrosine phosphotase pathway.

The following examples, materials, methods, discussion, and detailed description are meant to further illustrates the present invention but, of course, should not be construed as in any way limiting its scope.

Sodium Stibogluconate is a Potent Inhibitor of Protein Tyrosine Phosphatases and Augments Cytokine Responses in Hematopoietic Cell Lines Using in vitro PTPase assays, sodium stibogluconate was identified as a potent inhibitor of PTPases SHP-1, SHP-2 and PTP1B but not the dual specificity phosphatase MKP1. Sodium stibogluconate inhibited 99% of SHP-1 activity at 10 µg/ml, a therapeutic concentration of the drug for leishmaniasis. Similar degrees of inhibition of SHP-2 and PTP1B required 100 µg/ml of sodium stibogluconate, demonstrating differential sensitivities of PTPases to the inhibitor. The drug appeared to target the SHP-1 PTPase domain as it showed similar in vitro inhibition of SHP-1 and a mutant protein containing the SHP-1 PTPase domain alone. Moreover, it forms a stable complex with the PTPase: in vitro inhibition of SHP-1 by the drug was not removed by a washing process effective in relieving the inhibition of SHP-1 by the reversible inhibitor Suramin. The inhibition of cellular PTPases by the drug was suggested by its rapid induction of tyrosine phosphorylation of cellular proteins in Baf3 cells and its augmentation of IL-3-induced Jak2/Stat5 tyrosine phosphorylation and proliferation of Baf3 cells. The augmentation of the opposite effects of GM-CSF and IFNα on TF1 cell growth by the drug indicated its broad activities in the signaling of various cytokines.

Intercellular protein tyrosine phosphorylation is regulated by extracellular stimuli, such as cytokines, to control cell growth, differentiation and functional activities. This signaling mechanism depends on the interplay of protein tyrosine kinases, which initiate signaling cascades through phosphorylating tyrosine residues in protein substrates, and by protein tyrosine phosphatases that terminate signaling via substrate dephosphorylation. Chemical compounds that modulate the activity of protein tyrosine kinases or phosphatases can induce cellular changes through affecting the balance of intracellular protein tyrosine phosphorylation and redirecting signaling.

Few specific inhibitors of protein tyrosine phosphatases have been reported despite extensive efforts in the last decade to identify them. Although a number of chemicals that broadly inhibit protein tyrosine phosphatases are known, including sodium orthovanadate and iodoacetic acid, their usefulness as therapeutic agents is severely limited due to their general toxicity in vivo. Recently, it has been reported that Suramin, a polysulfonated naphthylurea compound, can act in vitro as a competitive and reversible inhibitor of several protein tyrosine phosphatases. Such an inhibitory activity of Suramin against protein tyrosine phosphatases is consistent with its activity in augmenting tyrosine phosphorylation of cellular proteins and may explain its antitumor activity and its therapeutic effect in treating trypanosomiasis and onchocerciasis.

SHP-1 is protein tyrosine phosphatase that plays a pivotal role in down regulating signaling in hematopoietic cells. Deficiency of the phosphatase due to mutations in the SHP-1 gene associates with heightened signaling in hematopoietic cells and leads to hyperresponsiveness of hematopoietic cells to a variety of extracellular stimuli, including cytokines, hematopoeitic growth factors and antigens. Thus drugs targeting the enzyme may effectively modulate activation, proliferation and immune responses of hematopoietic cells for therapeutic purposes.

We have screened chemical reagents by in vitro phosphatase assays to identify inhibitors of the SHP-1 phosphatase. Here we report that sodium stibogluconate (also known as sodium antimony gluconate, Stibanate, Dibanate, Stihek, Solustibostam, Solyusurmin, Pentostam or Glucantime), a pentavalent antimonial used for the treatment of leishmaniasis, is a potent in vitro inhibitor of protein tyrosine phosphatases, including SHP-1. The SHP-1 phosphatase activity in vitro was almost completely inhibited by the drug at 10 µg/ml, a concentration less than or equal to the peak serum level obtained in human beings treated for leishmaniasis. The inhibitory activity of the drug against PTPases in vivo was indicated by its enhancement of tyrosine phosphorylation of distinct cellular proteins in Baf3 cells and by its augmentation of Baf3 proliferation induced by the hematopoietic growth factor IL-3. Importantly, we demonstrated that sodium stibogluconate augmented the opposite effects of GM-CSF and IFNα on TF-1 cell growth, suggesting broad activities of the drug in enhancing the signaling of various cytokines. These data provide novel insights into the pharmacological mechanism of sodium stibogluconate and suggest new therapeutic applications.

METHODS: Chemicals and reagents. Protein tyrosine phosphatase assay kits and GST fusion protein of protein tyrosine phosphatase 1B (PTPIB) were purchased from Upstate Biotechnology Inc. (UBI, Lake Placid, N.Y.). Suramin and potassium antimonyl tartrate was purchased from Sigma (St. Louis, Mo.). Sodium stibogluconate (its Sb content is 100 mg/ml and used to designate SS concentration hereafter) was a gift from Dr. Xiaosu Hu (Sichuan Medical College, China). GST fusion proteins of SHP-1 and SHP-2 have been described previously and were prepared following established protocols. The GST fusion protein of SHP-1 cata was purified from DH5a bacteria transformed with a pGEX construct containing the coding region of the PTPase catalytic domain (amino acid 202 to 554) of murine SHP-1, derived by PCR from the murine SHP-1 cDNA. The GST fusion protein of MKP1 was purified from DH5a bacteria transformed with a pGEX construct containing the coding region of MKP1 cDNA derived by RT-PCR using the following primers (MKP1/5, 5'ctggatcctgcgggggctgctgcaggagcgc (SEQ ID NO: 1); MKP1/3, 5'aagtcgacgcagcttggggaggtggtgat (SEQ ID NO: 2)).

Murine IL-3, recombinant human GM-CSF and recombinant human IFNα have been described previously. Antibodies against phosphotyrosine (anti-ptyr, 4G10, UBI), β-actin (Amersham, Arlington Heights, Ill.), phosphotyrosine Stat5 (New England BioLab Inc, Beverly, Mass.) and Jak2 (Affinity BioReagents, Inc., Golden, Colo.) were purchased from commercial sources.

In vitro protein tyrosine phosphatase assays. In vitro PTPase activities were measured using the commercial protein tyrosine phosphatase assay kit (UBI) following established procedure. This assay measures the in vitro dephosphorylation of a synthetic phosphotyrosine peptide (R-R-L-I-E-D-A-E-pY-A-A-R-G (SEQ ID NO: 3)). Briefly, 0.01 μg of GST/PTPase fusion proteins was incubated in 50 μl of Tris buffer (10 mM Tris, pH 7.4) containing different concentrations of inhibitors or chemicals (0 to 1,000 μg/ml) at 22° C. for 10 minutes, followed by addition of 0.2 mM of the phosphotyrosine peptide and incubation at 22° C. for 18 hours. 100 μl of Malachite Green solution was added and incubated for 5 minutes, and the absorbance at 660 nm was measured after 5 minutes.

To assess the reversibility of inhibition of SHP-1 by PTPase inhibitors, GST/SHP-1 fusion protein bound on glutathione beads were pre-incubated in cold Tris buffer or Tris buffer containing the PTPase inhibitors at 4° C. for 30 minutes. The beads were then washed 3 times in Tris buffer or without washing prior to in vitro PTPase assays.

Cells, cell culture and cell proliferation assays. The murine hematopoietic cell line Baf3 was maintained in RPMI 1640 medium supplemented with 10% fetal calf serum (FCS) and murine IL-3 (20 units/ml) as described previously. Human myeloid cell line TF-1 was maintained in RPMI 1640 supplemented with 10% FCS and 40 ng/ml of recombinant human GM-CSF as described previously. For cell proliferation assays, cells were washed in 10% FCS medium twice, resuspended in 10% FCS medium, incubated at 37° C. for 16 hours and then cultured at 37° C. in 10% FCS medium containing various amounts of cytokines, sodium stibogluconate or potassium antimonyl tartrate for 3-6 days as indicated. The cell numbers in proliferation assays were determined by an MTT assay or by microscopic cell counting as indicated.

Induction of cellular protein phosphorylation and Western blotting. For induction of cellular protein phosphorylation by sodium stibogluconate or pervanadate, Baf3 cells were incubated in 0.1% FCS RPMI 1640 medium at 37° C. for 16 hours. The cells were then washed twice in RPMI 1640 medium and incubated with sodium stibogluconate or pervanandate (0.1 mM) for various times prior to termination by lysing cells in cold lysis buffer (50 mM Tris, pH 7.4; 150 mM NaCl; 0.2 mM Na3VO4; 20 mm NaF; 1% NP40; 2 mM PMSF; 20 μg/ml of Aprotinin and 1 mM of sodium molybdic acid). To determine the effect of sodium stibogluconate or potassium antimonyl tartrate on IL-3-induced Jak/Stat phosphorylation, Baf3 cells were deprived of the growth factor for 16 hours in 0.1% FCS RPMI 1640 medium and then incubated with or without sodium stibogluconate or potassium antimonyl tartrate for 10 minutes. IL-3 was next added to the cell suspension and incubated for various times. The Cells were then harvested and lysed in cold lysis buffer at 4° C. for 45 minutes. Total cell lysates (TCL) were separated in SDS-PAGE gels, blotted onto nitrocellulose membrane (Schleicher & Schuell), probed with specific antibodies and detected using an enhanced chemiluminescence kit (ECL, Amersham).

Results

Sodium stibogluconate inhibits protein tyrosine phosphatases in vitro. Through screening various chemical compounds by in vitro PTPase assays, we identified sodium stibogluconate as an inhibitor of PTPases. The dephosphorylation of a synthetic phosphotyrosine peptide by the GST/SHP-1 fusion protein was almost completely blocked (99%) by sodium stibogluconate at 10 μg/ml (FIG. 1A). Sodium stibogluconate also inhibited SHP-2 and PTP1B (FIG. 1A). However, approximately 10 fold higher concentrations of the drug (100 μg/ml) were required to achieve a similar degree (about 99%) of inhibition of the two PTPases (FIG. 1A). Inhibition of SHP-1 by the known PTPase inhibitor Suramin was less effective under comparable conditions (FIG. 1B). The drug showed no obvious inhibitory activity against MKP1, a dual-specificity protein tyrosine phosphatase (FIG. 1C). Under the experimental conditions, the GST fusion proteins of SHP-1, SHP-2, PTP1B and MKP1 showed similar PTPase activities against the peptide substrate (OD 660 nm absorbance approximately 0.6 above background (0.03)) in the absence of inhibitors.

Sodium stibogluconate targets the SHP-1 PTPase catalytic domain and forms stable complexes with the phosphatase in vitro. Substrate dephosphorylation is mediated by the PTPase catalytic domain, the activity of which is often regulated by flanking N-terminal and C-terminal regions. To define whether sodium stibogluconate inhibits PTPases through targeting the PTPase catalytic domain or via the flanking regulatory regions, we compared the effect of sodium stibogluconate on the GST/SHP-1 fusion protein and the GST/SHP-1cata fusion protein which contains the PTPase catalytic domain but has the SH2 domains and the C-terminal region deleted (FIG. 2A). Sodium stibogluconate showed similar activities in inhibiting the two proteins in their dephosphorylation of the phosphotyrosine peptide substrate in vitro (FIG. 2B), demonstrating that inhibition of SHP-1 PTPase activity by sodium stibogluconate does not require the SHP-1 SH2 domains and the C-terminal region. These results provide strong evidence that sodium stibogluconate directly targets the SHP-1 PTPase catalytic domain.

Figure 3:
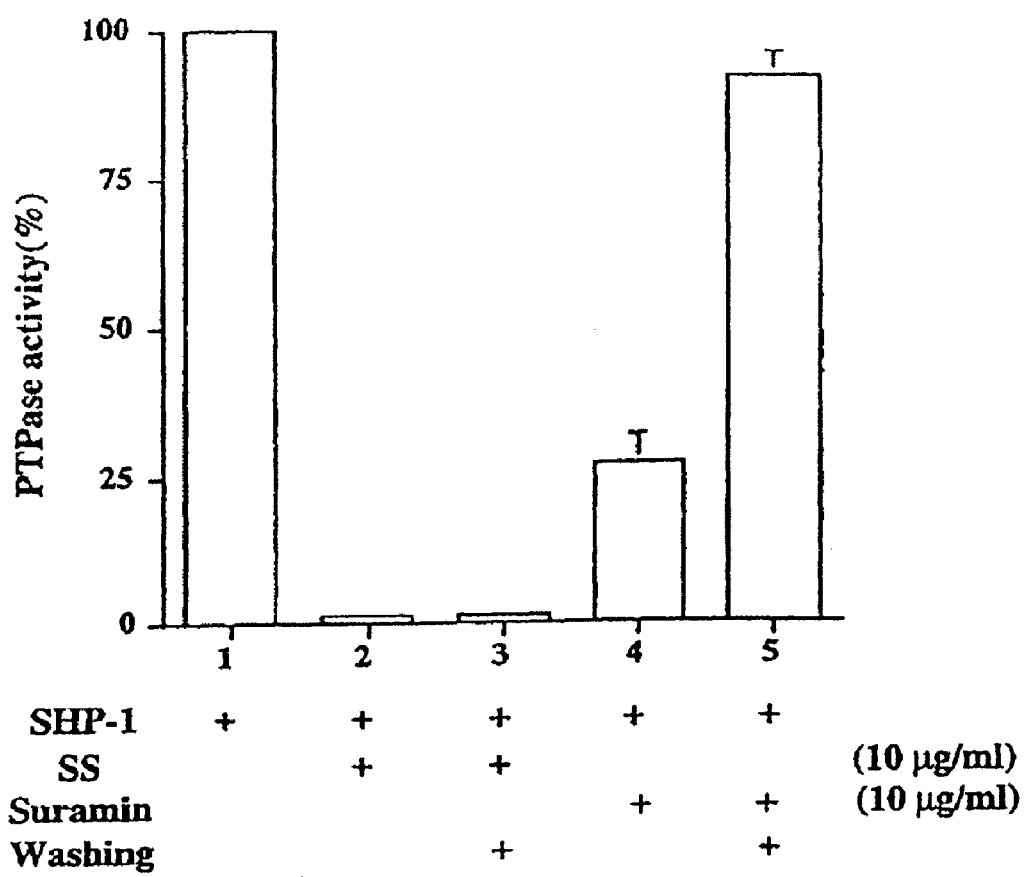
FIG. 3. Sodium stibogluconate forms stable complexes with SHP-1 in vitro. Relative PTPase activities of GST fusion protein of SHP-1 preincubated with sodium stibogluconate or Suramin and then washed (+) or without washing (−) as indicated. The data represent the mean±SD values of triplicate samples measured by in vitro PTPase assays.

We next determined whether the in vitro inhibition of SHP-1 PTPase by sodium stibogluconate is a reversible process. For this, we examined whether washing the GST-SHP-1 fusion protein pre-incubated with sodium stibogluconate could relieve the inhibition. The inhibition of the GST/SHP-1 fusion protein by sodium stibogluconate was not affected by washing (FIG. 3). In contrast, the inhibition of the phosphatase by Suramin was almost completely removed by the washing process (FIG. 3), consistent with a previous report.

Figure 4:
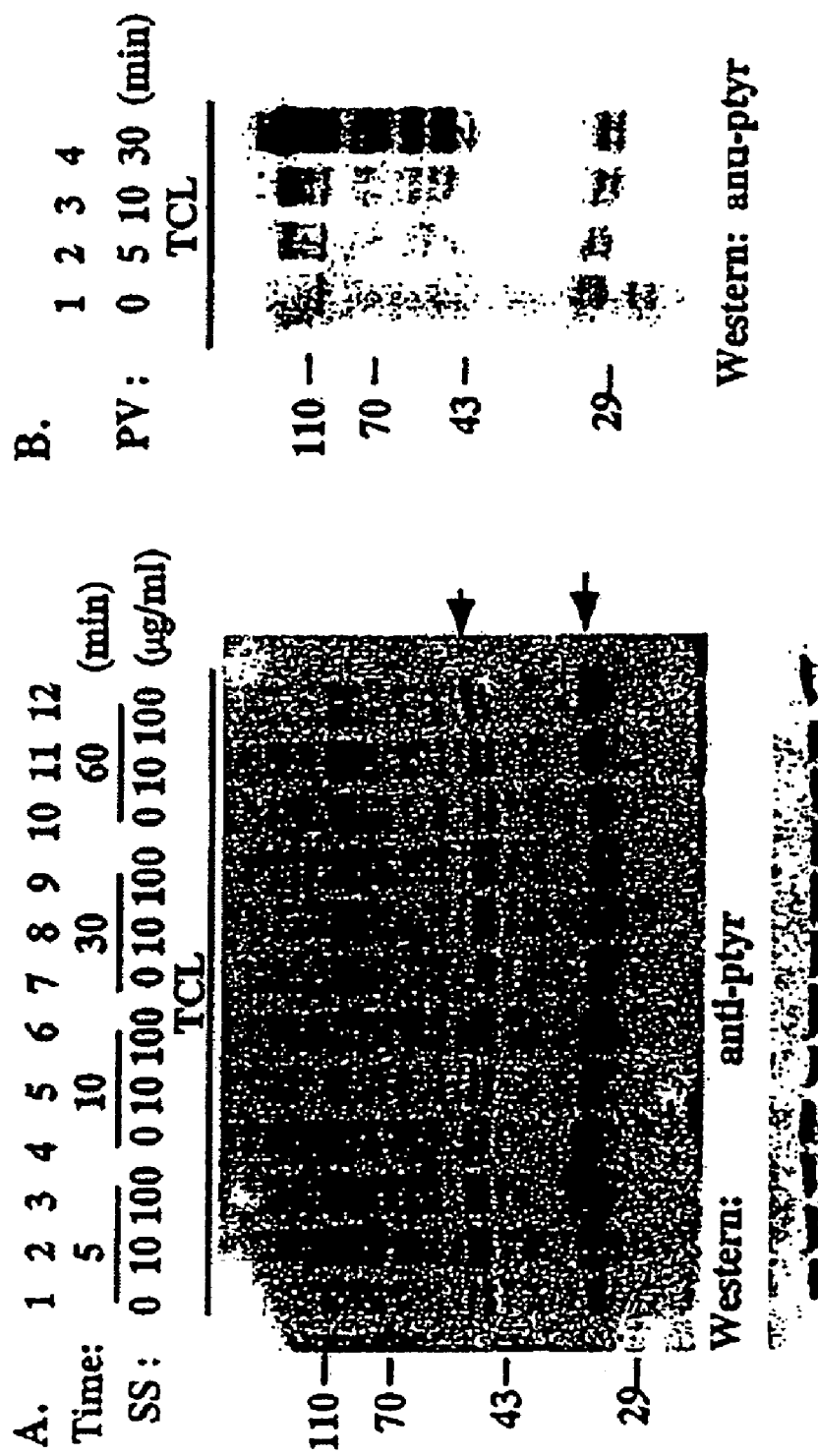
FIG. 4. Induction of cellular protein tyrosine phosphorylation in Baf3 cells by sodium stibogluconate. Total cell lysate (TCL) of Baf3 cells deprived of IL-3 for 16 hours and then incubated with sodium stibogluconate (SS) (A) or pervanadate (PV, 0.1 mM) (B) for various times was resolved in a SDS-PAGE gel, blotted to a membrane and probed with a monoclonal antibody against phosphotyrosine or against the β-actin protein. Two proteins with increased phosphotyrosine content in presence of sodium stibogluconate are marked by arrows. The positions of protein size markers (kDa) are indicated on the left.

Sodium stibogluconate induces tyrosine phosphorylation of cellular proteins and augments IL-3-induced Jak2/Stat5 phosphorylation in Baf3 cells. It is expected that the inhibition of PTPases in vivo will increase tyrosine phosphorylation of cellular protein substrates. To determine whether sodium stibogluconate functions as a PTPase inhibitor in vivo, we examined its effect on cellular protein tyrosine phosphorylation in the murine IL-3-dependent cell line Baf3. Treatment of Baf3 cells with sodium stibogluconate induced protein tyrosine phosphorylation (FIG. 4A) that was modest and transient in comparison with those induced by pervanadate (FIG. 4B). Increased tyrosine phosphorylation of cellular proteins of approximately 55 and 32 kDa was apparent in cells incubated with the drug for 5 minutes (FIG. 4, Lane 1-3). This induction of cellular protein tyrosine phosphorylation was dose-dependent with more marked induction occurred at the higher drug concentration (FIG. 4, comparing lane 2 and 3). Heightened phosphorylation of these proteins was also detected with prolonged treatment of 10, 30 or 60 minutes but at more modest levels (FIG. 4, Lane 4-12). This increased protein tyrosine phosphorylation was not due to variations in the protein samples as indicated by the similar amounts of β-actin protein in these samples (FIG. 4, lower panel). The drug showed no obvious effect on several other phosphotyrosine cellular proteins in the total cell lysate (TCL) samples (FIG. 4), suggesting certain specificity of the drug in induction of protein tyrosine phosphorylation. The identities of the 55 and 32 kDa proteins have not been determined. The weaker phosphorylation signal of p32 band in lane 1 of FIG. 4 comparing to that of lane 4, 7 and 10 was not consistently detected.

Figure 5:
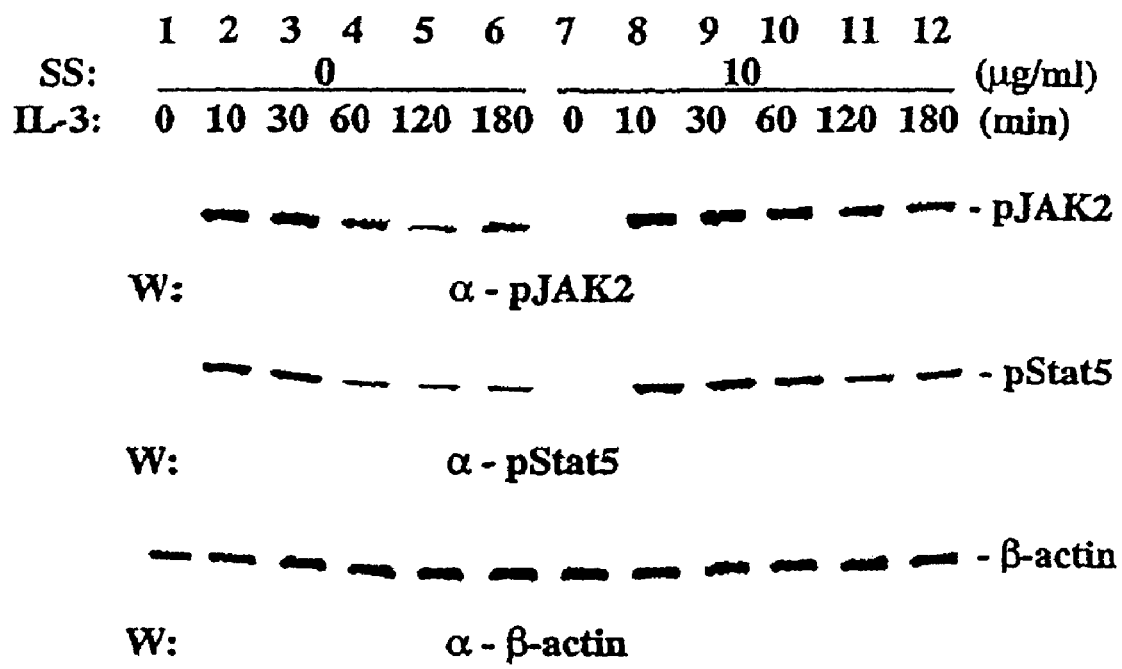
FIG. 5. Sodium stibogluconate augments IL-3-induced Jak2/Stat5 tyrosine phosphorylation in Baf3 cells. Baf3 cells deprived of IL-3 for 16 hours in 0.1% FCS medium were incubated with or without sodium stibogluconate (SS) for 10 minutes and then stimulated with IL-3 for various times. Total cell lysate of the cells was resolved in a SDS-PAGE gel, blotted to a membrane and probed with antibodies against phosphotyrosine Jak2 (pJak2), phosphotyrosine Stat5 (pStat5) or the β-actin protein as indicated. The positions of phosphotyrosine Jak2, phosphotyrosine Stat5 and β-actin are indicated on the right.

A functional role of SHP-1 in dephosphorylating the Jak family kinases during cytokine signaling has been documented. To determine whether sodium stibogluconate inhibits SHP-1 in vivo, we examined the effect of the drug on IL-3-induced Jak2 tyrosine phosphorylation in Baf3 cells (FIG. 5). Baf3 cells deprived of IL-3 were incubated with or without the drug for 10 minutes and then stimulated with IL-3 for various times. IL-3 induced tyrosine phosphorylation of Jak2 and Stat5 in Baf3 cells in the presence or absence of the drug. However, the phosphotyrosine levels of Jak2 and Stat5 in the presence of the drug were about twice of those in cells without drug treatment as determined by densitometry analysis (FIG. 5, comparing Lane 2-6 and Lane 8-12).

In cells unstimulated by IL-3, tyrosine phosphorylation of the two proteins was undetectable in the presence or absence of the drug (FIG. 5, Lane 1 and 7). Prolonged incubation with the drug alone at 37° C. for 16 hours also failed to induce Jak2/Stat5 tyrosine phosphorylation.

Figure 6:
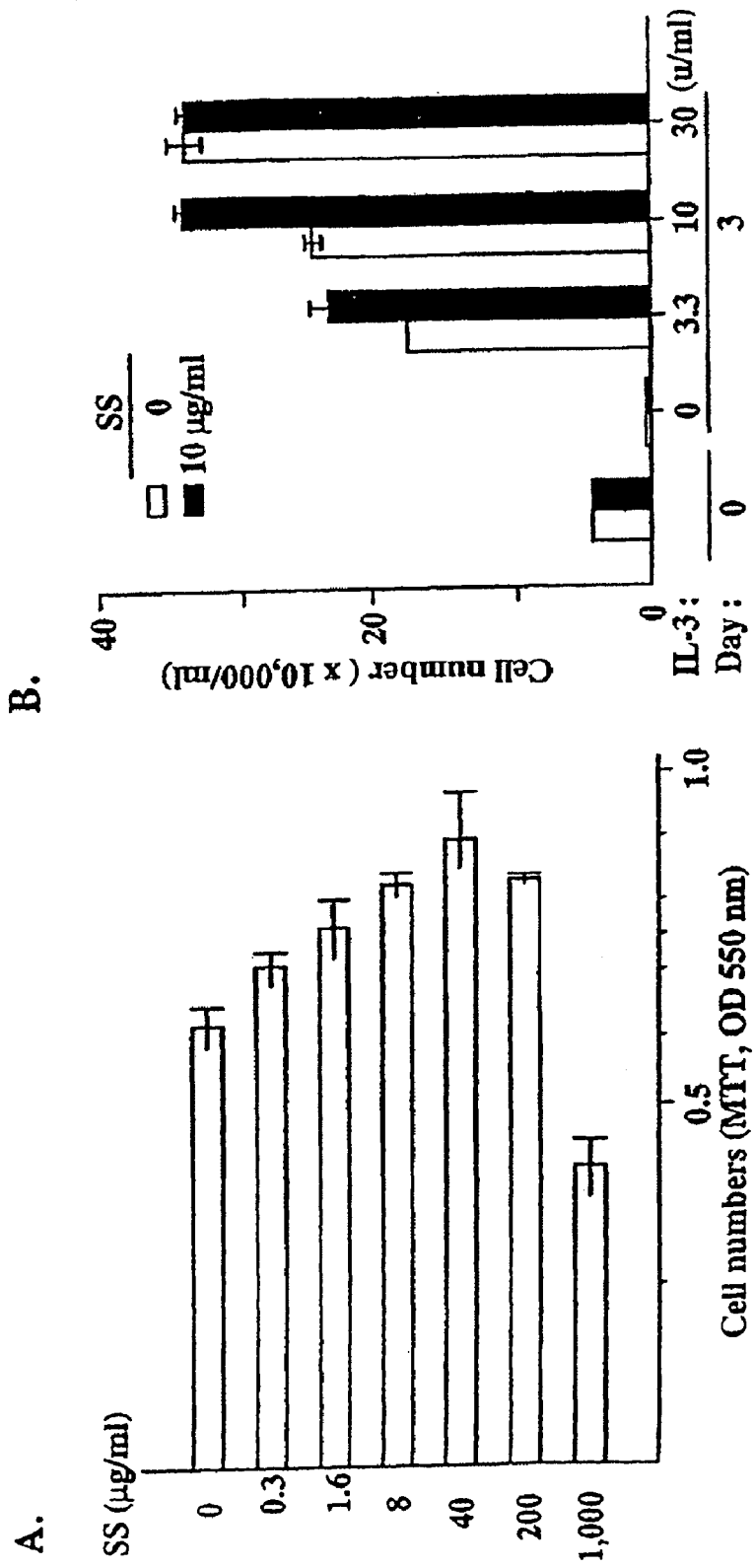
FIG. 6. Sodium stibogluconate augments the proliferative responses of Baf3 cells to IL-3. A. Proliferation of Baf3 cells cultured in the presence of IL-3 (10 unites/ml) and various amounts of sodium stibogluconate (SS) for three days was measured by an MTT assay. B. Proliferation of Baf3 cells cultured for three days in the presence of sodium stibogluconate (10 μg/ml) and various amounts of IL-3 was measured by cell counting under microscope. The data represent the mean±SD values of triplicate samples.

Sodium stibogluconate augments IL-3-induced cell proliferation of Baf3 cells. SHP-1 is known to down-regulate cytokine signaling as demonstrated by the hyperresponsiveness of SHP-1-deficient cells to various cytokines, including IL-3. The inhibitory activity of sodium stibogluconate against SHP-1 predicted that the drug would augment IL-3-induced proliferation of Baf3 cells. Indeed, IL-3-induced Baf3 proliferation was increased in the presence of sodium stibogluconate at 0.3 to 200 µg/ml with the maximal effect concentration about 40 µg/ml (FIG. 6A). This modest increase was consistently detected in two separate experiments (data not shown). At a higher concentration (1,000 µg/ml), the drug suppressed IL-3-induced Baf3 growth (FIG. 6A). This growth promoting, activity of the drug was apparent at suboptimal (3.3 or 10 units/ml), but not optimal (30 unit/ml), amounts of IL-3 (FIG. 6B). In the absence of IL-3, sodium stibogluconate failed to support cell proliferation or maintain cell viability in day 3 culture (FIG. 6B).

Sodium stibogluconate augments the opposite effects of GM-CSF and IFNα on the proliferation of TF-1 cells. The Jak/Stat signaling pathways transduce signals initiated by cytokines that often have opposite effects on cell growth. The human myeloid leukemia cell line TF-1 responds to both GM-CSF, which promotes proliferation, and IFNα, which inhibits cell growth. To determine whether the effect of the PTPase inhibitor is unique for the IL-3-initiated signaling events or affects other cytokines, we examined the growth responses of TF1 cells to GM-CSF and IFNα in the presence or absence of sodium stibogluconate.

Proliferation of TF-1 cells was induced by suboptimal concentrations of GM-CSF (5-40 ng/ml) in a dose-dependent manner (FIG. 7A). This proliferation of TF-1 cells was augmented in the presence of sodium stibogluconate at 50 µg/ml (FIG. 1A). No viable cells were detected in the cultures lacking GM-CSF in the presence or absence of the drug (FIG. 7A). These results demonstrated that sodium stibogluconate augmented the growth promoting activity of GM-CSF in TF-1 cells but could not substitute the growth factor for maintaining cell viability or promoting growth under the experimental conditions.

In the presence of IFNα, GM-CSF-induced proliferation of TF-1 cells was suppressed (FIG. 7B). Further reduction of GM-CSF-induced cell growth was detected in cultures containing both IFNα and sodium stibogluconate (50 µg/ml) (FIGS. 7B and C), indicating that the growth inhibition activity of IFNα was enhanced in the presence of the drug. Since the enhanced growth inhibition of IFNα by the drug occurred in the presence of GM-CSF, it indicated the dominance of the synergy between IFNα and the drug over the activity of the drug in augmenting GM-CSF mitogenic signaling under the experimental conditions.

As shown in FIG. 7D, the activity of sodium stibogluconate in augmenting GM-CSF-induced TF-1 proliferation was dose-dependent, with the optimal activity at 50 µg/ml. On the other hand, more dramatic growth inhibition in the presence of IFNα occurred at higher concentrations of the drug (FIG. 7E). Since the drug at low doses (12.5-50 µg/ml) showed no negative effect on GM-CSF-induced cell growth, its effect at such doses in augmenting IFNα-induced growth inhibition was likely resulted from specific enhancement of IFNα signaling. On the other hand, non-specific toxicity of drug at higher doses in combination with IFNα might have contributed to the more dramatic growth inhibition.

The Sb III form of potassium antimonyl tartrate lacks inhibitory activity against PTPases. Sodium stibogluconate is of sb-V form which transforms inside cells into sb-III form that can affect *leishmania* growth. We therefore determined the activity of potassium antimonyl tartrate of sb-III form in inhibiting PTPases in vitro and in vivo.

Unlike sodium stibogluconate, potassium antimonyl tartrate at 1-1,000 µg/ml showed no detectable inhibition of PTPases SHP-1 and PTP1B in vitro (FIG. 8A). It also failed to enhance IL-3-induced Stat5 phosphorylation (FIG. 8B) or IL-3-induced proliferation of Baf3 cells (FIG. 8C), indicating its lack of inhibitory activity against PTPases in vivo. Interestingly, it showed marked toxicity against Baf3 cells. The results together indicate that only the sb-V form acts as a PTPase inhibitor which is inactivated when transformed into the sb-III form.

DISCUSSION: Sodium stibogluconate has been used clinically for decades in the treatment of leishmaniasis, caused by the protozoa *leishmania* that resides in macrophages. While its pharmacological mechanism is poorly understood, there were indications that the drug's therapeutic effect might be mediated via a cellular target(s): it kills intracellular *leishmania* but has no effect on the free living form (promastigotes) of the protozoa that lives in the intestine of sandflys and can grow in defined culture medium in vitro.

Figure 8:
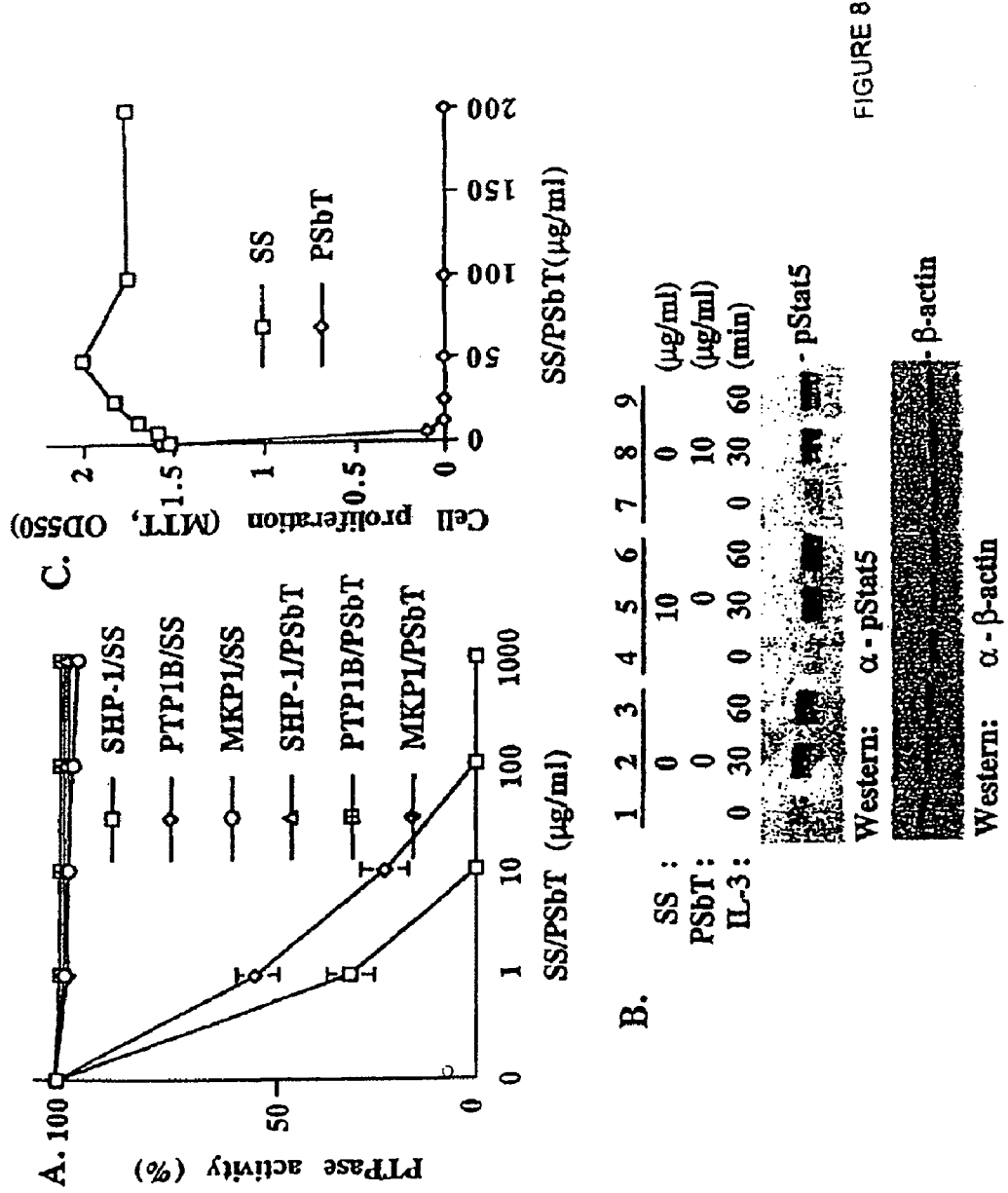
FIG. 8. Potassium antimonyl tartrate lacks inhibitory activity against PTPases. A. Relative PTPase activities of GST fusion proteins of SHP-1, PTP1B and MKP1 in the presence of various amounts of sodium stibogluconate (SS) or potassium antimonyl tartrate (PSbT). The data represent the mean±SD values of triplicate samples measured by in vitro PTPase assays. B. Total cell lysate of Baf3 cells stimulated with IL-3 for various times in the absence or presence of sodium stibogluconate (SS) or potassium antimonyl tartrate (PSbT) was resolved in a SDS-PAGE gel, blotted to a membrane and probed with antibodies against phosphotyrosine Stat5 (pStat5) or the β-actin protein as indicated. The positions of phosphotyrosine Stat5 and β-actin are indicated on the right. C. Proliferation of Baf3 cells cultured in the presence of IL-3 (10 unites/ml) and various amounts of sodium stibogluconate (SS) or potassium antimonyl tartrate (PSbT) for three days was measured by an MTT assay. The data represent the mean±SD values of triplicate samples.

Our data provide the first evidence that sodium stibogluconate is a potent inhibitor of protein tyrosine phosphatases in vitro and in vivo. Sodium stibogluconate inhibited the dephosphorylation of a synthetic phosphotyrosine peptide substrate by protein tyrosine phosphatases (SHP-1, SHP-2 and PTP1B) in in vitro PTPase assays (FIG. 1). The dephosphorylation of pNPP (p-nitrophenyl phosphate, Sigma) by these PTPases in vitro was also similarly inhibited by the drug (data not shown). The inhibitory activity of the drug against PTPases in vivo was indicated by the rapid induction of protein tyrosine phosphorylation of the two yet-unidentified cellular proteins of 56 and 32 kDa in Baf3 cells (FIG. 4). Interestingly, proteins of similar molecular weights had been found to be hyperphosphorylated in SHP-1 deficient cells in previous studies. Induced cellular protein tyrosine phosphorylation was less dramatic with prolonged drug incubation (FIG. 4), suggesting that the drug may be unstable under the experimental conditions or that the drug may sequentially inactivate PTPases with opposite effects on the phosphorylation of the cellular proteins. In this regard, it is interesting that PTPases were inhibited by the sb-V form of sodium stibogluconate which is known to transform in cells to the sb-III form that failed to show PTPase inhibitory activity (FIG. 8). The intracellular transformation therefore could result in inactivation of the PTPase inhibitor and may account for the drug's modest and transient induction of tyrosine phosphorylation and modest effect on cell proliferation. This may have a beneficial side as it may be related to the lower toxicity of the drug in comparison to other PTPase inhibitors that allows its clinical application.

The inhibitory activity of sodium stibogluconate against PTPases in vivo was further indicated by the augmentation of IL-3-induced Jak2/Stat5 phosphorylation and IL-3-induced proliferation of Baf3 cells. We and others showed previously that SHP-1 dephosphorylates the Jak family kinases to down regulate signaling initiated by cytokines. Among the Jak kinases, IL-3 specifically activates the Jak2 kinase which phosphorylates the Stat5 protein to regulate gene expression. The observation that sodium stibogluconate augmented IL-3-induced Jak2/Stat5 tyrosine phosphorylation and IL-3-induced proliferation of Baf3 cells is therefore consistent with inhibition of SHP-1 by the drug in vivo. However, it remains possible that the effect of the drug on IL-3-induced Jak2/Stat5 phosphorylation and cell proliferation involves additional PTPases (e.g., the CD45 PTPase) that participate in dephosphorylating the Jak kinases. Indeed, sodium stibogluconate augmented G-CSF-induced Tyk2/Stat3 tyrosine phosphorylation in SHP-1-deficient cells (our unpublished data). The enhancement of IL-3-induced Jak2/Stat5 tyrosine phosphorylation by the drug was more dramatic in later time points post IL-3 stimulation, indicating induction of extended period of phosphorylation by the drug. Such an effect of the drug suggests its targeting of PTPases recruited to Jak2/Stat5 at the later time points post IL-3 stimulation to inactivate the signaling molecules.

Figure 7:
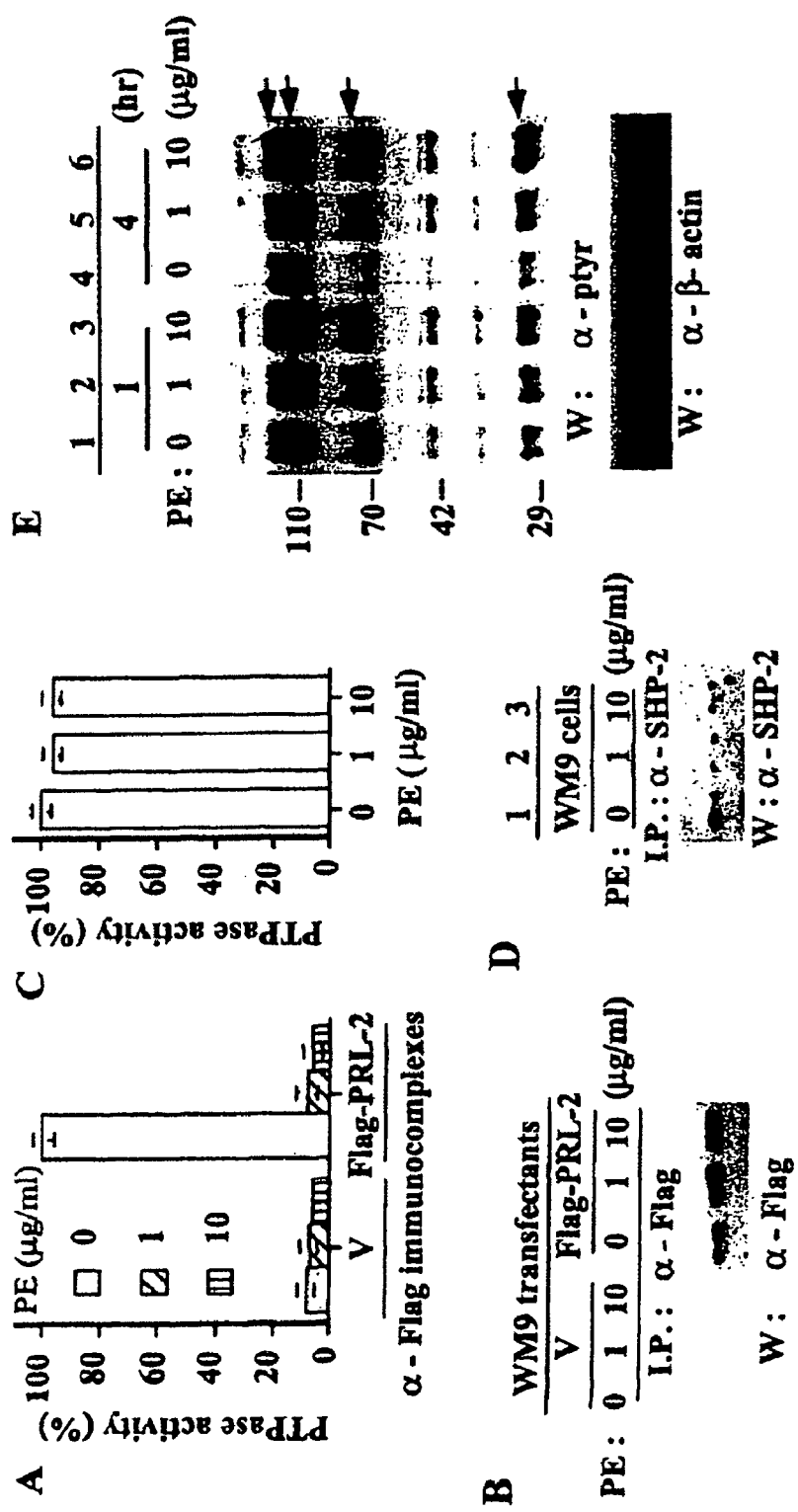
FIG. 7. Sodium stibogluconate augments the opposite effects of GM-CSF and IFNα on TF-1 cell growth. A. Proliferation of TF-1 cells cultured in the presence of various amounts of GM-CSF and with or without sodium stibogluconate for three days was measured by MTT assays. B. Proliferation of TF-1 cells cultured in the presence of GM-CSF (50 ng/ml) and various amounts of IFNα with or without sodium stibogluconate (50 μg/ml) for three days was measured by MTT assays. C. The results in B shown as percentage inhibition of cell growth. D. Proliferation of TF-1 cells in the presence of GM-CSF (20 ng/ml) and various amounts of sodium stibogluconate for 6 days was measured by MTT assays. E. Proliferation of TF-1 cells in the presence of GM-CSF (20 ng/ml)/IFNα (1,000 u/ml) and various amounts of sodium stibogluconate for 6 days was measured by MTT assays. The data represent the mean±SD values of triplicate samples.

Inhibition of PTPases in vivo by sodium stibogluconate was also consistent with the observation that the drug augmented the opposite effects of GM-CSF and IFNα on TF-1 cell proliferation (FIGS. 7 and 8). In particular, the observation suggested that the drug targeted PTPases which dephosphorylate shared signaling molecules (e.g., the Jak family kinases) utilized by both GM-CSF and IFNα. Such a putative mechanism would explain the cytokine-dependent effects of the drug: its inhibition of PTPases leads to amplification of both mitogenic and growth inhibitory signals initiated by GM-CSF and IFNα respectively. It also suggests that drug may have broad activities in augmenting the signaling of various cytokines. It is worth noticing that SHP-1 has been shown in previous studies to down regulate the signaling of GM-CSF and IFNα. It was reported that macrophages from SHP-1-deficient mice show approximately 2 folds increase of GM-CSF-induced cell growth in comparison to controls. This level of growth increase is similar to the increase of GM-CSF-induced TF-1 cell growth in the presence of sodium stibogluconate, consistent with inhibition of SHP-1 by the drug. In light of the pathogenic effect of SHP-1-deficient monocytes/macrophages in the fatal motheaten phenotype, it is possible that the apparently modest effect of the drug on GM-CSF-induced cell growth could have significant biological consequences in vivo.

Our results also suggest that inhibition of PTPases by sodium stibogluconate at therapeutic concentrations to increase Jak/Stat phosphorylation and cellular responses to cytokines may be a major factor responsible for the pharmacological effect of the drug in the treatment of leishmaniasis. Among the cytokines that depend on Jak/Stat pathways for signal transduction, IFN-γ plays an important role in eliminating intracellular *leishmania*. Moreover, impaired IFN-γ signaling was detected in *leishmania*-infected macrophages and was associated with activation of SHP-1 by the parasite. Therefore, it could be postulated that sodium stibogluconate may augment IFN-γ signaling in macrophages via inhibiting SHP-1 (and other PTPases) and contribute to the clearance of intracellular *leishmania*. Thus anti-*leishmania* activity of sodium stibogluconate may derive both from augmenting cell signaling by sb-V and from parasite-killing by sb-III transformed from sb-V inside cells. Such a functional mechanism, nevertheless, is consistent with previous observations that modulation of host PTPases with specific inhibitors can effectively control the progression of *Leishmania* infection by enhancing cytokine signaling in macrophages. In light of the observation that anti-*leishmania* drug sodium arsenite inhibits LPS-induced MAP kinase signaling in macrophages, modulation of cellular signaling could be a common mechanism of anti-*Leishmania* drugs.

Figure 2:
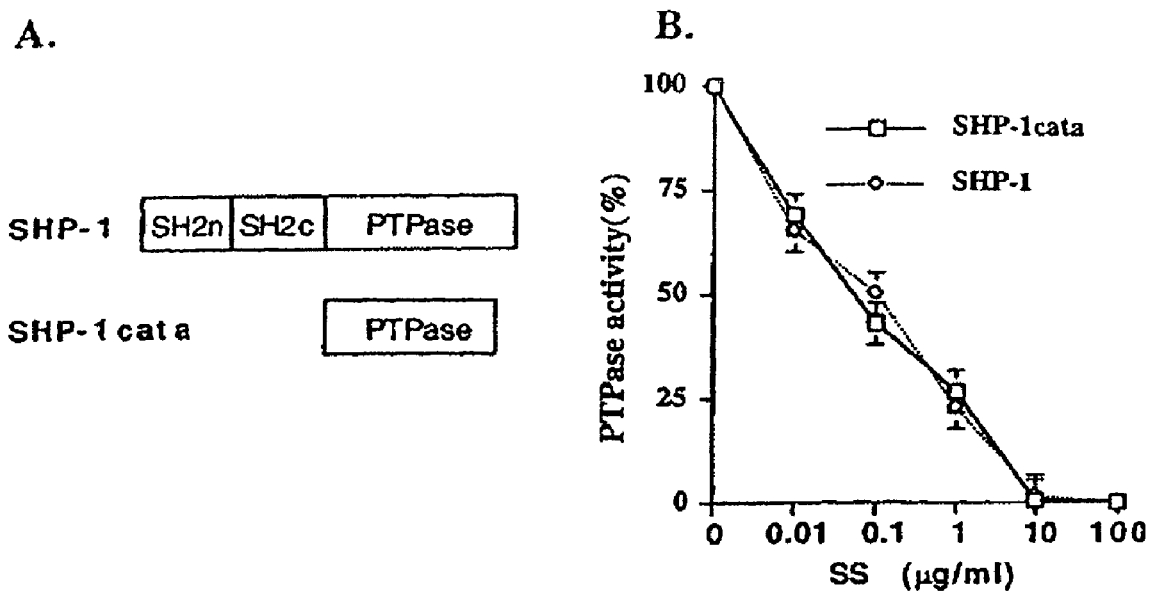
FIG. 2. Sodium stibogluconate targets the catalytic domain of SHP-1. A. Protein domain structure of GST fusion proteins of SHP-1 and SHP-1 catalytic domain (SHP-1cata) which contains amino acid 202 to 554 of the wild type SHP-1 protein. B. Relative PTPase activities of GST fusion proteins of SHP-1 and SHP-1cata in the presence of various amounts of sodium stibogluconate. The data represent the mean±SD values of triplicate samples measured by in vitro PTPase assays.

The mechanism through which the drug inhibits PTPases is likely by targeting the PTPase catalytic domain of the enzymes. The drug was effective in inhibiting both the wild type SHP-1 and the SHP-1 mutant containing the PTPase domain without the flanking N-terminal SH2 domains or the C-terminal region that regulate SHP-1 activity (FIG. 2). This mechanism is also consistent with the observation that the drug inhibited PTP1B which, except for its PTPase catalytic domain, has no apparent structure similarity with SHP-1 and SHP-2. In this regard, it is not unexpected that the drug showed no obvious activity against MKP1 since the amino acid sequence and structure of the catalytic domain of dual specificity phosphatases are substantially different from those of the tyrosine specific PTPases. Such a mechanism also suggests that the drug may have inhibitory activities against all tyrosine specific PTPases that have the conserved PTPase catalytic domain. While our results indicated that the drug formed a stable complex with SHP-1 in vitro that was resistant to a washing process, it is not clear at present whether this was due to docking of the drug into a pocket structure in the PTPase domain or involved the formation of covalent bonds. In the former case, it is likely subtle differences in the putative pocket structure of PTPases may be responsible for the different sensitivities of the enzymes to the inhibitor in vitro. In addition, it also suggests the feasibility of developing chemical derivatives of the drug with more specific and potent activities against individual PTPases.

Demonstrated differential sensitivities of PTPases to the drug in vitro suggest similar differential sensitivities of PTPases in vivo, which may explain the dose-dependent effect of the drug on IL-3-induced cell proliferation and the known clinical side effect of the drug at higher dosages. Sodium stibogluconate augmented IL-3-induced Baf3 proliferation at therapeutic concentrations and suppressed cell growth at higher dosages. In clinical applications, sodium stibogluconate at therapeutic dosages was well tolerated but is known at higher dosages to have side effects that include reversible nonspecific ECG changes and renal defects. Effects of the drug at higher dosages may be related to inhibition of PTPases that are only sensitive to the drug at higher concentrations.

Importantly, our finding that sodium stibogluconate was a potent inhibitor of PTPases and an enhancer of cytokine signaling suggest potential novel clinical applications for the drug in a variety of situations in which increased cytokine responses are beneficial. It is tempting to speculate co-administration of the drug with cytokines will improve the efficacy of existing cytokine therapies and reduce side effects and costs associated with cytokine therapies. Moreover, the drug by itself may have therapeutic effects through inhibiting PTPases to change the balance of intracellular tyrosine phosphorylation that controls cell proliferation, differentiation and functional activities. In this regard, it is worth noticing that Suramin is presently being evaluated in clinical trials for the treatment of prostate cancer and other solid tumors. As sodium stibogluconate appeared to be a more efficient inhibitor of PTPases than Suramin, it has the potential to become a better drug for effective treatment of these diseases.

PTPase Inhibitor Sodium Stibogluconate Induces Differentiation of Human Myeloid Leukemia Cell Lines In Vitro Potential of differentiation induction therapy in AML treatment is highlighted by the recent success of ATRA in the treatment of acute promyelocytic leukemia. We have studied the in vitro biological activity of sodium stibogluconate (SS) on differentiation of myeloid leukemia cell lines (NB4, HL-60 and U937). SS has been used in the treatment of Leishmaniasis for decades and was identified in our recent studies as a potent inhibitor of cellular PTPases. Herein, we present data demonstrating that SS (250 μg/ml, 6 days) induced 87% of NB4 cells to reduce nitroblue tetrazolium (NBT), in comparison to the 90% induced by ATRA (1 μM, 6 days). SS-induced NB4 cell differentiation was confirmed by increased CD11b expression and associated with growth arrest at S phase and increased cell death. Our results showed further that SS-induced NB4 differentiation was irreversible and required continuous drug exposure for optimal induction. Moreover, SS (400 μg/ml, 6 days) induced 60% and 55% of NBT-positive cells in HL-60 and U937 cell lines, which were augmented in the presence of GM-CSF (2 ng/ml) to levels (85% and 81%, respectively) comparable to those induced by ATRA. These results provide the first evidence of a differentiation induction activity of PTPase inhibitor SS in myeloid leukemia cell lines and suggest its potential therapeutic use in myeloid leukemia. Since SS induces differentiation via targeting PTPases, a mechanism distinct from that of ATRA, it may be particularly useful in AML cases unresponsive or developed resistance to ATRA Acute myeloid leukemia (AML) is characterized by the accumulation of myeloid blast cells that are arrested at various differentiation stages and unable to terminally differentiate. Based on morphology, cytochemistry, immunological markers and cytogenetics, AML can be divided into distinct subclasses according to the French-American-British (FAB) classification. Treatment for most subclasses of AML is unsatisfactory. It usually includes intensive chemotherapy administered as induction treatment to induce complete hematological remission and consolidation therapy to eradicate residual disease. Consolidation therapy with chemotherapy alone or in combination with autologous stem cell transplantation is associated with a relatively high risk of relapse and a longterm disease-free survival of less than 50%. Consolidation therapy with allotransplantation has a lower relapse risk but a higher treatment-related mortality.

Potential of differentiation induction therapy in AML treatment is highlighted by the recent success of all-trans retinoic acid (ATRA) in the treatment of acute promyelocytic leukemia (APL, M3 subclass). ATRA has been shown to induce complete remission and increased long term APL-free survival exceeding 75%. This therapeutic effect of ATRA derives from its activity in inducing terminal differentiation of APL cells through its binding to aberrantly generated chimeric proteins of retinoic acid receptor a (RARα) that results in degradation of the chimeric proteins and altered transcription regulation. As generation of chimeric proteins of RARα is restricted to APL cells, differentiation induction therapy with ATRA showed only limited benefit in the treatment of other AML subclasses. Moreover, ATRA differentiation induction therapy works well only in a subset of APL cases with translocation but showed little or no effect on those with translocation. Therapeutic use of ATRA is further compromised by serious systemic toxicity and induced ATRA resistance. Nevertheless, the marked success of ATRA in the subgroup of APL cases has provided evidence indicating the efficacy of differentiation induction therapy in AML treatment and prompted extensive efforts to identify other differentiation induction therapeutics. Several candidates were reported recently, including arsenic derivatives and histone deacetylase inhibitors. Although a number of hematopoietic growth factors and cytokines used alone or in combination with other reagents are known to promote myeloid differentiation, their clinic usage in AML treatment is controversial due to marked variations in the responses of AML cells to the ligands.

Several lines of evidence have indicated that AML cell differentiation is affected by cellular protein tyrosine phosphorylation regulated by the balance of protein tyrosine kinases (PTKs) and protein tyrosine phosphatases (PTPases). Granulocytic maturation of HL-60 promyelocytic leukemia cells was shown to produce a decrease in cellular protein tyrosine phosphorylation and increases in both tyrosine kinase and protein phosphotyrosine phosphatase activities. HePTP amplification and overexpression were found in AML cells and cell lines and may contribute to abnormal AML cell growth and arrest of differentiation. The involvement of hematopoietic cell phosphatase SHP-1 was indicated by its increased expression during HL-60 cell differentiation and its inhibition of Epo-induced differentiation of J2E leukemic cells. Interestingly, PTK inhibitor STI571 was shown to enhance ATRA-induced differentiation of APL cells although it alone had no differentiation induction activity. So far, induction of AML cell differentiation by PTPase inhibitors has not been reported.

Sodium stibogluconate (SS) was discussed above as a potent inhibitor of PTPases that augments signaling of various hematopoietic growth factors and cytokines. SS has been used for decades in the treatment of leishmaniasis, caused by the protozoa parasites residing in macrophages. While its pharmacological mechanism is poorly understood, there were indications that the drug's therapeutic effect might be mediated via a cellular target(s): it kills intracellular *leishmania* but has no effect on the free living form (promastigotes) of the protozoa that lives in the intestine of sandflys and can grow in defined culture medium in vitro. We provided the first evidence that SS is a potent inhibitor of PTPases, including SHP-1, in vitro and in vivo. We demonstrated that the PTPase inhibitor could augment cell growth responses to hematopoietic growth factors and cytokines, in part, by enhancing Jak/Stat tyrosine phosphorylation. Our data suggest that augmenting signaling of cytokines (e.g., IFNγ) involved in the killing of the intracellular parasite may be an important pharmacological mechanism of the drug in the treatment of Leishmaniasis.

To explore the potential of SS as a drug in differentiation induction therapy in the treatment of AML, we have determined its effect on differentiation of various human AML cell lines in vitro. Our data demonstrate that the PTPase inhibitor induces differentiation of AML cell lines NB4, HL-60 and U937 in a dose- and time-dependent manner. At optimal dosage, SS induced irreversible differentiation of NB4 cells to a level similar to that induced by ATRA. SS-induced differentiation of HL-60 and U937 cells was at 60% and 50% respectively, which were augmented by GM-CSF to levels nearly equal or higher than those induced by ATRA in the two cell lines. These results provide the first evidence of differentiation induction activity of the PTPase inhibitor in AML cells and indicate the potential of SS, and probably other PTPase inhibitors, in AML treatment.

Materials and Methods

Reagents. All-trans-retinoic acid (ATRA), nitroblue tetrazolium (NBT), and 12-O-tetradecanoylphorbol-13-acetate (TPA) were purchased from Sigma (Saint Louis, Mo.). Sodium stibogluconate and recombinant human GM-CSF have been described previously.

Cell lines, cell culture and cell proliferation assay. The NB4 cell line was a gift from Dr. Dan Lindner of CCF. HL60 and U937 cell lines were purchased from ATCC. These human AML cell lines were maintained in RPMI 1640 medium supplemented with 10% fetal calf serum (FCS). For cell proliferation assays, cells were cultured at 37° C. in 10% FCS medium containing various amounts of SS for 6 days. The cell numbers in the cultures were determined by an MTT assay as described previously.

Studies of induction of Differentiation. Differentiation of AML cell lines was assessed by their ability to produce superoxide as measured by reduction of NBT to formazan and by analysis of expression of CD11b surface marker by flow cytometry. For NBT reduction, each cell suspension was mixed with an equal volume of solution containing 1 mg/ml of NBT (Sigma) and 2.5 µg/ml of TPA for 30 minutes at 37° C. After incubation, cells containing the purple formazan deposits and cells devoid of NBT-reducing activity (white cells) in each sample was determined by counting 200 cells under microscope. We expressed the data as percentage of the following ratio: purple cells/purple+white cells. For analysis of cell surface antigens, cells were exposed to phycoerythrin (PE)-conjugated murine anti-human CD11b (DAKO corp, Carpinteria, Calif.). Analysis of fluorescence was performed on a FACScan flow cytometer (Beckton Dickinson, Mountain View, Calif.).

Cell cycle analysis. The cell cycle was analyzed by flow cytometry after 3 days of culture of NB4 cells in the absence or presence of SS (250 µg/ml) or ATRA (1 µM). Briefly, the cells were fixed in cold ethanol and incubated for 30 minutes at 4° C. in the dark with a solution of 50 mg/ml propidium iodide, 1 mg/ml RNase and 0.1% NP-40. Analysis was performed immediately after staining using the CELLFIT program (Becton Dickinson, Mountain View, Calif.).

Detection of apoptotic cells by Annexin V/Propidium Iodide assay. Annexin V staining of exposed membrane phospholipid phosphatidylserine (PS) was done using the Annexin V assay kit (Pharmingen, San Diego, Calif.). Briefly, NB4 cells were cultured in the 10% FCS RPMI 1640 medium in the absence or presence of SS (250 µg/ml) or ATRA (1 µM) for 3 days. Cells were then washed in PBS twice and stained in binding buffer (10 mM Hepes, pH 7.4; 140 mM NaCl; 2.5 mM CaCl2) containing Annexin V-FITC and propidium iodide for 15 min. The reaction was stopped by adding 10 volumes of binding buffer and analyzed by FACS (Becton Dickinson Facsvantage).

Results

SS induces differentiation of AML cell line NB4 in a dose- and time-dependent manner. NB4 is a human AML cell line derived from an APL patient and can be induced to differentiate into granulocytes by ATRA. To explore the potential of SS in differentiation induction therapy for AML, we initially determined the activity of the drug in inducing differentiation of NB4 cells into more mature granulocyte-like cells by NBT reduction assays and CD11b antigen expression.

Figure 9:
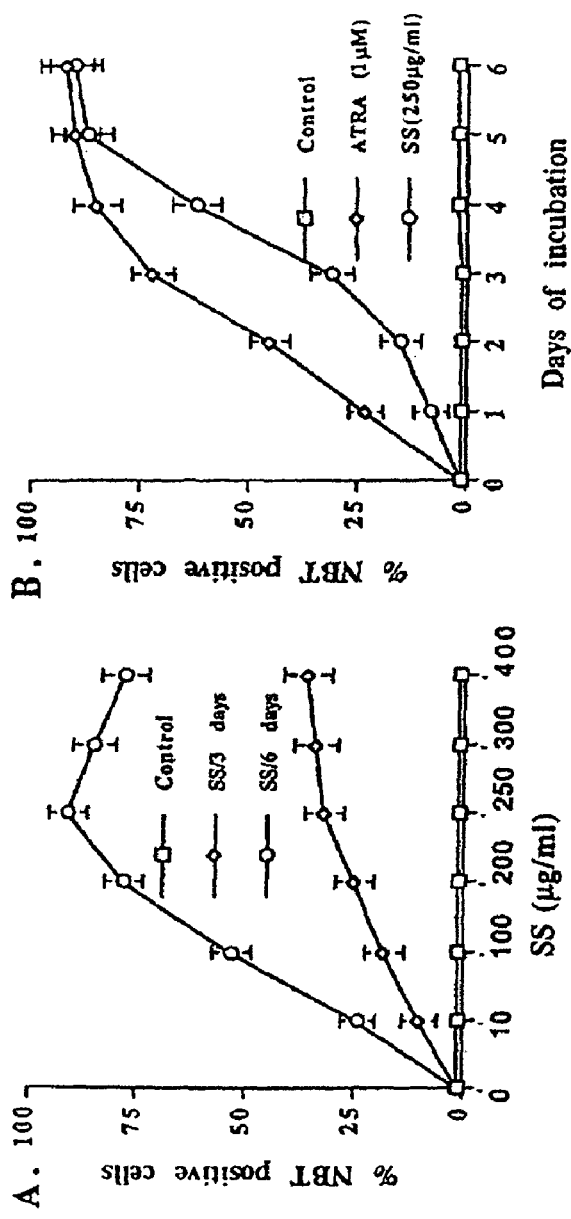
FIG. 9. SS induces NB4 differentiation in a dose- and time-dependent manner. A. NB4 cells were cultured in the absence or presence of various amounts of SS for 3 or 6 days. The percentage of NBT-positive cells in NB4 cells cultures was determined. The data represent the mean±SD values of triplicate samples. B. The percentage of NBT-positive cells in NB4 cells cultured in the presence 1 μM of ATRA or 250 μg/ml of SS for various time points. The data represent the mean±SD of triplicate samples. C. The percentage of CD11b-positive (CD11b+) cells in NB4 cells cultured in the presence 250 μg/ml of SS or ATRA for 3 days as determined by FACS analysis.
Figure 9:
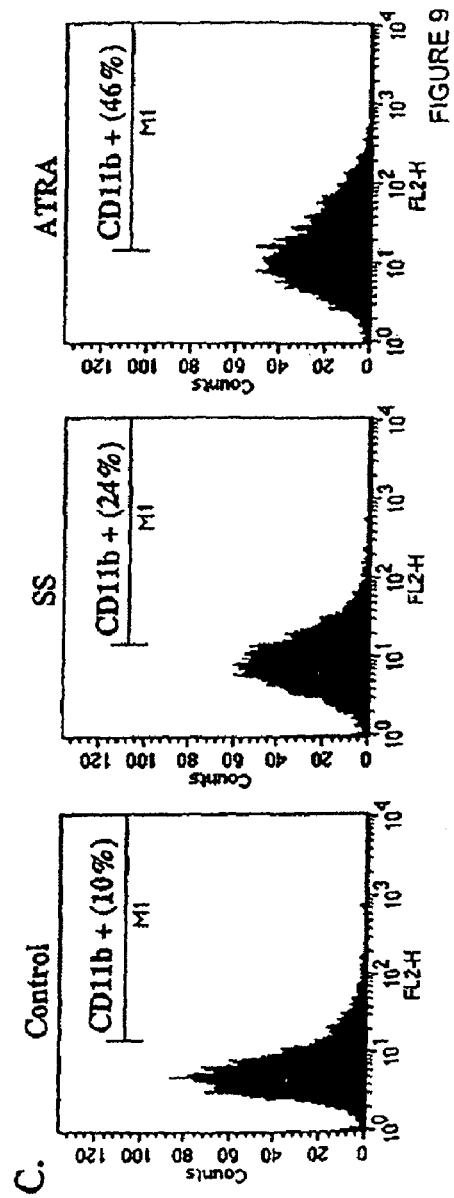

SS induced NB4 cell differentiation in dose- and time-dependent manner (FIG. 9) as indicated by the increase of NBT positive cells in the presence of the drug. SS showed such a differentiation induction activity at all of the dosages (10 to 400 µg/ml) that were tested in day 3 or day 6 culture (FIG. 9A). The optimal dosage was at 250 µg/ml which induced 87% differentiation of NB4 cells cultured in the presence of SS for 6 days (FIG. 9A). At this dosage, SS-induced NB4 cell differentiation was detectable after cells were treated with the drug for the first 24 hours, increased further during the following days and reached 87% by day 6 (FIG. 9B). NB4 cells treated with ATRA (1 µM) for 6 days also reached a similar degree of cell differentiation under comparable conditions (FIG. 9B). SS-induced NB4 cell differentiation was further confirmed by the increase of CD11b positive cells from 10% in the control to 24% in NB4 cells cultured in the presence of SS (250 µg/ml) for 3 days (FIG. 9C).

Figure 10:
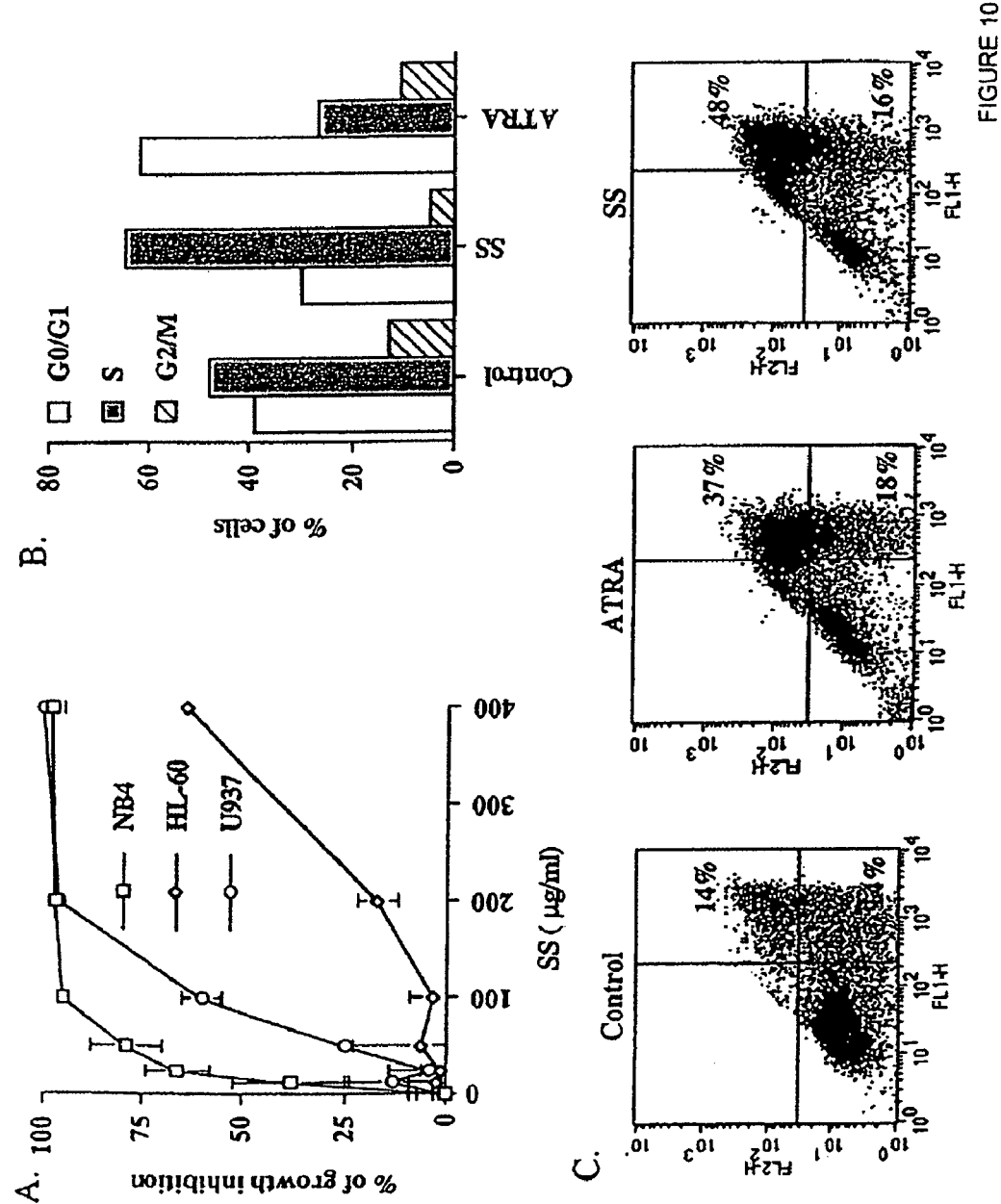
FIG. 10. SS-induced NB4 cell differentiation associates with growth arrest at S phase and cell death. A. NB4, HL-60 and U937 cells were cultured in the absence or presence of various amounts of SS for 6 days. Cell growth was determined by MTT assays. Percentage of cell growth inhibition was calculated [(cell growth in the presence of SS/cell growth in the absence of SS−1)×100%]. The data represent the mean±SD of triplicate samples. B. NB4 cells cultured for 3 days in the absence or presence of SS (250 μg/ml) or ATRA (1 μM) were stained with propidium iodide and analyzed for cellular DNA content to calculate the percentage of cells at G0/G1, S or G2/M phases. C. NB4 cells cultured for 3 days in the absence or presence of SS (250 μg/ml) or ATRA (1 μM) were stained with propidium iodide (PI, Y-Axis) and Annexin V FITC (X-Axis). Flow cytometric plots show binding Annexin V, indicating exposure of phosphatidylserine residues on the cell membrane (early stages of apoptosis), and PI labeling, indicating membrane permeabilization (late-stage cell death).

SS-induced NB4 cell differentiation associates with cell growth arrest at S phase and increased cell death. We next determined the effect of SS on NB-4 cell growth by MTT assays. Proliferation of NB4 cells was markedly inhibited in the presence of SS at all the dosages that were examined (12.5-400 µg/ml) (FIG. 10A). Cell DNA content analysis (FIG. 10) showed a significant increase of cells at S phase in the NB4 cells treated with SS (250 µg/ml) for 3 days (FIG. 10B). In contrast, NB4 cells cultured in the presence of ATRA (1 µM) for 3 days were arrested at G1 phase (FIG. 10B), consistent with a previous report. A substantial population of NB4 cells cultured in the presence of SS (250 µg/ml) for 6 days was stained positive by Annexin V, suggesting that the cells were dying through apoptosis (FIG. 10C). These results demonstrated that SS induced NB4 cell growth arrest at S phase and had a cytotoxic effect against the cells.

Figure 11:
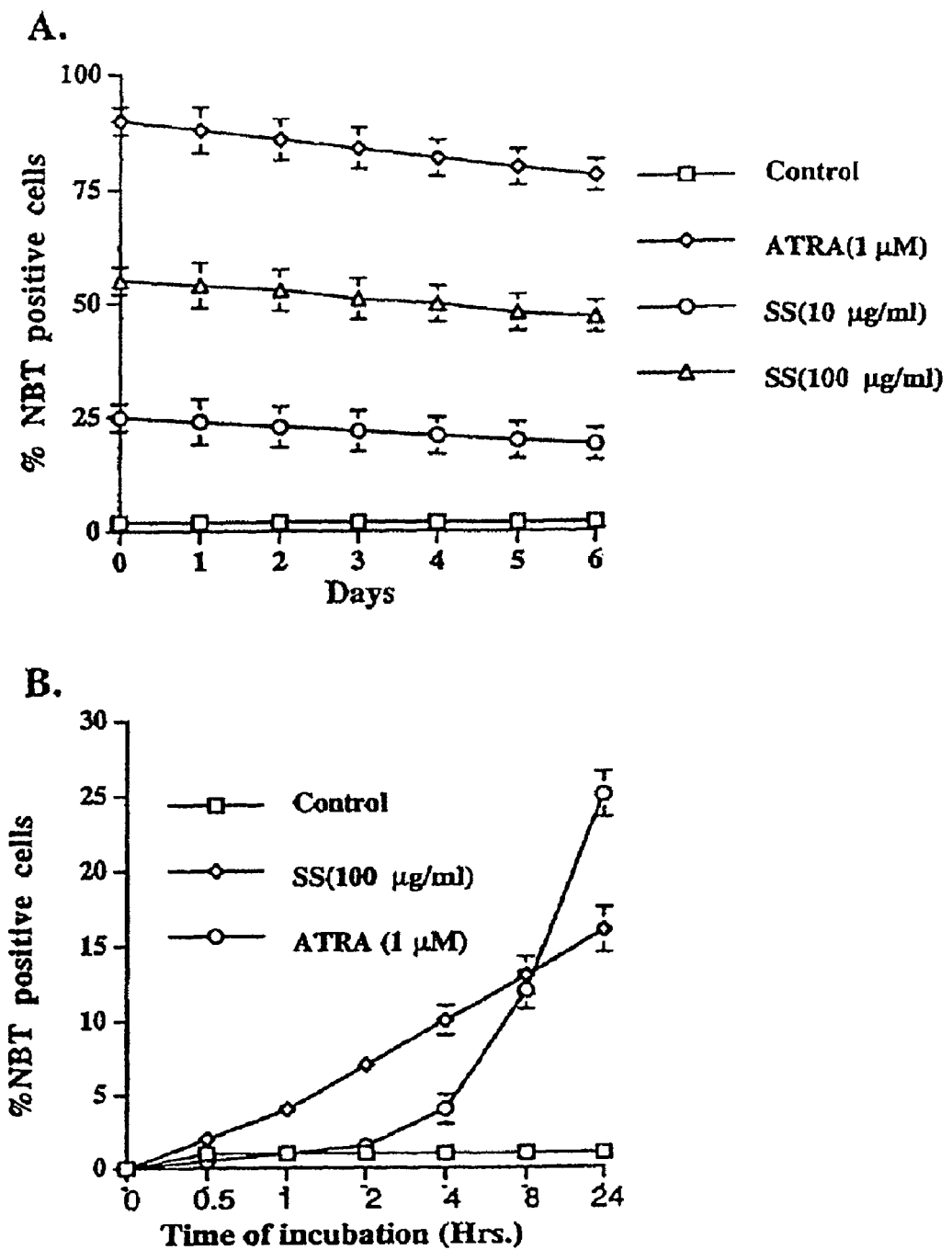
FIG. 11. SS-induced NB4 differentiation is irreversible and could be triggered by short exposure to the drug. A. NB4 cells cultured in the absence or presence of SS (100 μg/ml) or ATRA (1 μM) for 6 days were washed, resuspended in medium without the drug and cultured for 6 days with the percentage of NBT-positive cells determined daily. B. NB4 cells were incubated with SS (100 μg/ml) or ATRA (1 μM) for 0.5 to 24 hours. The cells were then washed, resuspended in medium without the drugs and cultured for 6 days. The percentage of NBT-positive cells in the day 6 cultures were determined. The data represent the mean±SD of triplicate samples.

SS-induced NB4 differentiation is irreversible and requires continuous exposure to the drug for optimal induction. We next investigated whether SS-induced NB4 differentiation would be reversed in the absence of the drug. NB4 cells cultured in the presence of SS (10 µg/ml or 100 µg/ml) for 6 days were washed and resuspended in medium without the drug. The cells were then cultured for 6 days with the numbers of NBT-positive cells determined daily. As shown in FIG. 11A, the percentage of NBT-positive cells remained largely consistent during the 6 day period, demonstrating that SS-induced NB4 differentiation was not reversed in the absence of the drug. Under comparable conditions, ATRA-induced NB4 cell differentiation showed a similar characteristic as previously reported.

To determine whether induction of NB4 cell differentiation requires long term exposure to the drug, NB4 cells were cultured in the presence of the drug (100 µg/ml) for 0.5 to 24 hours, then washed and cultured in medium without the drug for 6 days prior to NBT staining. A linear increase of NBT-positive cells was detected in NB4 cells exposed to the drug for 0.5 to 24 hours with maximal increase (16%) at 24 hours (FIG. 11B). Thus NB4 cell differentiation was inducible following short exposure to the drug. However, the 16% NBT-positive cells induced by exposing to the drug for 24 hours was substantially less than the 52% level in NB4 cells cultured in the presence of SS (100 µg/ml) for 6 days (FIG. 9A). Since the percentage of differentiated cells in the culture was directly related to the length of exposure time to SS (FIG. 9B), the results together indicated that optimal induction of NB4 cell differentiation by SS requires continuous drug exposure. Similarly, NB4 cell differentiation induced by short exposure to the ATRA (FIG. 11B) was modest in comparison to that of long term exposure (FIG. 9B).

SS induces differentiation of HL-60 and U937 cell lines. To investigate whether the differentiation induction activity of SS was unique to NB4 cells, we determined the effect of the drug in AML cell lines HL-60 and U937. HL-60 and U937 cells were cultured in the absence or presence of various amounts of SS for different times. The percentage of NBT-positive cells in the culture was determined as an indicator of cell differentiation.

Figure 12:
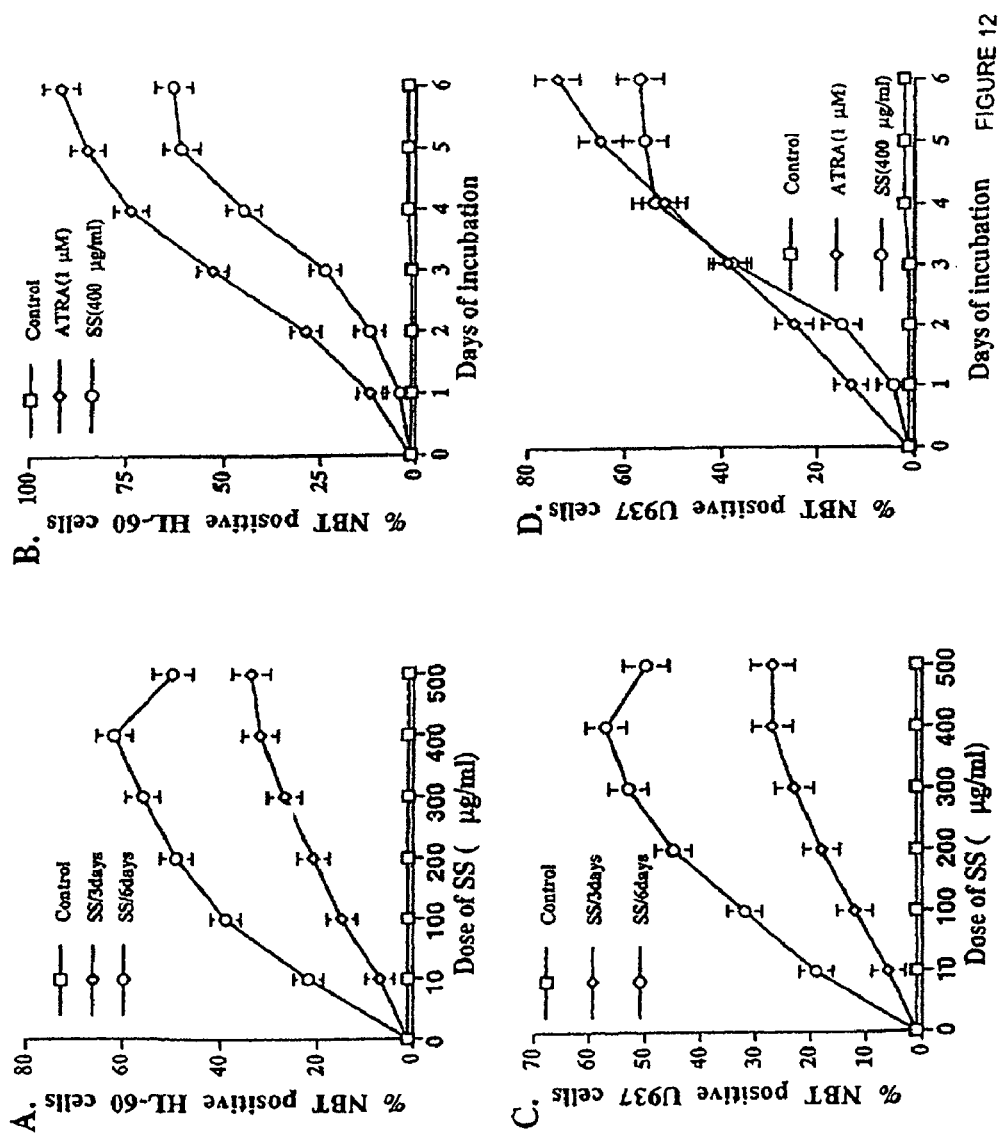
FIG. 12. SS induces differentiation of HL-60 and U937 cells. A. The percentage of NBT-positive cells in HL-60 cells cultured in the absence or presence of various amounts of SS for 3 or 6 days. B. The percentage of NBT-positive cells in HL-60 cultured in the presence of ATRA (1 μM) or SS (400 μg/ml) for 0-6 days. C. Percentage of NBT-positive cells in U937 cells cultured in the absence or presence of various amounts of SS for 6 days. D. The percentage of NBT-positive cells in U937 cultured in the presence of ATRA (1 μM) or SS (400 μg/ml) for 0-6 days. The data represent the mean±SD of triplicate samples.

SS induced differentiation of HL-60 and U937 cells in a dose- and time-dependent manner (FIG. 12). The optimal dosage of SS in inducing differentiation of HL-60 and U937 cells was 400 µg/ml under the experimental conditions in day 6 culture (FIGS. 12A and 4C). At this dosage, the SS-induced differentiation (approximately 60%) of HL-60 and U937 cells was less than that induced by ATRA (90% for HL60 and 72% for U937) in day 6 culture (FIGS. 12B and 4D). Similar to NB4 cells, the percentage of differentiated cells of HL-60 and U937 increased proportionally with prolonged culture in the presence of SS (FIGS. 12B and 12D), indicating a requirement of continuous drug exposure for optimal differentiation induction. The PTPase inhibitor also showed a growth inhibition activity against the two AML cell lines. At the optimal dosage (400 µg/ml) of the drug for differentiation induction in the two cell lines, SS achieved 97% growth inhibition of U937 cells and 63% inhibition of HL-60 cells in day 6 cultures (FIG. 10A).

SS-induced differentiation of HL-60 and U937 is augmented by GM-CSF. Our recent studies showed that SS augments signaling initiated by GM-CSF, which is known to promote myeloid cell proliferation and differentiation. We therefore determined the effect of the drug in combination with the cytokine in inducing differentiation of HL-60 and U937 cells. HL-60 and U937 cells were cultured in the presence of SS (400 µ/ml), GM-CSF (25 ng/ml) or both for 1-6 days with the percentage of NBT-positive cells determined daily.

Figure 13:
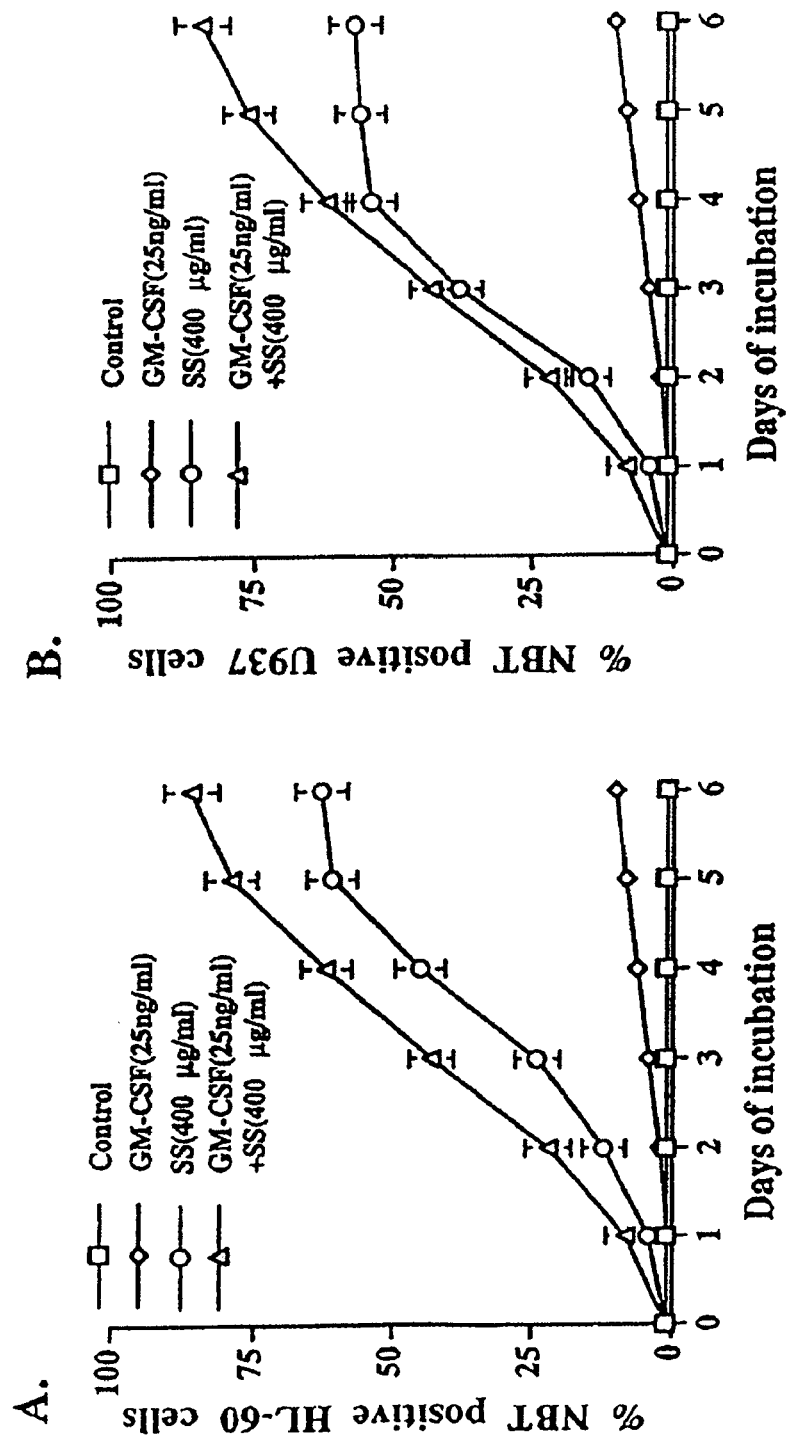
FIG. 13. GM-CSF augments SS-induced differentiation of HL-60 and U937 cells. HL-60 (A) or U937 (B) cells were cultured in the absence or presence of GM-CSF, SS or both for various time points with the percentage of NBT-positive cells determined daily. The data represent the mean±SD of triplicate samples.

SS-induced differentiation of HL-60 and U937 was augmented by GM-CSF to levels nearly equal or higher than those induced by ATRA (FIG. 13). Consistent with previous reports, GM-CSF alone showed a minor effect on HL-60 (FIG. 13A) and U937 (FIG. 13B) differentiation, with maximal increase of NBT-positive cells (8-10%) at day 6. Interestingly, the percentage of NBT-positive cells in HL-60 cultured in the presence of GM-CSF and SS both was increased to 83% comparing to 60% with SS alone (FIG. 13A) or 90% with ATRA alone (FIG. 12B). More dramatically, the combination of GM-CSF and SS in U937 cells induced 80% cell differentiation, which was higher than that of SS alone (55%) (FIG. 13B) or ATRA alone (73%) (FIG. 12D). In contrast, GM-CSF alone showed no detectable effect on NB-4 cell differentiation (data not shown), consistent with a previous report, and failed to augment SS-induced NB4 cell differentiation under comparable conditions (data not shown).

Discussion

Herein we provide the first evidence indicating the potential of PTPase inhibitor SS in differentiation induction therapy in AML treatment. We demonstrate that SS, a drug used for leishmaniasis and a PTPase inhibitor, induces differentiation of AML cell lines NB4, HL-60 and U937 in vitro. Our data showed that SS induces granulocyte-like maturation of NB4, HL-60 and U937 cells as indicated by the increase of NBT-positive cells and by the increased expression of CD11b surface marker (NB4). This differentiation induction activity of the drug was detectable at low dosage of the drug following relatively short exposure. With prolonged exposure at optimal dosages, SS induces differentiation levels of NB4 cells comparable to those induced by ATRA. High levels of differentiation of HL-60 and U937 cells similar to those induced by ATRA were also achieved by optimal dosage of SS in combination with GM-CSF. We further demonstrate that SS-induced differentiation is irreversible and associates with growth arrest and cell death via, probably, apoptosis. These results demonstrate a marked differentiation induction activity of the drug in AML cell lines in vitro and indicate SS as a candidate in differentiation induction therapy in AML treatment.

Our results suggest that SS may be effective in inducing differentiation of AML cells of different FAB classes. This is indicated by its differentiation induction activity in the AML cell lines that represent M3 (NB4 and HL-60) and M5 (U937) subclasses. It is supported by its effect in inducing differentiation of human AML cell line AML-3 (our unpublished data), which represents the M2 subclass. Since SS is a PTPase inhibitor, it is expected that SS induces differentiation via directly targeting a PTPase or PTPases in AML cells. Such a mechanism apparently functions independently of the PML/RARa chimeric protein, a major target of ATRA that is degraded in ATRA-treated NB4 cells. This is evident as SS had no detectable effect on the expression levels of PML/RARa chimeric protein in NB4 cells and did not synergize with ATRA in differentiation induction (our unpublished data). This distinct mechanism of SS in differentiation induction suggests that SS may be particularly useful in AML cases unresponsive or developed resistance to ATRA treatment.

It is likely that the key SS target in AML differentiation is among the PTPases that are relatively insensitive to the drug. This is based on our previous observation of differential sensitivities of PTPases to the inhibitor, with complete inhibition of sensitive PTPases (e.g., SHP-1) by SS at 10 µg/ml and a similar inhibition of insensitive PTPases at more than 100

µg/ml. And it is supported by our data presented here that the optimal dosage of SS in inducing AML cell differentiation is at levels more than 100 µg/ml. In this regard, the involvement of amplification and overexpression of HePTP in AML is interesting and suggests the PTPase as a candidate target of the drug. Characterization of PTPase expression profiles of SS-sensitive and SS-resistant AML cell lines will help to identify the putative PTPase target in AML differentiation.

The optimal dosage of SS for inducing differentiation of NB4 and HL-60/U937 cells is 250 µg/ml and 400 µg/ml respectively. The standard dosage for *leishmania* treatment is 10-20 mg/kg/day resulting in 10 µg/ml or more serum levels. However, higher drug dosages may be clinically achievable and tolerated since doses as high as 80-143 mg/kg had been used in *leishmania* treatment. Nevertheless, even standard dosage of SS may have certain therapeutic benefit as the drug at lower dosages (e.g., 10 µg/ml) showed differentiation induction activity in AML cells (FIGS. 9 and 4). Further studies using mouse models of AML are needed to verify the differentiation induction activity of the drug and to determine the toxicity of the drug at the optimal dosages in vivo.

The observation that GM-CSF augments SS-induced differentiation of HL-60 and U937 suggest the potential clinical use of the two reagents in combination in AML treatment (FIG. 13). Such an interaction between SS and GM-CSF is not unexpected given the activity of the drug in augmenting GM-CSF signaling and the biological effect of the cytokine on myeloid cells. However, combination usage of SS and GM-CSF may only benefit a subgroup of AML cases as a positive interaction between the two reagents in differentiation induction was not detected in NB4 cells, which were not responsive to the cytokine. Moreover, SS may also interact with other cytokines in differentiation induction of AML cells. G-CSF and IFNs were reported to potentiate differentiation of AML cells. Like GM-CSF, the two cytokines signal through the Jak/Stat pathway that could be augmented by SS. The existence of such potential interactions is examined in our ongoing studies.

The demonstrated activity of SS in inducing differentiation of AML cells also suggests the potential of other PTPase inhibitors in inducing AML cell differentiation and in differentiation induction therapy for AML. While most of the known PTPase inhibitors (e.g., sodium vanadate and sodium iodo-acetic acid) are too toxic for clinical application, a number of newly identified PTPase inhibitor are promising. Suramin is a drug used in the treatment of trypanosomiasis and onchocerciasis and was shown recently to be a PTPase inhibitor. It was found to have anti-tumor activity against solid tumors in vitro and in vivo and is currently in clinical trials. Given the marked success of PTK inhibitor STI571 in the treatment of chronic myelogenous leukemia, it is tempting to speculate that PTPase inhibitors may emerge as novel therapeutics for malignant diseases in the near future.

PTPase Inhibitor Sodium Stibogluconate Inhibits the Growth of Human Cancer Cell Lines In Vitro in Synergy with IFNα and IFNβ

SS has potent activity, alone or in combination with IFNα or IFNβ, against cell lines of human malignancies in vitro. SS at therapeutic concentration (10-20 µg/ml) augmented IFNα-induced growth inhibition of cancer cell lines, including DR (lymphoma), U266 (multiple myeloma), WM9 (melanoma), DU145 (prostate cancer) and MDA231 (breast cancer). This activity correlated with enhancement of IFNα-induced Stat1 tyrosine phosphorylation and increased apoptosis. SS also augmented IFNβ-induced growth inhibition of WM9 cells. The interaction of the drug with the IFNs in WM9 cells was shown to be synergistic by median effect analysis. Moreover, SS alone at therapeutic concentration induced substantial growth inhibition in these cell lines. At higher concentrations (25-100 µg/ml) that are tolerated clinically, SS alone or in combination with IFNα, achieved near complete elimination (95-100%) of cancer cell lines that were only partially inhibited by IFNα, demonstrating its marked potential in overcoming IFN-resistance of cancer cells. Characterization of other tumor cell lines resistant to SS indicated that differential sensitivities to SS were unique to individual cell lines instead of tumor type-specific. These results provide the first evidence of a broad anti-cancer activity of SS in vitro, alone or as a synergizer for IFNα/β, and demonstrate its potential in anti-cancer therapies and other cytokine therapies.

We demonstrated that the PTPase inhibitor could augment cell growth responses to hematopoietic growth factors, in part, by enhancing Jak/Stat tyrosine phosphorylation. This activity of the drug is consistent with its inhibition of SHP-1 or other PTPases that down-regulate Jak/Stat tyrosine phosphorylation. Such a functional model of the PTPase inhibitor predicts that the drug may augment cellular responses to all cytokines signaling through the Jak/Stat pathways and is supported by our finding that the drug augments cell responses to IFNα in the hematopoietic cell line TF-1. It also suggested that augmenting signaling of cytokines (e.g., IFNγ) involved in the killing of the intracellular parasite may be an important pharmacological mechanism of the drug.

Importantly, potential novel clinical applications of the drug are suggested by this demonstrated effect of SS in inhibiting SHP-1 and other PTPases and in augmenting cellular responses to hematopoietic growth factors and cytokines. Given the role of SHP-1 in the controlling threshold of antigen responses of T, B and NK cells, the drug might be useful in augmenting immunity against cancers or infectious agents. The drug might also be effective in clinical situations where various hematopoietic growth factors are used. Among clinical applications of cytokines that may benefit from the drug are IFNα and IFNβ used in the treatment of various diseases, including malignancies. Currently, the effectiveness of IFNs in anti-cancer therapies is often limited by IFN-resistance of cancer cells. Drugs that augment IFN-responses of cancer cells may help to overcome such resistance, improve the efficacy of IFN therapies and expand the applications of cytokines in cancer treatment. In light of the pivotal role of PTPases in cell proliferation and viability, it is also possible that the PTPase inhibitor as a single agent may function as an anti-cancer drug by targeting PTPases essential for cancer cells.

To explore the potential of SS as an anti-tumor drug, we have determined its effect on the growth of various human cancer cell lines in vitro. Our data demonstrate that the PTPase inhibitor, used alone or in combination with IFNα and IFNβ, was effective in inhibiting the in vitro growth of different human cell lines of lymphoma, multiple myeloma, leukemia, melanoma, prostate cancer, breast cancer, renal cancer and bladder cancer. Moreover, we show that this anti-cancer activity of the drug was related to the enhancement of tyrosine phosphorylation of specific cellular proteins and the induction of cell apoptosis. The effectiveness of the drug in overcoming IFN-resistance of cancer cells was indicated by the near complete killing by SS alone or in combination with IFNα of cancer cell lines that showed only partial growth inhibition in response to the cytokine. The broad in vitro anti-cancer activity of the PTPase inhibitor indicates its potential as a novel anti-cancer drug as a single agent or in combination with IFNα/β. Moreover, the ability of the drug to augment Jak/Stat signaling via targeting Jak/Stat PTPase (s) suggests its effectiveness in other therapies of hematopoietic growth factors and cytokines that signal through the Jak/Stat pathway.

Methods

Reagents. Recombinant human IFNα (IFNa-2b, specific activity 2×10^8 units/mg protein, Schering Plough) and sodium stibogluconate have been described previously. Recombinant human IFNβ (specific activity 2×1×10^8 unites/mg protein) was from Serono pharmaceutics. Antibodies for phosphotyosine Stat1 and Stat1 (New England BioLab Inc., Beverly, Mass.), SHP-1 and phosphotyrosine (Santa Cruz Biotechnology, Santa Cruz, Calif.), β-actin (Pharmacia, Arlington Heights, Ill.) were purchased from commercial sources as indicated.

Cells, cell culture and cell proliferation assays. Human cell lines were maintained in RPMI 1640 or DMEM medium supplemented with 10% fetal calf serum (FCS) at 37° C. DS and DR (Fan Dong, the Cleveland Clinic Foundation (CCF)), U266, DU145 and C42 (Alex Almasan, CCF), Peer (John Winfield, University of North Carolina), H9 (ATCC), WM9 and WM35 (Ernest Borden, CCF), MDA231 and MDA435 (Graham Casey, CCF), WiT49-N1 (Bryan Williams, CCF), RC45 and 5637 (S. K. Bandyopadhyay, CCF) were employed in the studies.

For cell proliferation assays, cells were grown in 10% FCS culture medium containing various amounts of IFNs and/or SS in 96 well plates and cultured at 37° C. for 3 or 6 days as indicated. The numbers of viable cells in proliferation assays were determined by MTT assays as described previously.

Drug Interaction Analysis. Median effect analysis, which provides the most general form of studying the interactions between drugs, was utilized to analyze the interaction between SS and IFNα or IFNβ. Since details regarding the mode of IFN and SS interaction are not fully understood, and whether or not they act in a mutually exclusive fashion, we chose the most general analysis available. Dose response curves were generated for each drug alone, and also the combinations. Median effect plots were generated, which determined m and $D_m$ values for IFN alone, SS alone, and the combination. The combination index (CI) was determined and plotted vs. fraction affected (FA). Data were analyzed in both modes, mutually exclusive and mutually nonexclusive. The interaction between two mutually nonexclusive drugs is described by the Equation $CI=D_1/D_{x1}+D_2/D_{x2}+D_1D_2/D_{x1}D_{x2}$, where $D_{x1}$ and $D_{x2}$ are the doses of drug 1 and drug 2 that are required to inhibit growth x %. $D_1$ and $D_2$ in combination also inhibit growth x % (i.e. drug 1 and drug 2 are isoeffective). When CI<1, drugs are synergistic, when CI=1, drugs are additive, and when CI>1, drugs are antagonistic.

Detection of apoptotic cells by Annexin V/Propidium Iodide assay. Annexin V staining of exposed membrane phospholipid phosphatidylserine (PS) was done using the Annexin V assay kit (Pharmingen, San Diego, Calif.). Briefly, U266 or WM9 cells were cultured in the 10% FCS RPMI 1640 medium in the absence or presence of SS, IFNα or both for 3 days. Cells were then washed in PBS twice and stained in binding buffer (10 mM Hepes, pH 7.4; 140 mM NaCl; 2.5 mM CaCl2) containing Annexin V-FITC and propidium iodide for 15 min. The reaction was stopped by adding 10 volumes of binding buffer and analyzed by FACS (Becton Dickinson Facsvantage) or fluorescence microscopy.

Induction of Stat1 tyrosine phosphorylation by IFNα and/or sodium stibogluconate. For induction of Stat1 tyrosine phosphorylation by IFNα in the absence or presence of SS, cells grown in 10% FCS RPMI 1640 medium at 37° C. were stimulated with IFNα (50 u/ml) for various time points and treated with or without SS for 5 minutes prior to termination by lysing the cells in cold lysis buffer (1% NP-40; 50 mM Tris, pH 7.4; 100 mM NaCl; 1 mM EDTA, 10% glycerol, 10 mM sodium molybdic acid and 4 mM AEBSF).

Cell lysate preparation, SDS-PAGE and Western blotting. Cell lysates were prepared by lysing cells in cold lysis buffer for 30 min and cleared by centrifuging at 14,000 rpm at 4° C. for 15 min. For SDS-PAGE, cell lysates were mixed with equal volume of 2×SDS-PAGE sample buffer, heated at 90° C. for 5 min and separated in 10% SDS-PAGE gels. Cellular proteins in SDS-PAGE gels were transferred to nitrocellulose membrane (Schleicher & Schuell), blocked in 5% milk, probed with antibodies and detected by using an enhanced chemiluminescence kit (ECL, Amersham).

Results

SS Inhibits the In Vitro Growth of Human Cell Lines of Hematopoietic Malignancies and Augments IFNα-Induced Cell Growth Inhibition.

Figure 14:
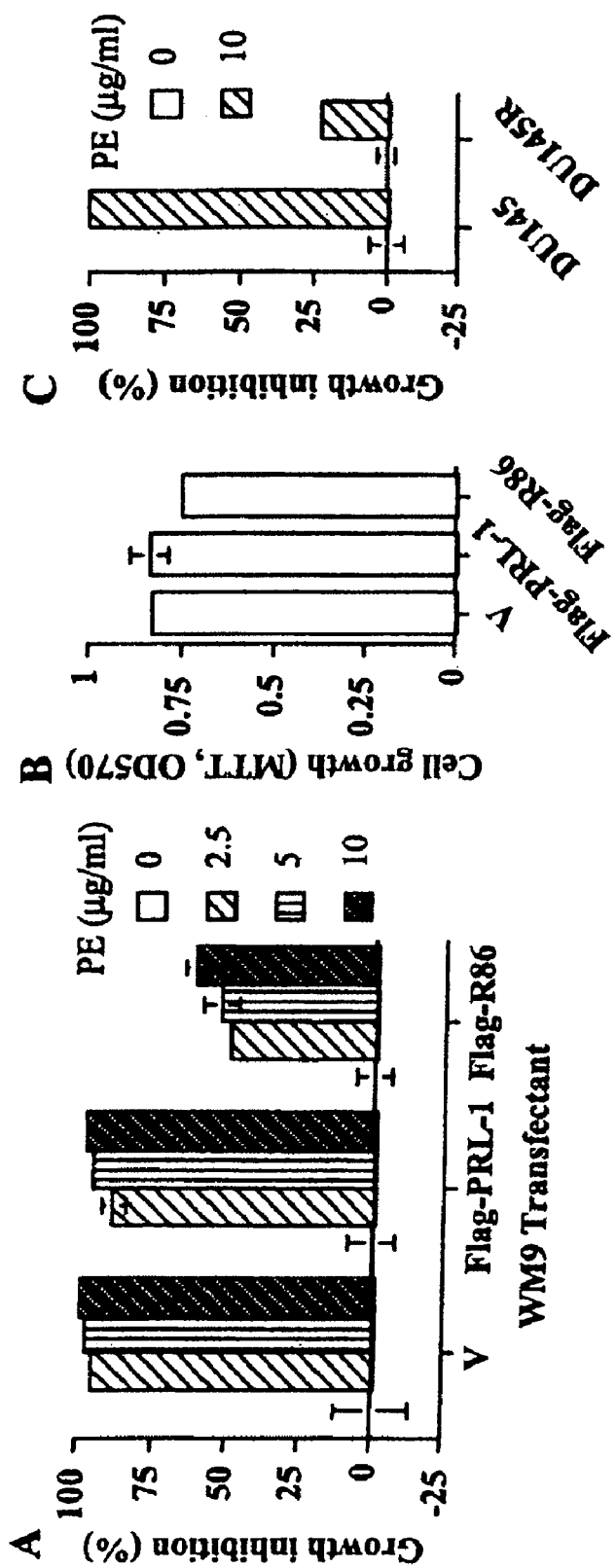
FIG. 14. Growth inhibition of human cell lines of hematopoietic malignancies by SS and/or IFNα. A and B. Growth of DS and DR cells cultured in the absence or presence of various amounts of SS and/or IFNα (1,000 u/ml) for 3 days was measured by MTT assays. C. Percentage of growth inhibition of DR cells calculated from data in B. D. Percentage of growth inhibition of DR cells by IFNα (1,000 u/ml) and various amounts of SS in day 6 cultures measured by MTT assays. E. Percentage of growth inhibition of U266 cells by IFNα (1,000 u/ml) and various amounts of SS in day 6 cultures as measured by MTT assays. The data represent the mean±SD values of triplicate samples.

SS markedly augmented IFNα-induced growth inhibition of the IFNα-resistant lymphoma cell line DR. DR and DS cell lines were derived from the parental human lymphoma cell line Daudi and were resistant or sensitive to IFNα respectively. Consistent with their sensitivity to IFNα, DS cells cultured in the presence of IFNα (1,000 u/ml) were almost completely eliminated by day 3 (FIG. 1A). In contrast, IFNα treatment resulted in only 19% growth inhibition of the DR cells (FIGS. 14B and C). Importantly, this IFNα-induced DR cell growth inhibition was increased to 46-69% in the presence of various amounts of SS (FIGS. 14B and C). Augmentation of IFNα-induced growth inhibition by SS was also observed in prolonged culture of DR cells for 6 days (FIG. 14D), in which the 39% of IFNα-induced growth inhibition was increased to 80% and 92% in the presence of SS at 12.5 µg/ml and 25 µg/ml respectively. Interestingly, the PTPase inhibitor by itself showed a marked activity against DR cells at higher dosages: it almost completely eliminated proliferation of DR cells (95-99%) in the day 6 culture at 50 µg/ml and 100 µg/ml as a single agent (FIG. 14D). SS by itself showed a modest activity against the DS cells (FIG. 1A).

This initial observation of marked growth inhibition of DR cells by SS alone or in combination with IFNα prompted us to determine its effect against other cell lines of human hematopoietic malignancies. U266 is cell line of human multiple myeloma, a disease currently treated with IFNα. Again, augmentation of IFNα-induced cell growth inhibition of U266 cells was detected with a substantial growth inhibition activity of the drug by itself (FIG. 14E). Various degrees of augmentation of IFNα growth inhibition activity by SS were also observed in other cell lines of T-lymphoma (H9) and T-ALL (Peer) (Table 1).

SS inhibits the in vitro growth of human cell lines of non-hematopoietic malignancies and augments IFNα-induced growth inhibition. The effect of SS in augmenting IFNα-induced growth inhibition and in causing growth inhibition by itself in cell lines of human hematopoietic malignancies suggested potential activity of the drug against non-hematopoietic cancer cells as the drug has inhibitory activity against PTPases (e.g., PTP1B and SHP-2) that express in various non-hematopoietic tissues.

Figure 15:
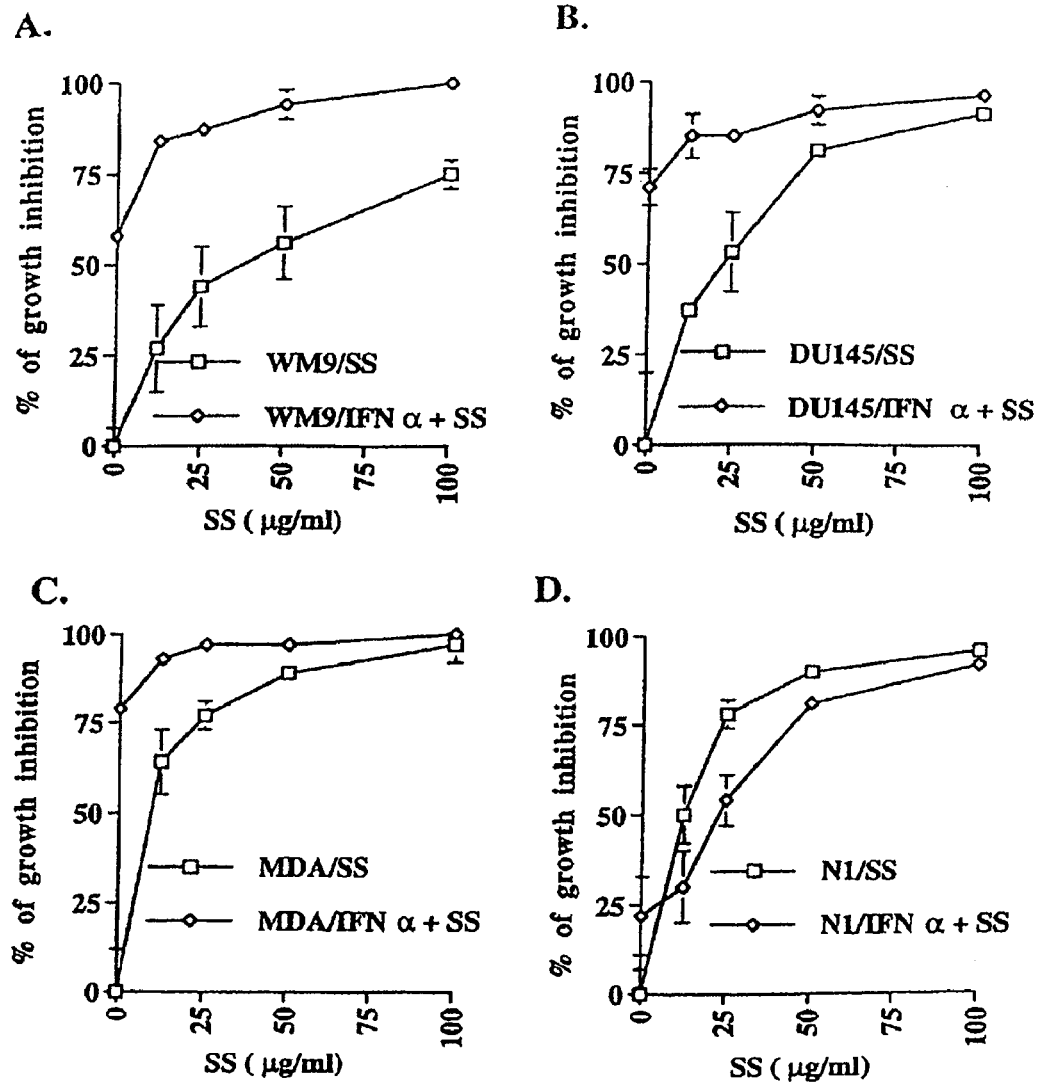
FIG. 15. Growth inhibition of human cell lines of non-hematopoietic malignancies by SS and/or IFNα. Percentage of growth inhibition of WM9 (A), DU145 (B), MDA231 (C) and WiT49-N1 (D) in the absence or presence of various amounts of SS and/or IFNα (1,000 u/ml) in day 6 cultures as measured by MTT assays. The data represent the mean±SD values of triplicate samples.

Several solid tumor cell lines were found to be sensitive to the PTPase inhibitor alone or in combination with IFNα. IFNα-induced growth inhibition of WM9 (melanoma), MDA231 (breast cancer) and DU145 (prostate cancer) was augmented by sodium stibogluconate (FIGS. 15A, B and C). Like the DR lymphoma cell line, these tumor cell lines were sensitive to the PTPase inhibitor as a single agent, which at 50 µg/ml and 100 µg/ml dosages killed all cells in day 6 culture (FIG. 15). The Wilms tumor cell line WiT49-N1 was also sensitive to SS although its growth inhibition activity was not enhanced by IFNα (FIG. 15D).

Further studies of the drug in additional cell lines demonstrated that sensitivity to SS was not tumor type-specific but unique to individual cell lines. In contrast to the sensitive WM9 melanoma cell line, the WM35 melanoma cell line was minimally affected by SS (Table 1). Unlike the DU145 prostate cancer cell line, the C42 prostate cancer cell line was highly resistant to the inhibitor (Table 1). Growth responses of several other human tumor cell lines to IFNα and/or SS were also determined (Table 1).

SS augments IFNα- and IFNβ-induced growth inhibition of WM9 cells in a synergistic manner. To further investigate whether augmentation of IFNα-induced cell growth inhibition by SS was unique to this drug combination, we compared the effect of the drug on IFNα- or IFNβ-induced growth inhibition of the WM9 cell line of human melanoma, which is currently treated by the cytokines.

Figure 16:
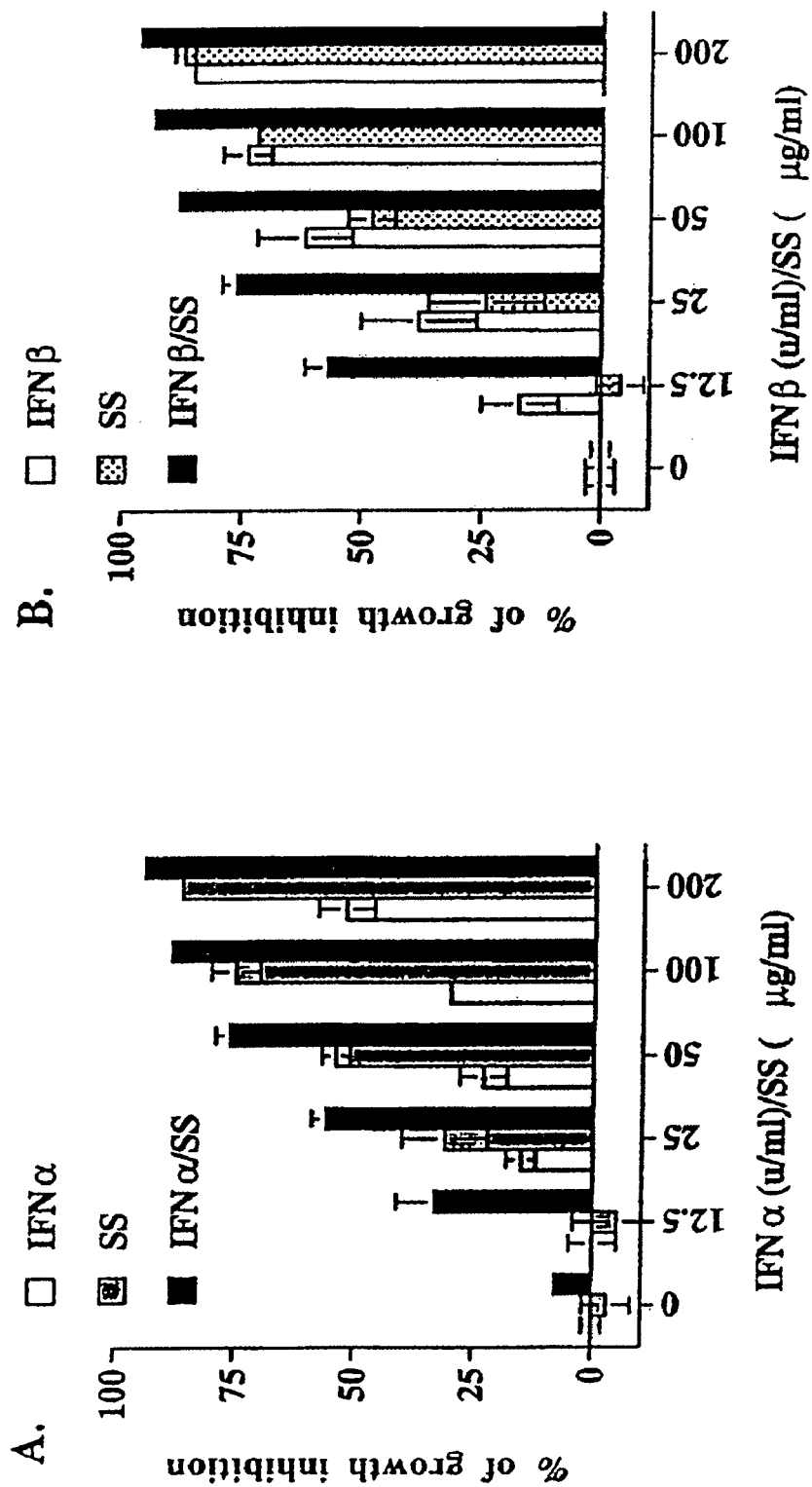
FIG. 16. SS augments both IFNα- and IFNβ-induced growth inhibition of WM9 cells. Percentage of growth inhibition of WM9 cells in the absence or presence of various amounts of SS, IFNα and IFNβ in day 6 cultures as measured by MTT assays. The data represent the mean±SD values of triplicate samples.

The growth of WM9 cells was suppressed by IFNα (FIG. 16A) and, more potently, by IFNβ (FIG. 16B). In the presence of SS, IFNα- and IFNα-induced growth inhibition was greatly enhanced (FIG. 16). This augmentation of IFNα/β-induced growth inhibition by SS was most dramatic at lower dosage levels of SS (12.5-50 µg/ml) and the IFNs (12.5-50 u/ml) but was also detectable in the higher dosage range (FIG. 16). Thus, SS was effective in augmenting the growth inhibition activity of IFNα and IFNβ against WM9 cells.

Figure 17:
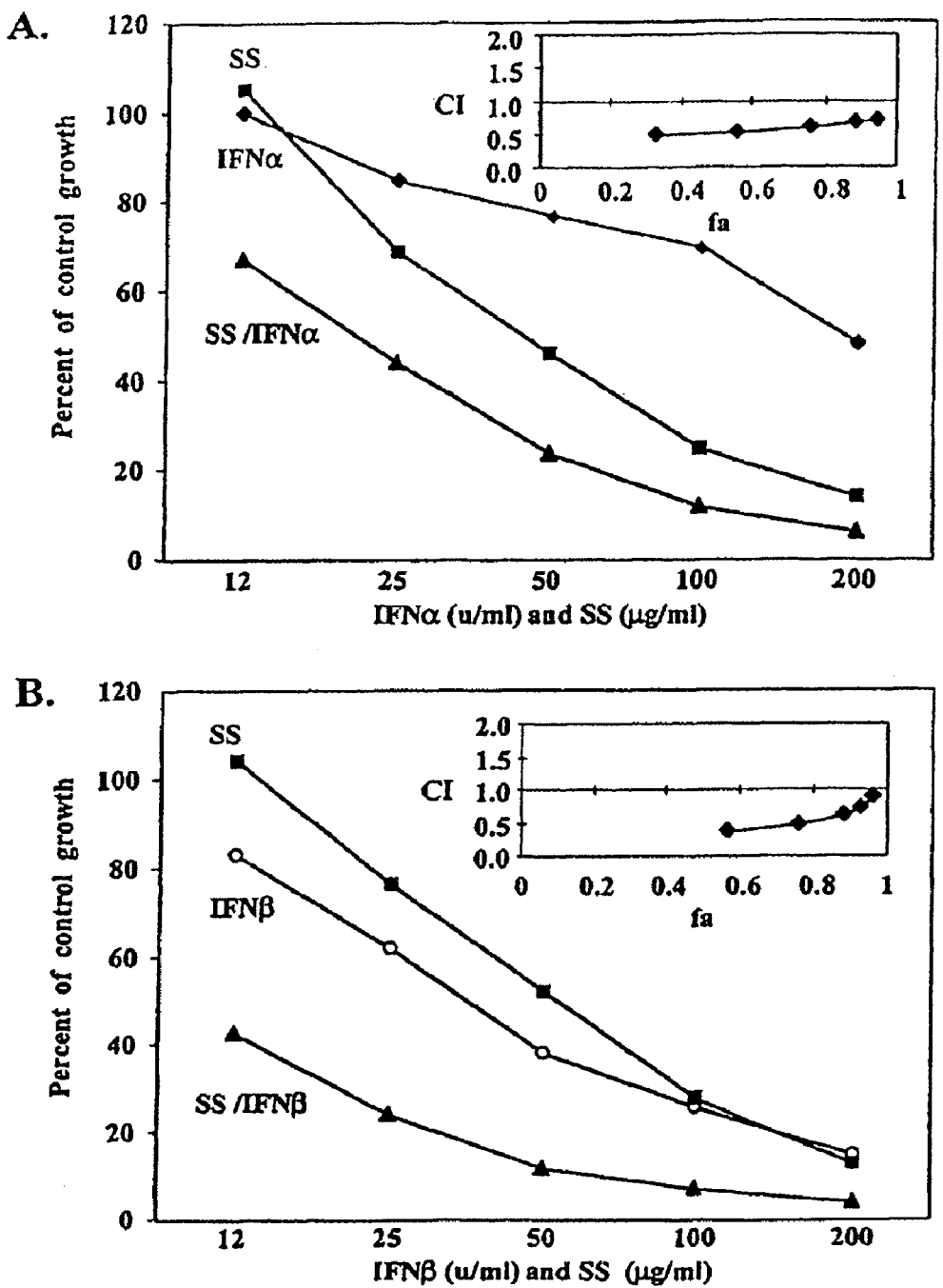
FIG. 17. SS interacts with IFNα and IFNβ in a synergistic manner in growth inhibition of WM9 cells. Data from MTT antiproliferative assays was expressed as percent control growth (PCG) of treated cells, compared to untreated cells (100%). Median effect analysis (inset graphs), similar to isobol analysis, defined drug interaction in the IFNα+SS and the IFNβ+SS combinations as synergistic at all doses tested, characterized by a combination index (CI) of less than 1. Additivity is indicated by CI=1, and antagonism occurs when CI>1. Fraction affected (fa)=(100−PCG)/100.

To determine the nature of the drug interaction in the IFNα/SS and IFNβ/SS combinations, data in FIG. 16 were subject to median effect analysis to derive combination index (CI) values that define drug interaction as synergy (CI<1), additivity (CI=1) or antagonism (CI>1). The results, calculated in both modes of mutually exclusive and nonexclusive, demonstrate that the drug interaction in the combinations of IFNα/SS (FIG. 17A) and IFNβ/SS (FIG. 17B) are synergistic at all doses tested, characterized by a CI value less than 1. Since the growth inhibition of DR, DU145 and MDA231 cells achieved by the combination of SS and IFNα was similar to that of the WM9 cells (FIGS. 14 and 2), the results also suggested a synergistic interaction for the two agents in those cell lines.

Growth inhibition of human cancer cell lines by SS associates with induction of apoptosis. The marked growth inhibition of tumor cell lines by SS alone and/or in combination with IFNα indicated induction of cell death by the PTPase inhibitor. We therefore determined numbers of apoptotic cells of U266 and WM9 cell lines grown in the presence of SS, IFNα or both.

Figure 18:
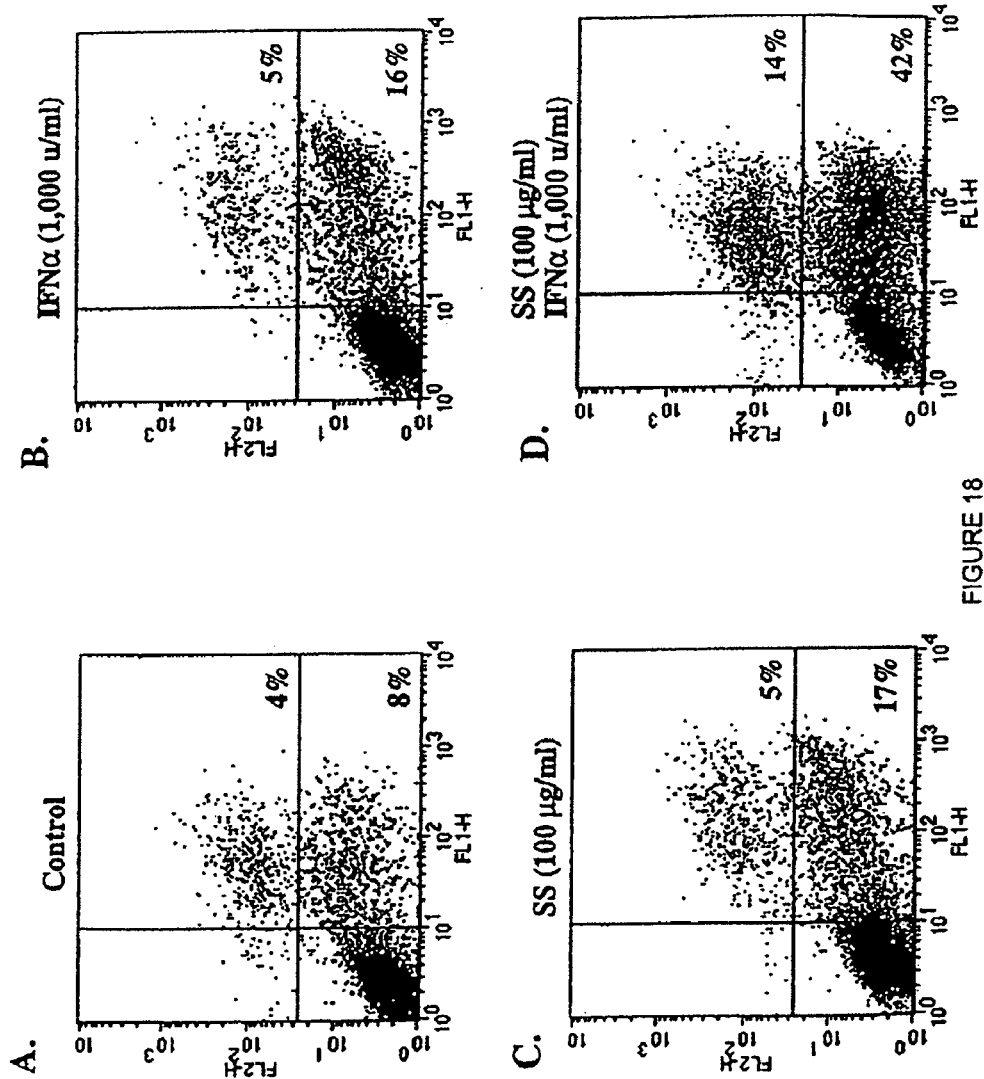
FIG. 18. Induction of U266 cell apoptosis by SS and/or IFNα. U266 cells cultured for 3 days in the absence (A) or presence of IFNα (B), SS (C) or both (D) were stained by Annexin V FITC(X-Axis) and Propidium iodide (PI, Y-Axis). Flow cytometric plots show binding of annexin V, indicating exposure of phosphatidylserine residues on the cell membrane (early stages of apoptosis), and PI labeling, indicating membrane permeabilization (late-stage cell death).

Increased apoptosis of U266 cells was detected in the presence of SS alone and, more dramatically, of the inhibitor and IFNα both (FIG. 18). In the presence of SS (100 µg/ml), the percentage of apoptotic cells was increased to 17% from 8% (control). IFNα (1000 u/ml) induced 16% apoptosis. When both sodium stibogluconate and IFNα were present, the number of apoptotic cells increased to 42%. Evaluated by fluorescent microscopy, WM9 cells in the presence of SS, IFNα or both were increased to 11%, 15% or 31% respectively from 5% (control). Thus, growth inhibition of these tumor cell lines by SS and IFNα was mediated at least in part by inducing apoptosis.

Augmentation of IFNα-induced cell growth inhibition by SS correlates with enhanced Stat1 tyrosine phosphorylation. To investigate the signaling mechanism of SS in augmenting IFNα-induced cell growth inhibition, we determined the effect of SS on IFNα-induced tyrosine phosphorylation of Stat1 which clearly mediates the anticellular effects of the cytokine.

IFNα-induced Stat1 tyrosine phosphorylation was enhanced in the presence of SS in cell lines (DR, WM9 and DU145) in which a synergy of IFNα and SS in growth inhibition was detected (FIG. 1-4). In the absence of SS, Stat1 tyrosine phosphorylation in DR cells was induced by IFNα within 30 min and decreased by 5 hours post-stimulation (FIG. 19A, lanes 1-3). In the presence of SS (10 µg/ml), Stat1 tyrosine phosphorylation at 30 min post-stimulation was approximately two folds greater than control (FIG. 19A, lane 2 and 5) and remained elevated for 5 hours (FIG. 19A). Enhanced Stat1 tyrosine phosphorylation at 5 hours post-stimulation by IFNα was also detected in WM9 and DU145 cell lines cultured in the presence of SS (FIG. 19B). In contrast, SS failed to enhance IFNα-induced Stat1 tyrosine phosphorylation in WM35 and WiT49-N1 cell lines (FIG. 19B) in which no antiproliferative synergy between IFNα and SS was detected (Table 1 and FIG. 15D). In the absence of IFNα, SS failed to induced Stat1 tyrosine phosphorylation by itself in DR cells (FIG. 19A). IFNα-induced Stat1 tyrosine phosphorylation in WiT49-N1 cells was not increased in the presence of SS (FIG. 19B).

Figure 19:
FIG. 19. SS enhanced IFNα-induced Stat1 tyrosine phosphorylation of human cancer cell lines. A. Total cell lysate of DR cells stimulated by IFNα for various time points in the absence or presence of SS were separated in SDS-PAGE gels, transferred to nitrocellulose membrane and probed with antibodies as indicated. B. Total cell lysate of human cancer cell lines stimulated by IFNα for 5 hours in the absence or presence of SS were separated in SDS-PAGE gels, transferred to nitrocellulose membrane and probed with antibodies as indicated.
Figure 19:
Figure 19:
Figure 19:
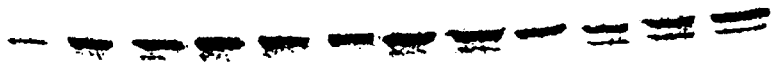
Figure 19:
Figure 19:

To assess the involvement of SHP-1, which is known to regulate Jak/Stat phosphorylation in hematopoietic cells, we determined the expression of the PTPase in the tumor cell lines (FIG. 19). As expected, SHP-1 protein was easily detected in DR cells (FIG. 19A). However, SHP-1 protein was undetectable in the two melanoma cell lines although it was present in the Wilms tumor cell line (WiT49-N1) and the prostate cell line (DU145) (FIG. 19B). Thus, the enhancement of IFNα-induced Stat1 tyrosine phosphorylation in WM9 cells occurred in the absence of SHP-1 and may be mediated by other PTPases sensitive to the PTPase inhibitor.

Discussion:

Resistance of cancer cells to IFNα and IFNβ is a major problem that limits the clinical application of these cytokines in anti-cancer therapies. Although the mechanism of IFN-resistance of cancer cells is not fully understood, reduced IFN signaling is often detected in cancer cells and believed to be an important factor. Therapeutic reagents that augment IFN signaling may help to overcome such resistance in cancer cells but have not been reported yet.

Herein we provide evidence that SS, a drug used for leishmaniasis and a PTPase inhibitor, augments IFN signaling and can overcome IFN-resistance in various human cancer cell lines. Augmentation of IFNα signaling by the drug was clearly demonstrated by its enhancement of IFNα-induced Stat1 phosphorylation. This activity was detectable at its therapeutic concentration (10-20 µg/ml) that is clinically well tolerated. Moreover, the activity of the drug in augmenting of IFNα signaling was effective in overcoming IFN-resistance as it was accompanied by augmentation of IFNα-induced growth inhibition of various human cancer cell lines.

The drug at 25-100 µg/ml was extremely effective at overcoming IFN-resistance of cell lines that were only partially inhibited by IFNα as a single agent. This was well-illustrated by the complete elimination of WM-9 melanoma cells by the drug and IFNα in combination while the two agents individually achieved only 75% and 58% growth inhibition respectively. Similarly, the drug at 25 µg/ml combined with IFNα achieved near complete elimination of MDA231 breast cancer cells compared to 65% and 79% growth inhibition by the two agents individually. This in vitro anti-cancer activity of the drug alone or in combination with IFNα was shown to involve induction of apoptosis in WM9 cell and U266 cells. Although the standard dosage for *leishmania* treatment is 10-20 mg/kg/day resulting in 10 µg/ml or more serum levels, higher drug dosages may be clinically achievable and tolerated. Doses as high as 850 mg/kg/day have been used in *leishmania* treatment.

Our finding that SS also augmented IFNβ-induced growth inhibition suggests that the drug may improve the efficacy of IFNβ therapies in the treatment of cancer as well as several other diseases (e.g., hepatitis B and multiple sclerosis) that are currently treated with the cytokine. Moreover, it provided additional evidence that among the targets of the PTPase inhibitor are Jak/Stat PTPases which down regulate cytokine signaling by dephosphorylating Jak/Stat proteins, a hypothesis based on our previous finding of drug augmentation of cell responses to IL-3 and GM-CSF that signal through the Jak/Stat pathway like the IFNs. PTPase SHP-1 and CD45 are known to down-regulate Jak/Stat tyrosine phosphorylation in hematopoietic cells. As the expression of SHP-1 (FIG. 19B, lane 1-3) and CD45 (our unpublished data) was not detectable in WM9 cells in which IFNα-induced Stat1 phosphorylation was augmented by the drug, our results indicate the existence of other Stat1-regulatory PTPase(s) as the drug target in these cells. But the data does not exclude the involvement of SHP-1 or CD45 as drug targets in hematopoietic cells. This mechanism of the drug targeting Jak/Stat PTPase(s) predicts that the PTPase inhibitor will have a similar activity in augmenting the signaling of other cytokines signaling through the Jak/Stat pathway. Many cytokines signaling through Jak/Stat pathway (e.g., IL-2, IL-4, and IL-12) have been used in anti-cancer therapies, which may be improved in combination with the PTPase inhibitor.

The interaction of SS with IFNα and IFNβ in growth inhibition of WM9 melanoma cells was clearly synergistic. Such a synergy between the drug and IFNs is consistent with the augmentation of IFN-induced Stat1 phosphorylation by the PTPase inhibitor. Although several other drugs have been shown to synergize with IFNs, SS is the first one that works through targeting molecules in the IFN signaling pathway. It remains to be determined whether the demonstrated in vitro synergy between SS and IFNα/β is reproducible in vivo in animal models and in clinical treatment. These are important issues that are under investigation.

Our results also provided the first evidence that the drug alone had marked growth inhibitory activity against human cancer cell lines in vitro. This activity was most dramatic at higher dosages (25-100 μg/ml) with a substantial activity detectable at therapeutic concentration. For instance, SS at 100 μg/ml achieved complete or near complete killing of cells in day 6 culture of the DR, DU145, MDA231 and WiT49-N1 cell lines. Induction of cell apoptosis may play a role in the killing of the cancer cells as indicated by the increased apoptosis of WM9 and U266 cells in the presence of SS at 100 μg/ml. Unlike the synergy of the drug at therapeutic concentration with IFNs that was mediated via targeting Jak/Stat PTPases to augment IFN-induced Jak/Stat phosphorylation and -signaling, this activity of drug is likely mediated by other PTPases independent of the Jak/Stat pathway as indicated by the failure of the drug alone to induce Stat1 phosphorylation at 10 μg/ml (FIG. 19A, lane 4) or at higher concentration (our unpublished data). More detailed analysis of SS-sensitive cells to identify cellular proteins whose tyrosine phosphorylation are affected by the drug alone in drug-sensitive cells may help to elucidate the underlying mechanism.

The sensitivity of certain human cancer cell lines to the drug by itself suggests potential effectiveness of SS as a single agent in cancer treatment. In this regard, our finding that drug sensitivity is unique to individual cancer cell lines instead of tumor type-specific underscores the importance of identification of markers of drug-sensitivity and -resistance in cancer cells. It is likely that drug-resistance may be due to the absence of target PTPases or PTPase substrates in drug-resistant cells which have adapted to grow without these molecules. In this regard, it is interesting that differential expression of PTPases in the sensitive WM9 and resistant WM35 melanoma cell lines was detected by gene expression profiling (Ernest Borden/T. Yi, unpublished data). Additional studies are clearly needed in this area and could have important clinical significance.

Pentavalent Antimony or an Agents Ability to Inhibit Leishmaniasis Appears to be a Strong Predicator of that Agent's Effectiveness as a PTPase Inhibitor SS as a PTPase inhibitor with anti-cancer activity suggests the possibility of several SS-related drugs, and other compounds containing pentavalent antimony or identified as effective agents in the treatment of leishmaniasis, may have a similar activity against PTPases and potential as novel anti-cancer therapeutics A very good review of agents effective in the treatment of leishmaniasis is found in Steck, E. A. The leishmaniases, Prog Drug Res, 18: 289-251 (1974). Particular reference is directed to pages 306-315 which describe antimonates. These drugs include meglumine antimonate, antimony dextran glucoside, antimony mannan, ethyl stibanine and urea stibamine. They are known to have anti-*leishmania* activities but are less used clinically since the preferred drug (SS) has more satisfactory stability, better profile of tolerance and efficacy. Like SS, all of them contain pentavalent antimony which is complexed with different organic moieties in these drugs. Since pentavalent antimony is known to interact with sulfhydryl groups in proteins and that a sulfhydryl group in a conserved cysteine residue in PTPases is required for PTPase activity, it is likely that SS inhibition of PTPases is mediated via modification of the sulfhydryl group in PTPases by the pentavalent antimony in SS. Therefore SS-related drugs (or other compounds) containing pentavalent antimony may inactivate PTPases in a similar manner as a major mechanism of their anti-*leishmania* effect. They may therefore also have activities in augmenting cytokine signaling and against cancer cells via targeting PTPases or other cellular components. Because different organic moieties in each of the drugs make them structurally different from that of SS, these drugs may selectively target different groups of PTPases and consequently may have activity against different types of cancer cells. Currently, there is no report regarding their activity against PTPases, in cytokine signaling or as anti-cancer reagents. Although potassium antimony tartrate has no detectable activity against PTPases, the marked activity of the trivalent antimony in growth inhibition of Baf3 cell line suggests this type of chemical compounds may also have anti-cancer activity via a mechanism independent of PTPases.

Figure 20:
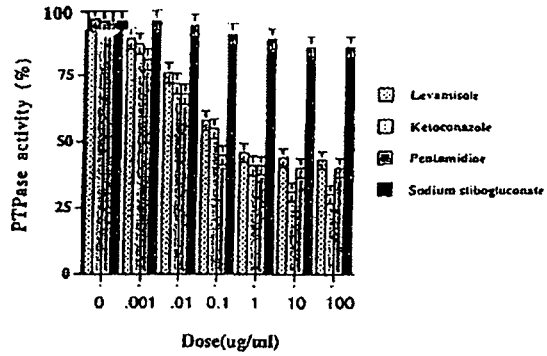
FIG. 20.
Figure 20:
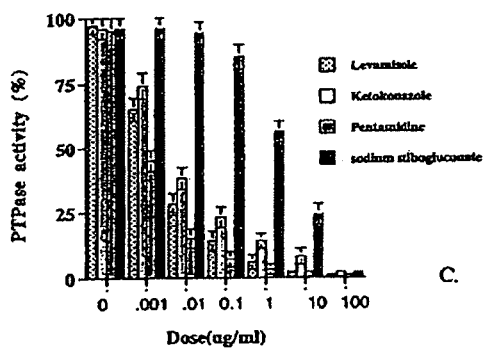
Figure 20:
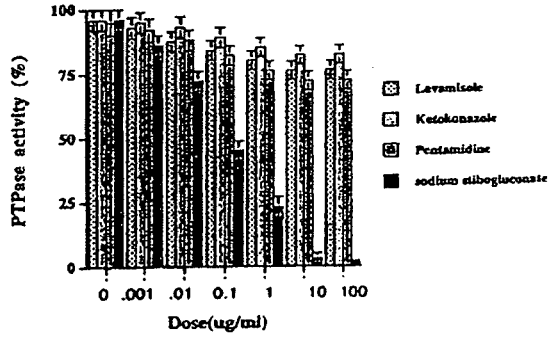

Pentavalent antimony compounds appear to be particularly well-suited for purposes of the present invention. FIG. 20A-C illustrates the chemical structure for three pentavalent antimony agents.

FIG. 21A-C illustrate the inhibition of PTPase activity with regard to Levamisole, Ketoconazole, and Pentamidine with Sodium Stibogluconate serving as a model agent.

Figure 21:
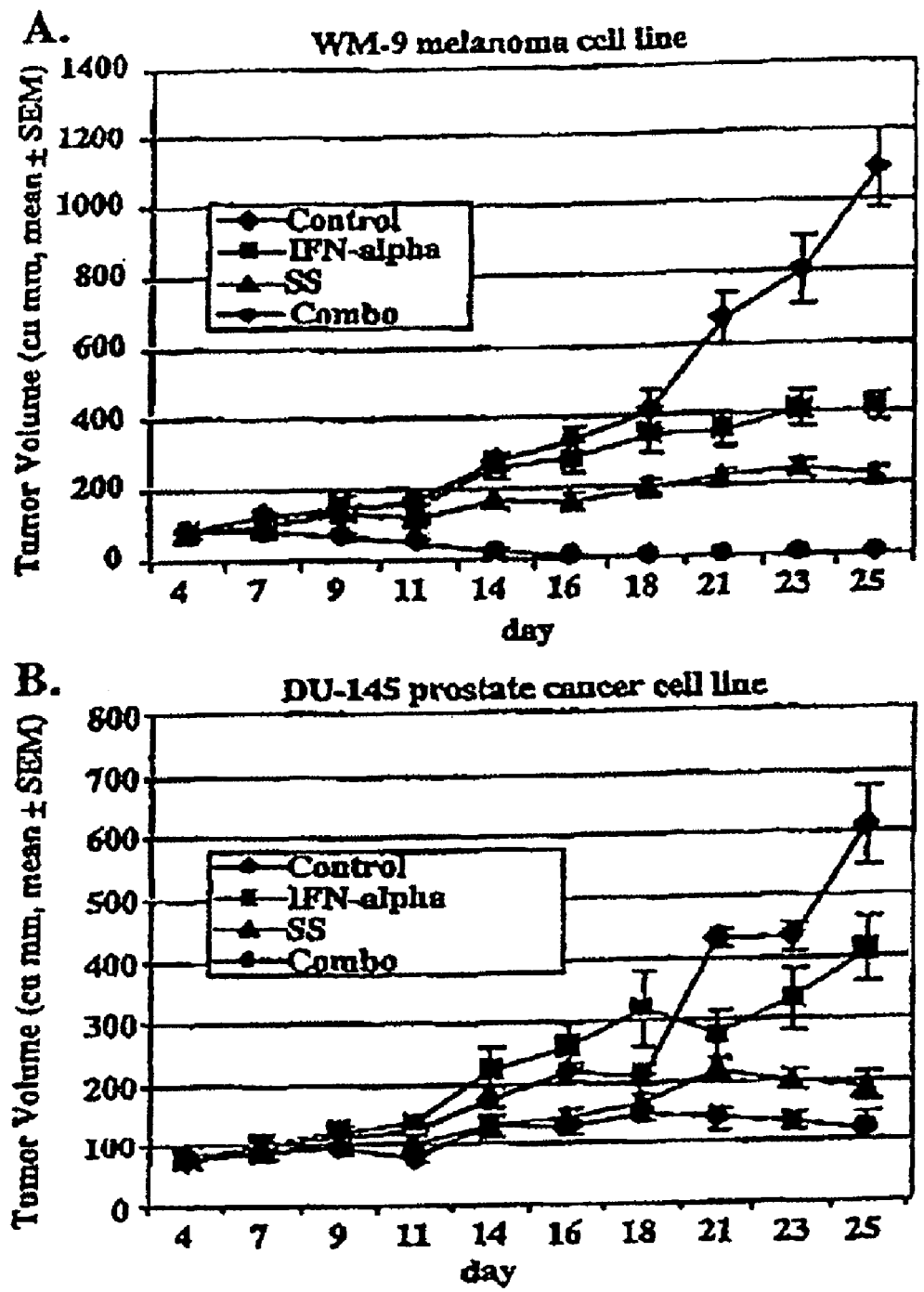
FIG. 21.

As shown in FIG. 21, Levamisole, Pentamidine and Ketoconazole inhibits the activity of PTP1B in vitro. Their activity against the enzyme is stronger than that of SS since less amounts of these drugs are required to achieve near complete inhibition of the enzyme.

Pentamidine, Ketoconazole and Levamisole are novel inhibitors of PTPases in vitro. This observation indicates that their analogous or derivatives may also function as PTPase inhibitors. Moreover, their chemical structures are distinct from that of SS and therefore provide novel bases to design and develop related compounds against PTPases. Like SS, these drugs may also have novel clinical applications by targeting cellular PTPases, which are crucial in intracellular signaling.

There are well over 100 PAPases in the human body. FIG. 21A-C illustrates the specificity (which is anticipated to be disease specific) of the agents employed therein. Specificity is desired to avoid unwanted activity and/or toxicity.

SS Synergizes with IFNα to Eradicate Human Melanoma WM9 Tumors and Markedly Suppress Human Prostate Carcinoma DV145 Tumors in Nude Mice.

Our preliminary studies described above clearly demonstrate a marked activity of PTPase inhibitor SS against various cancer cell lines in vitro. We next tried to address the critical issue whether the drug has anti-cancer activity in vivo at a dosage that is clinically achievable and tolerated. For this, we determine the efficacy of SS, as a single agent or in combination with IFNα, against human melanoma WM9 and human prostate carcinoma DLJ145 xenografts in nude mice.

Methods

We chose WM9 and DU145 cell lines for the study based on the following considerations:

the two cell lines were found in our preliminary study to be sensitive to SS as a single agent or in combination with IFNα; (FIG. 15A-B)

both cell lines are known to be tumorigenic in nude mice;

the cell lines represent human malignancies that are major health threats with no effective treatment;

IFNα is used in the treatment of melanoma and prostate cancer with modest outcome, which may be significantly improved by combinational therapy with SS that synergize with the cytokine.

We treated nude mice bearing WM9 or DU145 xenografts with IFNα (500,000 U, s_c., daily), SS (12 mg Sb, s.c., daily) or both. The amount of IFNα used for the treatment is comparable to the dosages used in similar studies. The dosage of SS corresponds to approximately 440 mg Sb/kg body weight (average mouse body weight 27 g), substantially higher than the standard therapeutic dose of 20 mg Sb/kg and the high dose (143 mg Sb/kg) that was clinically used by accident without serious toxicity. We chose to use the dose of SS for the study based on our previous observation in a pilot study (data not shown) that mice could tolerate daily dose of 20 mg Sb (approximately 700-800 mg Sb/kg). We also considered our observation that the effect of SS in inhibiting the growth of the cancer cell lines in vitro was dose-dependent with complete or near complete killing of the cancer cells at 100 pg Sb/ml (or 100 ug Sb/kg). In light of the relatively rapid rate of clearance of the drug in vivo, we decided to use the 440 mg Sb/kg dosage to ensure the detection of the effectiveness of the drug for this initial study.

For each of the cell lines, each of 16 mice received subcutaneous injection at the chest area of 3×106 cells/site (WM9) or 2×106 cells/site (DU145), two sites/mouse, on day 0. Mice were separated into four groups of four to receive treatment, injected into the thigh area and starting on day 2. Tumor size was measured with a caliper to determine the two perpendicular diameters of each tumor. Tumor volume was calculated using the method of the NCI (length×width 2 in millimeters/2=volume in cubic millimeters).

Discussion and Results

SS as a Single Agent has a Marked Anti-Tumor Activity In Vivo and Synergizes with IFNα to Eradicate Xenografts of Human Melanoma WM9 in Nude Mice.

Figure 22:
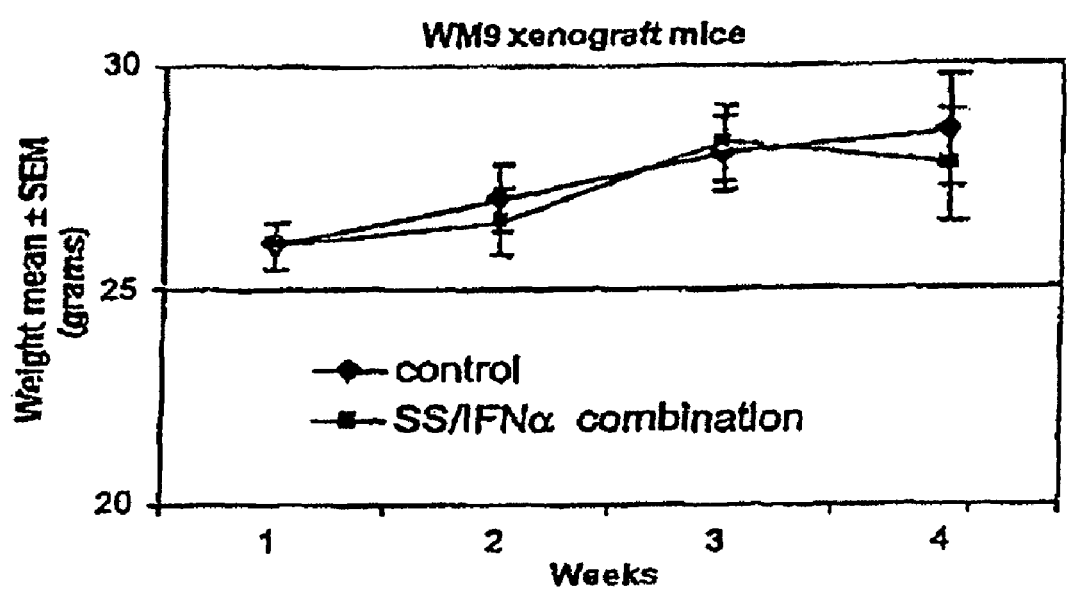
FIG. 22.

To test the anti-tumor effects of SS and its synergy with IFNα in vivo we determined the effect of SS, IFNα and their combination against xenografts of human WM9 melanoma in nude mice. WM9 cells were inoculated into nude mice which were then subjected to no treatment (control) or treatment for 23 days with single agents or their combination starting on day 2 following inoculation. Tumor volume of WM9 xenografts in the mice was determined during the treatment course as indicators of efficacy of the treatment (FIG. 22A).

WM9 cells in nude mice formed tumors that showed continuous growth in a time dependent manner in the absence of any treatment. Treatment with alone significantly suppressed WM9 tumor growth in the mice and resulted in an average tumor volume approximately 40% of the control group by the end of the treatment course (FIG. 22A, day 25 data). Interestingly, treatment with SS alone caused a dramatic tumor growth suppression (tumor volume about 20% of the controls on day 25), superior to that of IFNα treatment under the experimental conditions. Most strikingly, treatment with the combination of SS and IFNα led to a gradual shrinkage of WIND tumors which were visually invisible by day 18 (FIG. 22A). This absence of visible tumor in this group of mice continued till the end of the treatment course by day 25. Two mice of this group were observed for additional 8 weeks without treatment No visually visible tumor was detected in these mice at the inoculation sites during this additional observation period. Thus the combinational treatment eradicated the pre-formed WM9 tumors in the nude mice.

Statistical analysis of the data demonstrate that the differences of tumor volumes between the groups on day 25 were highly significant (t test: control vs. SS, IFNα and SS/IFNα, $p<0.01$; SS vs. IFNα, $p<0.01$; SS vs. SS/IFNα, $p<0.01$). Combinational analysis indicates that the interaction between SS and IFNα is synergistic.

SS Markedly Suppresses the Growth of Xenografts of Human Prostate Carcinoma DU145 in Nude Mice.

As shown in FIG. 22B, inoculation of DU145 cells in nude mice resulted in formation of tumors that was not significantly suppressed by IFNα monotherapy during the most part of the treatment duration, consistent with a previous study. A modest anti-tumor activity of the cytoldne was detected by the end of the treatment course with the average tumor volume approximately 70% of the control on day 25. In contrast, SS as a single agent markedly suppressed DU145 tumor growth and resulted in an average tumor volume of approximately 30% of the control by day 25. This anti-tumor activity of SS was further augmented when the drug was used in combination with IFNα (average tumor volume 18% of control on day 25), These results together demonstrated that SS has a marked anti-tumor activity against DU145 xenografts in nude mice and that the drug interacts with IFNα to achieve a striking growth inhibition of DU145 xenografts in nude mice.

The Effective Dosage of SS Against WM9 and DU145 Xenografts is Well Tolerated in Nude Mice.

As discussed above, the dosage of SS used for the treatment of nude mice was 12 mg Sb/mouse, s.c., daily (or approximately 440 mg/kg body weight). Thus dosage is much higher than the standard dose for Leishmaniasis (20 mg Sb/kg, daily). As an initial step to assess the toxicity of such a high dosage of SS in nude mice, we determined its effect on the viability and body weights of WM9 xenografts nude mice during the 25 day period of the study.

All of the 16 mice inoculated with WM9 cells survived till the end of the study (day 25) regardless their treatment (control, SS, IFNα or both, 4 mice/group). The average body weight of the mice subjected to combinational treatment with SS and IFNα showed no significant difference from that of the control group mice (FIG. 3) or those of the SS- or IFNα-treatment group (data not shown) during the study period. In addition, no obvious difference was noticed among the 4 groups of mice in their general appearance, feeding or activity. Dissection of two mice from each group of the mice revealed no apparent abnormality of the internal organs. Two mice of the combinational treatment group were observed for additional 8 weeks without treatment. They showed no visually obvious abnormality during the period, indicating that the treatment caused no serious longterm side effect.

In summary, these results demonstrate that SS, as a single agent, showed a significant activity, higher than that of IFNα, against the two types of tumors in vivo. Moreover, SS synergized with IFNα to eradicate the WM9 tumors in the nude mice with the combinational treatment for 16 days. We also found that SS synergized with IFNα to achieve striking growth inhibition of the DU-145 tumors superior to those of the two drugs used alone.

Additionally, the responses of the two tumor cell lines to SS and/or IFNα in vivo correlated with their responses -in vitro (comparing the results in FIG. 15A-B and FIG. 22): the WM9 cell line was more sensitive to the combination treatment of SS and IFNα in vivo than the DLT145 cell line, similar to our in vitro results. We also found that SS at the dosage used in the study (12 mg Sb, daily of 440 mg Sb/kg daily) was well tolerated with no serious side effect.

We conclude based on these results that (1) SS has a marked and broad anti-tumor activity in vivo as a single agent at a dosage that may be clinically achievable and tolerated; (2) the demonstrated synergy between SS and IFNα in vivo indicates that combinational usage of SS may significantly improve the current IFNα therapies in cancer treatment; (3) since SS targets PTPases and therefore functions via a mechanism distinct from those of current anticancer therapies, the drug may be useful as an alternative therapeutic for cancers non-responsive or resistant to conventional anti-cancer, therapies; (4) the correlation between in vitro and in vivo responses; of cancer cell lines to SS or SS/IFNα indicates that other human cancer cell lines sensitive to these agents in vitro, as detected in our preliminary studies, will be responsive to these agents in vivo as well; this further suggests that the human malignancies represented by the sensitive cell lines (e.g., human breast cancer cell line MDA231 and multiple myeloma cell line U266) may benefit from SS/IFNα combinational therapies; (5) since the nude mice study verified that the synergy between SS and IFNα as detected in vitro also occurs in vivo, the in vitro synergy of SS with other cytokines (e.g., IFNP) as detected in our preliminary studies may similarly exist in vivo; therefore, SS may be a useful adjuvant in IFNα therapy for viral or autoimmune diseases (e.g. hepatitis C and multiple sclerosis).

All of the references cited herein and appended hereto, including patents, patent applications, literature publications, and the like, are hereby incorporated in their entireties by reference.

While this invention has been described with an emphasis upon preferred embodiments, it will be obvious to those of ordinary skill in the art that variations of the preferred compounds and methods may be used and that it is intended that the invention may be practiced otherwise than as specifically described herein.

I claim:

1. A method of treating cancer in a patient in need thereof comprising administering to said patient a therapeutically effective amount of a sodium stibogluconate and interferon alpha, wherein said cancer is selected from the group consisting of lymphoma, multiple myeloma, leukemia, melanoma, prostate cancer, breast cancer, renal cancer, bladder cancer, and combinations thereof.

2. The method of claim 1, wherein said administration is parenteral.

3. The method of claim 2, wherein said parenteral administration is intravenous.

4. The method of claim 1, wherein said administration is of a sodium stibogluconate and interferon alpha is simultaneous.

5. The method of claim 1, wherein sodium stibogluconate first is administered followed by the subsequent administration of interferon alpha.

6. The method of claim 1, wherein interferon alpha is administered first followed by the subsequent administration of sodium stibogluconate.

7. The method of claim 5, wherein said subsequent administration is the same day.

8. The method of claim 5, wherein said subsequent administration is the following day.

9. The method of claim 5, wherein said subsequent administration is within one week.

10. The method of claim 6, wherein said subsequent administration is the same day.

11. The method of claim 6, wherein said subsequent administration is the following day.

12. The method of claim 6, wherein said subsequent administration is within one week.

13. The method of claim 1, wherein said effective amount of a sodium stibogluconate is from about 10 ug/mL, to about 400 mg/mL.

14. The method of claim 1, wherein said effective amount of a sodium stibogluconate is from about 25 ug/mL, to about 100 mg/mL.

15. The method of claim 1, wherein said effective amount of a sodium stibogluconate is from about 10 ug/mL, to about 20 mg/mL.

16. The method of claim 1, wherein said effective amount of a sodium stibogluconate is about 25 mg/mL.

17. The method of claim 1, wherein said effective amount of inteferon-alpha is about $2\times10^8$ IU/mg.

18. The method of claim 1, wherein said effective amount of inteferon-alpha is about 500,000 IU.

* * * * *